US006410323B1

(12) United States Patent
Roberts et al.

(10) Patent No.: US 6,410,323 B1
(45) Date of Patent: Jun. 25, 2002

(54) ANTISENSE MODULATION OF HUMAN RHO FAMILY GENE EXPRESSION

(75) Inventors: M. Luisa Roberts, Noank, CT (US); Lex M. Cowsert, Carlsbad, CA (US)

(73) Assignee: ISIS Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 09/387,341

(22) Filed: Aug. 31, 1999

(51) Int. Cl.$^7$ .......................... C12Q 1/68; C12N 15/85; C12P 19/34; C07H 21/04
(52) U.S. Cl. .......................... 435/375; 435/91.1; 435/6; 435/325; 435/366; 536/23.1; 536/24.31; 536/24.5
(58) Field of Search .......................... 435/6, 91.1, 325, 435/366, 375; 536/23.1, 24.5, 24.31; 514/44

(56) References Cited

PUBLICATIONS

Jen et al., Stem Cells 2000; 18:307–319.*
Green et al., J. A. Coll. Surg., (Jul. 2000), vol. 191, No. 1, pp. 93–105.*
Branch, TIBS (Feb. 1998), 23, pp. 45–50.*
Shinjo et al., Proc. Natl. Acad. Sci. USA, Dec. 1990, vol. 87, pp. 9853–9857.*
Qui et al., Molecular and Cellular Biology, Jun. 1997, vol. 17, No. 6, pp. 3449–3458.*
Milligan et al., Journal of Medicinal Chemistry, Jul. 1993, vol. 36, No. 14, pp. 1923–1937.*
Monia, Oligonucleotides As Therapeutics Agents, 1997, Wiley, Chicester (Ciba Foundation Symposium 209), pp. 107–123.*
delPeso, et al., "Rho proteins induce metastatic properties in vivo", Oncogene 1997 15, 3047–3057.
Engel, et al., "RhoB Is Stabilized by Transforming Growth Factor β and Antagonizes Transcriptional Activation",J. Biol. Chem. 1998, 273, 9921–9926.
Hall, A., "Rho GTPases and the Actin Cytoskeleton", Science, 1998 279, 509–514.
Khosravi–Far et al., "Increasing Complexity of Ras Signal Transduction: Involvement of Rho Family Proteins", Adv. Cancer Res. 1998 72, 57–107.
Kim, et al., "Protection from Reoxygenation Injury by Inhibition of racl", J. Clin. Invest. 1998 101, 1821–1826.
Mellor et al., "PRK1 Is Targeted to Endosomes by the Small GTPase, RhoB", J. Biol. Chem. 1998 273, 4811–4814.
Narumiya et al., "rho Gene Products, Botulinum C3 Exoenzyme and Cell Adhesion", Cell Signal, 1993, 5, 9–19.
Ren et al., "Modulation of small G protein isoprenylation by anticancer monoterpenes in in situ mammary gland epithelial cells",Carcinogenesis 1998, 19, 827–832.
Ridley, A.J., "The GTP–binding Protein Rho", Int. J. Biochem. Cell Biol. 1997, 29, 1225–1229.
Ridley et al., "The Small GT–Binding Protein rho Regulates the Assembly of Focal Adhesions and Actin Stress Fibers in Response to Growth Factors",Cell, 1992 70, 389–399.
Roux, et al., "The small GTPases Cdc42Hs, Rac1 and RhoG delineate Raf–independent pathways that cooperate to transform NIH3T3 cells", Curr. Biol. 1997 7, 629–637.
Suwa, et al., "Overexpression of the rhoC gene correlates with progression of ductal adenocarcinoma of the pancreas", Br. J. Cancer 1998 77, 147–152.
Takada et al., "The involvement of the rho gene product, a small molecular weight GTP–binding protein, in polyploidization of a human megakaryocytic cell line, CMK", Exp. Hemaol. 1996 24 524–530.
Vincent, et al., "Growth–Regulated Expression of rhoG, a New Member of the ras Homolog Gene Family", Mol. Cell. Biol. 1992 12, 3138–3148.
Zalcman, et al., "Regulation of Ras–related RhoB protein expression during the cell cycle", Oncogene, 1995 10, 1935–1945.
Brenner, B., et al., "L–Selectin Regulateds Actin Polymerisation via Activation of the Small G–Protein Rac2", Biochem. Biophys. Res. Commun. 1997 231 802–07.
Didsbury, J., et al., "rac, a Novel ras–related Family of Proteins That Are Botulinum Toxin Subsrates", J. Biol. Chem. 1989 264, 16378–26382.
Dorseuil, O., et al., "Inhibition of Superoxide Production in B Lymphocytes by Rac Antisense Oligonucleotides",, J. Biol. Chem 1992, 267, 20540–20542.
Vojtek, A.B., et al., "Rho Family Members: Activators of MAP Kinase Cascades", Cell 1995 82, 527–529.

\* cited by examiner

Primary Examiner—John L. LeGuyader
Assistant Examiner—M Schmidt
(74) Attorney, Agent, or Firm—Licata & Tyrrell P.C.

(57) ABSTRACT

This invention provides compositions and methods for modulating expression of members of the human Rho gene family, which encode low molecular weight GTPases that act as molecular switches in signal transduction. In preferred embodiments, Rho family members include RhoA, RhoB, RhoC, RhoG, Rac1 and cdc42. This invention is also directed to methods for inhibiting hyperproliferation of cells; these methods can be used diagnostically or therapeutically. Furthermore, this invention is directed to treatment of conditions associated with expression of the human Rho family members, particularly in hyperproliferative disorders.

13 Claims, No Drawings

ANTISENSE MODULATION OF HUMAN RHO FAMILY GENE EXPRESSION

FIELD OF THE INVENTION

This invention relates to compositions and methods for modulating expression of members of the human Rho gene family, which encode low molecular weight GTPases that act as molecular switches in signal transduction. This invention is also directed to methods for inhibiting hyperproliferation of cells; these methods can be used diagnostically or therapeutically. Furthermore, this invention is directed to treatment of conditions associated with expression of the human Rho family member genes.

BACKGROUND OF THE INVENTION

The Rho family of genes are a sub-family of low molecular weight GTPases and are related to each other based on sequence homology and function (Vojtek, A. B., and Cooper, J. A., *Cell* 1995, 82, 527–529). Other sub-families include Ras, Rab, Arf, and Ran. As GTPases, these proteins bind and hydrolyze GTP. In an active state, they bind to GTP and transduce signals of other proteins in signal transduction pathways. In their inactive state, they are bound to GDP. Members of the Rho family are typically involved in regulation of the actin cytoskeleton. Members of the Rho family include RhoA, RhoB, RhoC, RhoD, RhoE, RhoG, Rac1, Rac2, Rac3 and Cdc42.

Each class appears to have a unique function in actin reorganization. Rho has been shown to be essential for the formation of stress fibers and focal adhesions (Ridley, A. J. and Hall, A., *Cell* 1992, 70, 389–399). Focal adhesions are an area of the cell where integrin receptors cluster and extracellular matrix proteins such as fibronectin and collagen are bound. Stress fibers attach at these focal adhesions within a cell. Rac has been shown to be essential for the formation of membrane ruffles, which results from the formation of large vesicles within the cell (Ridley, A. J., et al., *Cell* 1992, 70, 401–410). Cdc42 (also known as Cdc42Hs and G25K) regulates the formation of filopodia, short bundles of actin filaments that protrude from a cell (Nobes, C. D. and Hall, A., *Cell* 1995, 81, 53–62). Such activities on cell morphology may play an important role in cell motility, cytokinesis, and endocytosis.

Additional functions for the Rho family have begun to be elucidated. Rac and Rho have been found to promote cadherin-based cell-cell adhesion (Takaishi, K., et al., *J. Cell Biol.* 1997, 139, 1047–1059). Rac1 and Cdc42 play a critical role in the c-jun amino-terminal kinase (JNK)/stress-activated protein kinase (SAPK) signaling pathway, thereby, potentially having an important role in gene transcription (Coso, O. A. et al., *Cell* 1995, 81, 1137–1146). RhoA, Rac1 and Cdc42 also regulate transcription through JNK-independent pathways by binding to either serum response factor (SRF; Hill, C. S., et al., *Cell* 1995, 81, 1159–1170) or NF-κB (Perona, R., et al., *Genes and Develop.* 1997, 11, 463–475).

Members of the Rac subfamily have also been found to regulate oxygen radical production. Both Rac1 (Sundaresan, M., et al., *Biochem. J.* 1996, 318, 379–382) and Rac2 (Knaus, U. G., et al., *Science* 1991, 254, 1512–1515) are involved in this process.

Members of the Rho family are thought to be involved in various disease processes, including cancer. Rho, Rac and Cdc42 all play a role in Ras transformation. Rac was found to essential for transformation by Ras, but not RafCAAX, a modified Raf kinase with a localization signal from K-ras (Qiu, R.-G., et al., *Nature* 1995 374, 457–459). Rho is not essential for Ras transformation, but acts cooperatively in transformation by Ras and RafCAAX (Qiu, R.-G., et al., *Proc. Natl. Acad. Sci. USA* 1995, 92, 11781–11785). Cdc42 was also found to be essential for Ras transformation, but its role is distinct from that of Rac (Qiu, R.-G., et al., *Mol. Cell Biol.* 1997, 17, 3449–3458). In addition to transformation, members to of the Rho family may also play a role in invasion and metastasis. Michiels, F. et al. (*Nature* 1995, 375, 338–340) demonstrated that T-lymphoma cells that constitutively expressed Rac1 became invasive. Yoshioka, K. et al. (*J. Biol. Chem.* 1998, 273, 5146–5154) found that cells stably transfected with RhoA were also invasive. The RhoB gene has been classified as an immediate-early gene, which means that its transcription is rapidly activated upon exposure to certain growth factors or mitogens. The factors shown to activate RhoD transcription include epidermal growth factor (EGF), platelet-derived growth factor (PDGF), genotoxic stress from UV light, alkylating xenobiotics and the retroviral oncogene v-fps. Each of these stimuli triggers DNA synthesis in cultures of high cell density (Engel et al., *J. Biol. Chem.*, 1998, 273, 9921–9926). The response of RhoB to these factors implies a role for RhoB in wound repair and tissue regeneration upon growth factor stimulation and tumorigenesis upon mitogen stimulation.

The involvement of Rho family proteins in ras-mediated transformation and tumor cell invasion suggests that they could be novel targets for cancer treatment (Ridley, A. J., *Int. J. Biochem. Cell Biol.* 1997, 29, 1225–1229). In particular, overexpression of the RhoC gene has been associated with pancreatic cancer. Suwa, H. et al. (*Br. J. Cancer*, 1998, 77, 147–152) looked for a role of RhoA, RhoB and RhoC genes in ductal adenocarcinoma of the pancreas. They found that expression levels of RhoC were higher in tumors than in normal tissue and that metastatic tumors expressed RhoC at higher levels than primary tumors. Rho C expression is also elevated in a megakaryocytic leukemia cell line, CMK. Takada et al., *Exp. Hematol.*, 1996, 24, 524–530. Manifestations of altered RhoB regulation also appear in disease states, including the development of cancer. Cellular transformation and acquisition of the metastatic phenotype are the two main changes normal cells undergo during the progression to cancer. Expression of constitutively activated forms of RhoB have been shown to cause tumorigenic transformation of NIH 3T3 and Rat1 rodent fibroblasts (Khosravi-Far et al., *Adv. Cancer Res.*, 1998, 72, 57–107). RhoB has also been shown to be overexpressed in human breast cancer tissues (Zalcman et al., *Oncogene*, 1995, 10, 1935–1945). RhoA is also believed to be involved in the development of cancer. Cellular transformation and acquisition of the metastatic phenotype are the two main changes normal cells undergo during the progression to cancer. Recent studies demonstrate that RhoA-regulated pathways can induce both changes in cells. Injecting cells transformed with rhoA genes directly into the bloodstream of mice produced metastasis, or tumor growth, in distant organs (del Peso et al., *Oncogene*, 1997, 15, 3047–3057).

It has also been suggested that inhibition of Rac genes may be useful for preventing reoxygenation injury as it occurs when ischemic cells undergo reperfusion (Kim, K.-S., et al., *J. Clin. Invest.* 1998, 101, 1821–826). With reoxygenation, reactive oxygen species are presented to the cell, greatly augmenting cell death. Kim, K.-S., et al. showed that adenoviral-mediated transfer of a dominant negative Rac1 could inhibit the formation of reactive oxygen species and protect cells against hypoxia/reoxygenation-induced cell death. They suggest that inhibition of rac1 would be useful, clinically, in treatment in cases where there is the possibility of reperfusion injury.

Manifestations of altered RhoA regulation also appear in both injury and disease states. It has been proposed that acute central nervous system trauma may contribute to the development of Alzheimer's disease. Findings that show a high concentration of thrombin, a serine-protease in the blood clotting cascade, localized to the plaques of Alzheimer's disease brains support this claim. An excess of thrombin has been shown to stimulate Rho A activity with a concomitant increase in apoptosis (programmed cell death) (Donovan et al., *J. Neurosci.*, 1997, 17, 5316–5326). These studies also imply a role for RhoA in wound repair and clotting disorders.

Although members of the Rho family have been implicated in various disease processes including cancer and reoxygenation injury, no effective therapy specifically targeting these proteins is available. Antisense oligonucleotides have been used to study the role of some Rho family members in various physiological processes. Dorseuil, O., et al. (*J. Biol. Chem.* 1992, 267, 20540–20542) used an 16-mer antisense oligonucleotide targeted to the start site of both Rac1 and Rac2 and demonstrated a dose-dependent reduction in superoxide production in whole cells. Brenner, B., et al. (*Biochem. Biophys. Res. Commun.* 1997, 231, 802–807) used a similar oligonucleotide (a 15-mer targeted to the start site) and showed that inhibition of Rac2 protein expression prevented L-selectin-induced actin polymerization. An 45-mer antisense oligonucleotide targeted to the 3'-UTR has also been used as a probe for rac1 (Didsbury, I., et al., *J. Biol. Chem.* 1989, 264, 16378–16382).

Thus, there remains an unmet need for compositions and methods targeting expression of Rho family members, and disease processes associated there-with.

SUMMARY OF THE INVENTION

The present invention provides oligonucleotides which are targeted to nucleic acids encoding members of the human Rho gene family and are capable of modulating Rho family members expression. The present invention also provides chimeric oligonucleotides targeted to nucleic acids encoding human Rho family members. The oligonucleotides of the invention are believed to be useful both diagnostically and therapeutically, and are believed to be particularly useful in the methods of the present invention.

The present invention also comprises methods of modulating the expression of human Rho family members using the oligonucleotides of the invention. Methods of inhibiting Rho family members expression are provided; these methods are believed to be useful both therapeutically and diagnostically. These methods are also useful as tools, for example, for detecting and determining the role of Rho family member expression in various cell functions and physiological processes and conditions and for diagnosing conditions associated with expression of Rho family members.

The present invention also comprises methods for diagnosing and treating cancer and preventing reoxygenation injury. These methods are believed to be useful, for example, in diagnosing Rho family member-associated disease progression. These methods employ the oligonucleotides of the invention. These methods are believed to be useful both therapeutically, including prophylactically, and as clinical research and diagnostic tools.

DETAILED DESCRIPTION OF THE INVENTION

Members of the Rho family of GTPases are essential for transformation by Ras and play a role in tumor cell invasion. In addition, the Rac subfamily is a regulator of oxygen radical formation. As such, they represent attractive targets for antineoplastic therapy and preventative agents for radical deoxygenation. In particular, modulation of the expression of RhoC may be useful for the treatment of pancreatic carcinomas and modulation of Rac1 may be useful for preventing ischemia/reperfusion injury.

Antisense oligonucleotides targeting members of the Rho family represent a novel therapeutic approach.

The present invention employs antisense compounds, particularly oligonucleotides, for use in modulating the function of nucleic acid molecules encoding Rho family members, ultimately modulating the amount of a Rho family member produced. This is accomplished by providing oligonucleotides which specifically hybridize with nucleic acids, preferably mRNA, encoding a Rho family member.

This relationship between an antisense compound such as an oligonucleotide and its complementary nucleic acid target, to which it hybridizes, is commonly referred to as "antisense". "Targeting" an oligonucleotide to a chosen nucleic acid target, in the context of this invention, is a multistep process. The process usually begins with identifying a nucleic acid sequence whose function is to be modulated. This may be, as examples, a cellular gene (or mRNA made from the gene) whose expression is associated with a particular disease state, or a foreign nucleic acid from an infectious agent. In the present invention, the targets are nucleic acids encoding Rho family members; in other words, a gene encoding a Rho family member, or mRNA expressed from a Rho family member gene. mRNA which encodes a Rho family member is presently the preferred target. The targeting process also includes determination of a site or sites within the nucleic acid sequence for the antisense interaction to occur such that modulation of gene expression will result.

In accordance with this invention, persons of ordinary skill in the art will understand that messenger RNA includes not only the information to encode a protein using the three letter genetic code, but also associated ribonucleotides which form a region known to such persons as the 5'-untranslated region, the 3'-untranslated region, the 5' cap region and intron/exon junction ribonucleotides. Thus, oligonucleotides may be formulated in accordance with this invention which are targeted wholly or in part to these associated ribonucleotides as well as to the informational ribonucleotides. The oligonucleotide may therefore be specifically hybridizable with a transcription initiation site region, a translation initiation codon region, a 5' cap region, an intron/exon junction, coding sequences, a translation termination codon region or sequences in the 5'- or 3'-untranslated region. Since, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon." A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (prokaryotes). It is also known in the art that eukaryotic and prokaryotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of an mRNA molecule transcribed from a gene encoding a Rho family member, regardless of the sequence(s) of such codons. It is also known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively). The terms "start codon region," "AUG region" and "translation initiation codon region" refer to a portion of such an mRNA or gene that encompasses from about 25 to about 50 contiguous nucleotides in either direction (i.e., 5' or 3') from a translation initiation codon. This region is a preferred target region. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon. This region is a preferred target region. The open reading frame (ORF) or "coding region," which is known in the art to refer to the region between the translation initiation codon and the translation termination codon, is also a region which may be targeted effectively. Other preferred target regions include the 5' untranslated region (5'UTR), known in the art to refer to the portion of an mRNA in the 5' direction from the translation initiation codon, and thus including nucleotides between the 5' cap site and the translation initiation codon of an mRNA or corresponding nucleotides on the gene and the 3' untranslated region (3'UTR), known in the art to refer to the portion of an mRNA in the 3' direction from the translation termination codon, and thus including nucleotides between the translation termination codon and 3' end of an mRNA or corresponding nucleotides on the gene. The 5' cap of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap. The 5' cap region may also be a preferred target region.

Although some eukaryotic mRNA transcripts are directly translated, many contain one or more regions, known as "introns," which are excised from a pre-mRNA transcript to yield one or more mature mRNA. The remaining (and therefore translated) regions are known as "exons" and are spliced together to form a continuous mRNA sequence. mRNA splice sites, i.e., exon-exon or intron-exon junctions, may also be preferred target regions, and are particularly useful in situations where aberrant splicing is implicated in disease, or where an overproduction of a particular mRNA splice product is implicated in disease. Aberrant fusion junctions due to rearrangements or deletions are also preferred targets. Targeting particular exons in alternatively spliced mRNAs may also be preferred. It has also been found that introns can also be effective, and therefore preferred, target regions for antisense compounds targeted, for example, to DNA or pre-mRNA.

Once the target site or sites have been identified, oligonucleotides are chosen which are sufficiently complementary to the target, i.e., hybridize sufficiently well and with sufficient specificity, to give the desired modulation.

"Hybridization", in the context of this invention, means hydrogen bonding, also known as Watson-Crick base pairing, between complementary bases, usually on opposite nucleic acid strands or two regions of a nucleic acid strand. Guanine and cytosine are examples of complementary bases which are known to form three hydrogen bonds between them. Adenine and thymine are examples of complementary bases which form two hydrogen bonds between them.

"Specifically hybridizable" and "complementary" are terms which are used to indicate a sufficient degree of complementarity such that stable and specific binding occurs between the DNA or RNA target and the oligonucleotide.

It is understood that an oligonucleotide need not be 100% complementary to its target nucleic acid sequence to be specifically hybridizable. An oligonucleotide is specifically hybridizable when binding of the oligonucleotide to the target interferes with the normal function of the target molecule to cause a loss of utility, and there is a sufficient degree of complementarity to avoid non-specific binding of the oligonucleotide to non-target sequences under conditions in which specific binding is desired, i.e., under physiological conditions in the case of in vivo assays or therapeutic treatment or, in the case of in vitro assays, under conditions in which the assays are conducted.

Hybridization of antisense oligonucleotides with mRNA interferes with one or more of the normal functions of mRNA. The functions of mRNA to be interfered with include all vital functions such as, for example, translocation of the RNA to the site of protein translation, translation of protein from the RNA, splicing of the RNA to yield one or more mRNA species, and catalytic activity which may be engaged in by the RNA. Binding of specific protein(s) to the RNA may also be interfered with by antisense oligonucleotide hybridization to the RNA.

The overall effect of interference with mRNA function is modulation of expression of a Rho family member. In the context of this invention "modulation" means either inhibition or stimulation; i.e., either a decrease or increase in expression. This modulation can be measured in ways which are routine in the art, for example by Northern blot assay of mRNA expression, or reverse transcriptase PCR, as taught in the examples of the instant application or by Western blot or ELISA assay of protein expression, or by an immunoprecipitation assay of protein expression. Effects on cell proliferation or tumor cell growth can also be measured, as taught in the examples of the instant application. Inhibition is presently preferred.

The oligonucleotides of this invention can be used in diagnostics, therapeutics, prophylaxis, and as research reagents and in kits. Since the oligonucleotides of this invention hybridize to nucleic acids encoding a Rho family member, sandwich, colorimetric and other assays can easily be constructed to exploit this fact. Provision of means for detecting hybridization of oligonucleotide with a Rho family member gene or mRNA can routinely be accomplished. Such provision may include enzyme conjugation, radiolabelling or any other suitable detection systems. Kits for detecting the presence or absence of a Rho family member may also be prepared.

The present invention is also suitable for diagnosing abnormal proliferative states in tissue or other samples from patients suspected of having a hyperproliferative disease such as cancer. The ability of the oligonucleotides of the present invention to inhibit cell proliferation may be employed to diagnose such states. A number of assays may be formulated employing the present invention, which assays will commonly comprise contacting a tissue sample with an oligonucleotide of the invention under conditions selected to permit detection and, usually, quantitation of such inhibition. In the context of this invention, to "contact" tissues or cells with an oligonucleotide or oligonucleotides means to add the oligonucleotide(s), usually in a liquid carrier, to a cell suspension or tissue sample, either in vitro or ex vivo, or to administer the oligonucleotide(s) to cells or tissues within an animal. Similarly, the present invention can be used to distinguish a Rho family member-associated tumor from tumors having other etiologies, or those associated with one rho family member from another, in order that an efficacious treatment regimen can be designed.

The oligonucleotides of this invention may also be used for research purposes. Thus, the specific hybridization exhibited by the oligonucleotides may be used for assays, purifications, cellular product preparations and in other methodologies which may be appreciated by persons of ordinary skill in the art.

In the context of this invention, the term "oligonucleotide" refers to an oligomer or polymer of ribonucleic acid or deoxyribonucleic acid. This term includes oligonucleotides composed of naturally-occurring nucleobases, sugars and covalent intersugar (backbone) linkages as well as oligonucleotides having non-naturally-occurring portions which function similarly. Such modified or substituted oligonucleotides are often preferred over native forms because of desirable properties such as, for example, enhanced cellular uptake, enhanced binding to target and increased stability in the presence of nucleases.

The antisense compounds in accordance with this invention preferably comprise from about 5 to about 50 nucleobases. Particularly preferred are antisense oligonucleotides comprising from about 8 to about 30 nucleobases (i.e. from about 8 to about 30 linked nucleosides). As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn the respective ends of this linear polymeric structure can be further joined to form a circular structure, however, open linear structures are generally preferred. Within the oligonucleotide structure, the phosphate groups are commonly referred to as forming the internucleoside backbone of the oligonucleotide. The normal linkage or backbone of RNA and DNA is a 3' to 5' phosphodiester linkage.

Specific examples of preferred antisense compounds useful in this invention include oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides.

Preferred modified oligonucleotide backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid forms are also included.

Representative United States patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361 and 5,625,050.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439.

In other preferred oligonucleotide mimetics, both the sugar and the internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262. Further teaching of PNA compounds can be found in Nielsen et al. (*Science,* 1991, 254, 1497–1500).

Most preferred embodiments of the invention are oligonucleotides with phosphorothioate backbones and oligonucleosides with heteroatom backbones, and in particular —$CH_2$13 NH—O—$CH_2$—, —$CH_2$—N($CH_3$)—O—$CH_2$— [known as a methylene (methylimino) or MMI backbone], —$CH_2$—N($CH_3$)—$CH_2$—, —$CH_2$—N($CH_3$)—N($CH_3$)—$CH_2$— and —O—N($CH_3$)—$CH_2$—$CH_2$— [wherein the native phosphodiester backbone is represented as —O—P—O—$CH_2$—] of the above referenced U.S. Pat. No. 5,489, 677, and the amide backbones of the above referenced U.S. Pat. No. 5,602,240. Also preferred are oligonucleotides having morpholino backbone structures of the above-referenced U.S. Pat. No. 5,034,506.

Modified oligonucleotides may also contain one or more substituted sugar moieties. Preferred oligonucleotides comprise one of the following at the 2' position: OH; F; O—, S—, or N-alkyl, O-alkyl-O-alkyl, O—, S—, or N-alkenyl, or O—, S— or N-alkynyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are $O[(CH_2)_nO]_mCH_3$, $O(CH2)_nOCH_3$, $O(CH_2)_2ON(CH_3)_2$, $O(CH_2)_nNH_2$, $O(CH_2)_nCH_3$, $O(CH_2)_nONH_2$, and $O(CH_2)_nON[(CH_2)_nCH_3)]_2$, where n and m are from 1 to about 10. Other preferred oligonucleotides comprise one of the following at the 2' position: $C_1$ to $C_{10}$ lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, poly-alkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy (2'-O—$CH_2CH_2OCH_3$, also known as 2'-O-(2-methoxyethyl) or 2'-MOE) (Martin et al., *Helv. Chim. Acta* 1995, 78, 486–504) i.e., an alkoxyalkoxy group. A further preferred modification includes 2'-dimethylaminooxyethoxy, i.e., a $O(CH_2)_2ON(CH_3)_2$ group, also known as 2'-DMAOE, as described in U.S. application Ser. No. 09/016,520, filed on Jan. 30, 1998, which is commonly owned with the instant application and the contents of which are herein incorporated by reference.

Other preferred modifications include 2'-methoxy (2'-O—$CH_3$), 2'-aminopropoxy (2'-$OCH_2CH_2CH_2NH_2$) and 2'-fluoro (2'-F). Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar. Representative United States patents that teach the preparation of such modified sugars structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,0531 5,639,873; 5,646,265; 5,658,873; 5,670,633; and 5,700,920.

Oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C or m5c), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further nucleobases include those disclosed in U.S. Pat. No. 3,687,808, those disclosed in the *Concise Encyclopedia Of Polymer Science And Engineering* 1990, pages 858–859, Kroschwitz, J. I., ed. John Wiley & Sons, those disclosed by Englisch et al. (*Angewandte Chemie, International Edition* 1991, 30, 613–722), and those disclosed by Sanghvi, Y. S., Chapter 15, *Antisense Research and Applications* 1993, pages 289–302, Crooke, S. T. and Lebleu, B., ed., CRC Press. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6–1.2° C. (Sanghvi, Y. S., Crooke, S. T. and Lebleu, B., eds., *Antisense Research and Applications* 1993, CRC Press, Boca Raton, pages 276–278) and are presently preferred base substitutions, even more particularly when combined with 2'-O-methoxyethyl sugar modifications.

Representative United States patents that teach the preparation of certain of the above noted modified nucleobases as well as other modified nucleobases include, but are not limited to, the above noted U.S. Pat. No. 3,687,808, as well as U.S. Pat. Nos.: 4,845,205; 5,130,302; 5,134,066; 5,175, 273; 5,367,066; 5,432,272; 5,457,187; 5,459,255; 5,484, 908; 5,502,177; 5,525,711; 5,552,540; 5,587,469; 5,594, 121, 5,596,091; 5,614,617; and 5,681,941.

Another modification of the oligonucleotides of the invention involves chemically linking to the oligonucleotide one or more moieties or conjugates which enhance the activity, cellular distribution or cellular uptake of the oligonucleotide. Such moieties include but are not limited to lipid moieties such as a cholesterol moiety (Letsinger et al., *Proc. Natl. Acad. Sci. USA* 1989, 86, 6553–6556), cholic acid (Manoharan et al., *Bioorg. Med. Chem. Lett.* 1994, 4, 1053–1059), a thioether, e.g., hexyl-S-tritylthiol (Manoharan et al., *Ann. N.Y. Acad. Sci.* 1992, 660, 306–309; Manoharan et al., *Bioorg. Med. Chem. Let.* 1993, 3, 2765–2770), a thiocholesterol (Oberhauser et al., *Nucl. Acids Res.* 1992, 20, 533–538), an aliphatic chain, e.g., dodecandiol or undecyl residues (Saison-Behmoaras et al., *EMBO J.* 1991, 10, 1111–1118; Kabanov et al., *FEBS Lett.* 1990, 259, 327–330; Svinarchuk et al., *Biochimie* 1993, 75, 49–54), a phospholipid, e.g., di-hexadecyl-rac-glycerol or triethylammonium 1,2-di-O-hexadecyl-rac-glycero-3-H-phosphonate (Manoharan et al., *Tetrahedron Lett.* 1995, 36, 3651–3654; Shea et al., *Nucl. Acids Res.* 1990, 18, 3777–3783), a polyamine or a polyethylene glycol chain (Manoharan et al., *Nucleosides & Nucleotides* 1995, 14, 969–973), or adamantane acetic acid (Manoharan et al., *Tetrahedron Lett.* 1995, 36, 3651–3654), a palmityl moiety (Mishra et al., *Biochim. Biophys. Acta* 1995, 1264, 229–237), or an octadecylamine or hexylamino-carbonyl-oxycholesterol moiety (Crooke et al., *J. Pharmacol. Exp. Ther.* 1996, 277, 923–937).

Representative United States patents that teach the preparation of such oligonucleotide conjugates include, but are not limited to, U.S. Pat. Nos. 4,828,979; 4,948,882; 5,218, 105; 5,525,465; 5,541,313; 5,545,730; 5,552,538; 5,578, 717, 5,580,731; 5,580,731; 5,591,584; 5,109,124; 5,118, 802; 5,138,045; 5,414,077; 5,486,603; 5,512,439; 5,578, 718; 5,608,046; 4,587,044; 4,605,735; 4,667,025; 4,762, 779; 4,789,737; 4,824,941; 4,835,263; 4,876,335; 4,904, 582; 4,958,013; 5,082,830; 5,112,963; 5,214,136; 5,082, 830; 5,112,963; 5,214,136; 5,245,022; 5,254,469; 5,258, 506; 5,262,536; 5,272,250; 5,292,873; 5,317,098; 5,371, 241, 5,391,723; 5,416,203, 5,451,463; 5,510,475; 5,512, 667; 5,514,785; 5,565,552; 5,567,810; 5,574,142; 5,585,481; 5,587,371; 5,595,726; 5,597,696; 5,599,923; 5,599,928 and 5,688,941.

The present invention also includes oligonucleotides which are chimeric oligonucleotides. "Chimeric" oligonucleotides or "chimeras," in the context of this invention, are oligonucleotides which contain two or more chemically distinct regions, each made up of at least one nucleotide. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of antisense inhibition of gene expression. Cleavage of the RNA target can be routinely detected by gel electrophoresis and, if necessary, associated nucleic acid hybridization techniques known in the art. This RNAse H-mediated cleavage of the RNA target is distinct from the use of ribozymes to cleave nucleic acids. Ribozymes are not comprehended by the present invention.

Examples of chimeric oligonucleotides include but are not limited to "gapmers," in which three distinct regions are present, normally with a central region flanked by two regions which are chemically equivalent to each other but distinct from the gap. A preferred example of a gapmer is an oligonucleotide in which a central portion (the "gap") of the oligonucleotide serves as a substrate for RNase H and is preferably composed of 2'-deoxynucleotides, while the flanking portions (the 5' and 3' "wings") are modified to have greater affinity for the target RNA molecule but are unable to support nuclease activity (e.g., 2'-fluoro- or 2'-O-methoxyethyl-substituted). other chimeras include "wingmers," also known in the art as "hemimers," that is, oligonucleotides with two distinct regions. In a preferred example of a wingmer, the 5' portion of the oligonucleotide serves as a substrate for RNase H and is preferably composed of 2'-deoxynucleotides, whereas the 3' portion is modified in such a fashion so as to have greater affinity for the target RNA molecule but is unable to support nuclease activity (e.g., 2'-fluoro- or 2'-O-methoxyethyl- substituted), or vice-versa. In one embodiment, the oligonucleotides of the present invention contain a 2'-O-methoxyethyl (2'-O—CH$_2$CH$_2$OCH$_3$) modification on the sugar moiety of at least one nucleotide. This modification has been shown to increase both affinity of the oligonucleotide for its target and nuclease resistance of the oligonucleotide. According to the invention, one, a plurality, or all of the nucleotide subunits of the oligonucleotides of the invention may bear a 2'-O-methoxyethyl (—O—CH$_2$CH$_2$OCH) modification. oligonucleotides comprising a plurality of nucleotide subunits having a 2'-O-methoxyethyl modification can have such a modification on any of the nucleotide subunits within the oligonucleotide, and may be chimeric oligonucleotides. Aside from or in addition to 2'-O-methoxyethyl modifications, oligonucleotides containing other modifications which enhance antisense efficacy, potency or target affinity are also preferred. Chimeric oligonucleotides comprising one or more such modifications are presently preferred.

The oligonucleotides used in accordance with this invention may be conveniently and routinely made through the well-known technique of solid phase synthesis. Equipment for such synthesis is sold by several vendors including Applied Biosystems. Any other means for such synthesis may also be employed; the actual synthesis of the oligonucleotides is well within the talents of the routineer. It is well known to use similar techniques to prepare oligonucleotides such as the phosphorothioates and 2'-alkoxy or 2'-alkoxyalkoxy derivatives, including 2'-O-methoxyethyl oligonucleotides (Martin, P., Helv. Chim. Acta 1995, 78, 486–504). It is also well known to use similar techniques and commercially available modified amidites and controlled-pore glass (CPG) products such as biotin, fluorescein, acridine or psoralen-modified amidites and/or CPG (available from Glen Research, Sterling, Va.) to synthesize fluorescently labeled, biotinylated or other conjugated oligonucleotides.

The antisense compounds of the present invention include bioequivalent compounds, including pharmaceutically acceptable salts and prodrugs. This is intended to encompass any pharmaceutically acceptable salts, esters, or salts of such esters, or any other compound which, upon administration to an animal including a human, is capable of providing (directly or indirectly) the biologically active metabolite or residue thereof. Accordingly, for example, the disclosure is also drawn to pharmaceutically acceptable salts of the nucleic acids of the invention and prodrugs of such nucleic acids. A pharmaceutically acceptable salts@ are physiologically and pharmaceutically acceptable salts of the nucleic acids of the invention: i.e., salts that retain the desired biological activity of the parent compound and do not impart undesired toxicological effects thereto (see, for example, Berge et al., "Pharmaceutical Salts," J. of Pharma Sci. 1977, 66, 1–19).

For oligonucleotides, examples of pharmaceutically acceptable salts include but are not limited to (a) salts formed with cations such as sodium, potassium, ammonium, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (d) salts formed from elemental anions such as chlorine, bromine, and iodine.

The oligonucleotides of the invention may additionally or alternatively be prepared to be delivered in a Aprodrug@ form. The term Aprodrug® indicates a therapeutic agent that is prepared in an inactive form that is converted to an active form (i.e., drug) within the body or cells thereof by the action of endogenous enzymes or other chemicals and/or conditions. In particular, prodrug versions of the oligonucleotides of the invention are prepared as SATE [(S-acetyl-2-thioethyl) phosphate] derivatives according to the methods disclosed in WO 93/24510 to Gosselin et al., published Dec. 9, 1993.

For therapeutic or prophylactic treatment, oligonucleotides are administered in accordance with this invention. Oligonucleotide compounds of the invention may be formulated in a pharmaceutical composition, which may include pharmaceutically acceptable carriers, thickeners, diluents, buffers, preservatives, surface active agents, neutral or cationic lipids, lipid complexes, liposomes, penetration enhancers, carrier compounds and other pharmaceutically acceptable carriers or excipients and the like in addition to the oligonucleotide. Such compositions and formulations are comprehended by the present invention.

Pharmaceutical compositions comprising the oligonucleotides of the present invention may include penetration enhancers in order to enhance the alimentary delivery of the oligonucleotides. Penetration enhancers may be classified as belonging to one of five broad categories, i.e., fatty acids, bile salts, chelating agents, surfactants and non-surfactants (Lee et al., *Critical Reviews in Therapeutic Drug Carrier Systems* 1991, 8, 91–192; Muranishi, *Critical Reviews in Therapeutic Drug Carrier Systems* 1990, 7, 1–33). One or more penetration enhancers from one or more of these broad categories may be included.

Various fatty acids and their derivatives which act as penetration enhancers include, for example, oleic acid, lauric acid, capric acid, myristic acid, palmitic acid, stearic acid, linoleic acid, linolenic acid, dicaprate, tricaprate, recinleate, monoolein (a.k.a. 1-monooleoyl-rac-glycerol), dilaurin, caprylic acid, arachidonic acid, glyceryl 1-monocaprate, 1-dodecylazacycloheptan-2-one, acylcarnitines, acylcholines, mono- and di-glycerides and physiologically acceptable salts thereof (i.e., oleate, laurate, caprate, myristate, palmitate, stearate, linoleate, etc.) (Lee et al., *Critical Reviews in Therapeutic Drug Carrier Systems* 1991, page 92; Muranishi, *Critical Reviews in Therapeutic Drug Carrier Systems* 1990, 7, 1; El-Hariri et al., *J. Pharm. Pharmacol.* 1992 44, 651–654).

The physiological roles of bile include the facilitation of dispersion and absorption of lipids and fat-soluble vitamins (Brunton, Chapter 38 In: *Goodman & Gilman's The Pharmacological Basis of Therapeutics*, 9th Ed., Hardman et al., eds., McGraw-Hill, New York, N.Y., 1996, pages 934–935). Various natural bile salts, and their synthetic derivatives, act as penetration enhancers. Thus, the term "bile salt" includes any of the naturally occurring components of bile as well as any of their synthetic derivatives.

Complex formulations comprising one or more penetration enhancers may be used. For example, bile salts may be used in combination with fatty acids to make complex formulations.

Chelating agents include, but are not limited to, disodium ethylenediaminetetraacetate (EDTA), citric acid, salicylates (e.g., sodium salicylate, 5-methoxysalicylate and homovanilate), N-acyl derivatives of collagen, laureth-9 and N-amino acyl derivatives of beta-diketones (enamines) [Lee et al., *Critical Reviews in Therapeutic Drug Carrier Systems* 1991, page 92; Muranishi, *Critical Reviews in Therapeutic Drug Carrier Systems* 1990, 7, 1–33; Buur et al., *J. Control Rel.* 1990, 14, 43–51). Chelating agents have the added advantage of also serving as DNase inhibitors.

Surfactants include, for example, sodium lauryl sulfate, polyoxyethylene-9-lauryl ether and polyoxyethylene-20-cetyl ether (Lee et al., *Critical Reviews in Therapeutic Drug Carrier Systems* 1991, page 92); and perfluorochemical emulsions, such as FC-43 (Takahashi et al., *J. Pharm. Phamacol.* 1988, 40, 252–257).

Non-surfactants include, for example, unsaturated cyclic ureas, 1-alkyl- and 1-alkenylazacyclo-alkanone derivatives (Lee et al., *Critical Reviews in Therapeutic Drug Carrier Systems* 1991, page 92); and non-steroidal anti-inflammatory agents such as diclofenac sodium, indomethacin and phenylbutazone (Yamashita et al., *J. Pharm. Pharmacol.* 1987, 39, 621–626).

As used herein, "carrier compound" refers to a nucleic acid, or analog thereof, which is inert (i.e., does not possess biological activity per se) but is recognized as a nucleic acid by in vivo processes that reduce the bioavailability of a nucleic acid having biological activity by, for example, degrading the biologically active nucleic acid or promoting its removal from circulation. The coadministration of a nucleic acid and a carrier compound, typically with an excess of the latter substance, can result in a substantial reduction of the amount of nucleic acid recovered in the liver, kidney or other extracirculatory reservoirs, presumably due to competition between the carrier compound and the nucleic acid for a common receptor.

In contrast to a carrier compound, a "pharmaceutically acceptable carrier" (excipient) is a pharmaceutically acceptable solvent, suspending agent or any other pharmacologically inert vehicle for delivering one or more nucleic acids to an animal. The pharmaceutically acceptable carrier may be liquid or solid and is selected with the planned manner of administration in mind so as to provide for the desired bulk, consistency, etc., when combined with a nucleic acid and the other components of a given pharmaceutical composition. Typical pharmaceutically acceptable carriers include, but are not limited to, binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrates (e.g., starch, sodium starch glycolate, etc.); or wetting agents (e.g., sodium lauryl sulphate, etc.). Sustained release oral delivery systems and/or enteric coatings for orally administered dosage forms are described in U.S. Pat. Nos. 4,704,295; 4,556,552; 4,309,406; and 4,309,404.

The compositions of the present invention may additionally contain other adjunct components conventionally found in pharmaceutical compositions, at their art-established usage levels. Thus, for example, the compositions may contain additional compatible pharmaceutically-active materials such as, e.g., antipruritics, astringents, local anesthetics or anti-inflammatory agents, or may contain additional materials useful in physically formulating various dosage forms of the composition of present invention, such as dyes, flavoring agents, preservatives, antioxidants, opacifiers, thickening agents and stabilizers. However, such materials, when added, should not unduly interfere with the biological activities of the components of the compositions of the invention.

Regardless of the method by which the oligonucleotides of the invention are introduced into a patient, colloidal dispersion systems may be used as delivery vehicles to enhance the in vivo stability of the oligonucleotides and/or to target the oligonucleotides to a particular organ, tissue or cell type. Colloidal dispersion systems include, but are not limited to, macromolecule complexes, nanocapsules, microspheres, beads and lipid-based systems including oil-in-water emulsions, micelles, mixed micelles, liposomes and lipid:oligonucleotide complexes of uncharacterized structure. A preferred colloidal dispersion system is a plurality of liposomes. Liposomes are microscopic spheres having an aqueous core surrounded by one or more outer layers made up of lipids arranged in a bilayer configuration (see, generally, Chonn et al., *Current Op. Biotech.* 1995, 6, 698–708).

The pharmaceutical compositions of the present invention may be administered in a number of ways depending upon whether local or systemic treatment is desired and upon the area to be treated. Administration may be topical (including ophthalmic, vaginal, rectal, intranasal, epidermal, and transdermal), oral or parenteral. Parenteral administration includes intravenous drip, subcutaneous, intraperitoneal or intramuscular injection, pulmonary administration, e.g., by inhalation or insufflation, or intracranial, e.g., intrathecal or intraventricular, administration. Oligonucleotides with at least one 2'-O-methoxyethyl modification are believed to be particularly useful for oral administration.

Formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

Compositions for oral administration include powders or granules, suspensions or solutions in water or non-aqueous media, capsules, sachets or tablets. Thickeners, flavoring agents, diluents, emulsifiers, dispersing aids or binders may be desirable.

Compositions for parenteral administration may include sterile aqueous solutions which may also contain buffers, diluents and other suitable additives. In some cases it may be more effective to treat a patient with an oligonucleotide of the invention in conjunction with other traditional therapeutic modalities in order to increase the efficacy of a treatment regimen. In the context of the invention, the term "treatment regimen" is meant to encompass therapeutic, palliative and prophylactic modalities. For example, a patient may be treated with conventional chemotherapeutic agents, particularly those used for tumor and cancer treatment. Examples of such chemotherapeutic agents include but are not limited to daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine (CA), 5-azacytidine, hydroxyurea, deoxycoformycin, 4-hydroxyperoxycyclophosphoramide, 5-fluorouracil (5-FU), 5-fluorodeoxyuridine (5-FUdR), methotrexate (MTX), colchicine,taxol, vincristine, vinblastine, etoposide, trimetrexate, teniposide, cisplatin and diethylstilbestrol (DES). See, generally, *The Merck Manual of Diagnosis and Therapy*, 15th Ed. 1987, pp. 1206–1228, Berkow et al., eds., Rahway, N.J. Preferred are chemotherapeutic agents which are direct or indirect inhibitors of a Rho family member. These include MTX, Tomudex and fluorinated pyrimidines such as 5-FU and 5-FUdR. When used with the compounds of the invention, such chemotherapeutic agents may be used individually (e.g., 5-FU and oligonucleotide), sequentially (e.g., 5-FU and oligonucleotide for a period of time followed by MTX and oligonucleotide), or in combination with one or more other such chemotherapeutic agents (e.g., 5-FU, MTX and oligonucleotide, or 5-FU, radiotherapy and oligonucleotide).

The formulation of therapeutic compositions and their subsequent administration is believed to be within the skill of those in the art. Dosing is dependent on severity and responsiveness of the disease state to be treated, with the course of treatment lasting from several days to several months, or until a cure is effected or a diminution of the disease state is achieved. optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}$s found to be effective in vitro and in in vivo animal models. In general, dosage is from 0.01 μg to 100 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 μg to 100 g per kg of body weight, once or more daily, to once every 20 years.

Thus, in the context of this invention, by "therapeutically effective amount" is meant the amount of the compound which is required to have a therapeutic effect on the treated individual. This amount, which will be apparent to the skilled artisan, will depend upon the age and weight of the individual, the type of disease to be treated, perhaps even the gender of the individual, and other factors which are routinely taken into consideration when designing a drug treatment. A therapeutic effect is assessed in the individual by measuring the effect of the compound on the disease state in the animal. For example, if the disease to be treated is cancer, therapeutic effects are assessed by measuring the rate of growth or the size of the tumor, or by measuring the production of compounds such as cytokines, production of which is an indication of the progress or regression of the tumor.

The following examples illustrate the present invention and are not intended to limit the same.

EXAMPLES

Example 1

Synthesis of Oligonucleotides

Unmodified oligodeoxynucleotides are synthesized on an automated DNA synthesizer (Applied Biosystems model 380B) using standard phosphoramidite chemistry with oxidation by iodine. β-cyanoethyldiisopropyl-phosphoramidites are purchased from Applied Biosystems (Foster City, Calif.). For phosphorothioate oligonucleotides, the standard oxidation bottle was replaced by a 0.2 M solution of $^3$H-1,2-benzodithiole-3-one 1,1-dioxide in acetonitrile for the stepwise thiation of the phosphite linkages. The thiation cycle wait step was increased to 68 seconds and was followed by the capping step.

2'-methoxy oligonucleotides were synthesized using 2'-methoxy β-cyanoethyldiisopropyl-phosphoramidites (Chemgenes, Needham, Mass.) and the standard cycle for unmodified oligonucleotides, except the wait step after pulse delivery of tetrazole and base was increased to 360 seconds. Other 2'-alkoxy oligonucleotides were synthesized by a modification of this method, using appropriate 2'-modified amidites such as those available from Glen Research, Inc., Sterling, Va.

2'-fluoro oligonucleotides were synthesized as described in Kawasaki et al. (*J. Med. Chem.* 1993, 36, 831–841). Briefly, the protected nucleoside $N^6$-benzoyl-2'-deoxy-2'- fluoroadenosine was synthesized utilizing commercially available 9-β-D-arabinofuranosyladenine as starting material and by modifying literature procedures whereby the 2'-α-fluoro atom is introduced by a $S_N2$-displacement of a 2'-β-O-trifyl group. Thus $N^6$-benzoyl-9-β-D-arabinofuranosyladenine was selectively protected in moderate yield as the 3',5'-ditetrahydropyranyl (THP) intermediate. Deprotection of the THP and $N^6$-benzoyl groups was accomplished using standard methodologies and standard methods were used to obtain the 5'-dimethoxytrityl- (DMT) and 5'-DMT-3'-phosphoramidite intermediates.

The synthesis of 2'-deoxy-2'-fluoroguanosine was accomplished using tetraisopropyldisiloxanyl (TPDS) protected 9-β-D-arabinofuranosylguanine as starting material, and conversion to the intermediate diisobutyryl-arabinofuranosylguanosine. Deprotection of the TPDS group was followed by protection of the hydroxyl group with THP to give diisobutyryl di-THP protected arabinofuranosylguanine. Selective O-deacylation and triflation was followed by treatment of the crude product with fluoride, then deprotection of the THP groups. Standard methodologies were used to obtain the 5'-DMT- and 5'-DMT-3'-phosphoramidites.

Synthesis of 2'-deoxy-2'-fluorouridine was accomplished by the modification of a known procedure in which 2,2'-anhydro-1-β-D-arabinofuranosyluracil was treated with 70% hydrogen fluoride-pyridine. Standard procedures were used to obtain the 5'-DMT and 5'-DMT-3' phosphoramidites.

2'-deoxy-2'-fluorocytidine was synthesized via amination of 2'-deoxy-2'-fluorouridine, followed by selective protection to give $N^4$-benzoyl-2'-deoxy-2'-fluorocytidine. Standard procedures were used to obtain the 5'-DMT and 5'-DMT-3' phosphoramidites.

2'-(2-methoxyethyl)-modified amidites are synthesized according to Martin, P. (*Helv. Chim. Acta* 1995, 78, 486–506). For ease of synthesis, the last nucleotide was a deoxynucleotide. 2'-O—$CH_2CH_2OCH_3$-cytosines may be 5-methyl cytosines.

Synthesis of 5-Methyl Cytosine Monomers
2.2'-Anhydro[1-(β-D-arabinofuranosyl)-5-methyluridine]

5-Methyluridine (ribosylthymine, commercially available through Yamasa, Choshi, Japan) (72.0 g, 0.279 M), diphenyl-carbonate (90.0 g, 0.420 M) and sodium bicarbonate (2.0 g, 0.024 M) were added to DMF (300 mL). The mixture was heated to reflux, with stirring, allowing the evolved carbon dioxide gas to be released in a controlled manner. After 1 hour, the slightly darkened solution was concentrated under reduced pressure. The resulting syrup was poured into diethylether (2.5 L), with stirring. The product formed a gum. The ether was decanted and the residue was dissolved in a minimum amount of methanol (ca. 400 mL). The solution was poured into fresh ether (2.5 L) to yield a stiff gum. The ether was decanted and the gum was dried in a vacuum oven (60° C. at 1 mm Hg for 24 h) to give a solid which was crushed to a light tan powder (57 g, 85% crude yield). The material was used as is for further reactions.

2'-O-Methoxyethyl-5-methyluridine 2,2'-Anhydro-5-methyluridine (195 g, 0.81 M), tris(2-methoxyethyl)borate (231 g, 0.98 M) and 2-methoxyethanol (1.2 L) were added to a 2 L stainless steel pressure vessel and placed in a pre-heated oil bath at 160° C. After heating for 48 hours at 155–160° C., the vessel was opened and the solution evaporated to dryness and triturated with MeOH (200 mL). The residue was suspended in hot acetone (1 L). The insoluble salts were filtered, washed with acetone (150 mL) and the filtrate evaporated. The residue (280 g) was dissolved in $CH_3CN$ (600 mL) and evaporated. A silica gel column (3 kg) was packed in $CH_2Cl_2$/acetone/MeOH (20:5:3) containing 0.5% $Et_3NH$. The residue was dissolved in $CH_2Cl_2$ (250 mL) and adsorbed onto silica (150 g) prior to loading onto the column. The product was eluted with the packing solvent to give 160 g (63%) of product.

2'-O-Methoxyethyl-5'-O-dimethoxytrityl-5-methyluridine

2'-O-Methoxyethyl-5-methyluridine (160 g, 0.506 M) was co-evaporated with pyridine (250 mL) and the dried residue dissolved in pyridine (1.3 L). A first aliquot of dimethoxytrityl chloride (94.3 g, 0.278 M) was added and the mixture stirred at room temperature for one hour. A second aliquot of dimethoxytrityl chloride (94.3 g, 0.278 M) was added and the reaction stirred for an additional one hour. Methanol (170 mL) was then added to stop the reaction. HPLC showed the presence of approximately 70% product. The solvent was evaporated and triturated with $CH_3CN$ (200 mL). The residue was dissolved in $CHCl_3$ (1.5 L) and extracted with 2×500 mL of saturated $NaHCO_3$ and 2×500 mL of saturated NaCl. The organic phase was dried over $Na_2SO_4$, filtered and evaporated. 275 g of residue was obtained. The residue was purified on a 3.5 kg silica gel column, packed and eluted with EtOAc/-Hexane/Acetone (5:5:1) containing 0.5% $Et_3NH$. The pure fractions were evaporated to give 164 g of product. Approximately 20 g additional was obtained from the impure fractions to give a total yield of 183 g (57%).

3'-O-Acetyl-2'-O-methoxyethyl-5'-O-dimethoxytrityl-5-methyl-uridine

2'-O-Methoxyethyl-5'-O-dimethoxytrityl-5-methyluridine (106 g, 0.167 M), DMF/pyridine (750 mL of a 3:1 mixture prepared from 562 mL of DMF and 188 mL of pyridine) and acetic anhydride (24.38 mL, 0.258 M) were combined and stirred at room temperature for 24 hours. The reaction was monitored by tlc by first quenching the tlc sample with the addition of MeOH. Upon completion of the reaction, as judged by tlc, MeOH (50 mL) was added and the mixture evaporated at 35° C. The residue was dissolved in $CHCl_3$ (800 mL) and extracted with 2×200 mL of saturated sodium bicarbonate and 2×200 mL of saturated NaCl. The water layers were back extracted with 200 mL of $CHCl_3$. The combined organics were dried with sodium sulfate and evaporated to give 122 g of residue (approx. 90% product). The residue was purified on a 3.5 kg silica gel column and eluted using EtOAc/Hexane(4:1). Pure product fractions were evaporated to yield 96 g (84%).

3'-O-Acetyl-2'-O-methoxyethyl-5'-O-dimethoxytrityl-5-methyl-4-triazoleuridine

A first solution was prepared by dissolving 3'-O-acetyl-2'-O-methoxyethyl-5'-O-dimethoxytrityl-5-methyluridine (96 g, 0.144 M) in $CH_3CN$ (700 mL) and set aside. Triethylamine (189 mL, 1.44 M) was added to a solution of triazole (90 g, 1.3 M) in $CH_3CN$ (1 L), cooled to −5° C. and stirred for 0.5 h using an overhead stirrer. $POCl_3$ was added dropwise, over a 30 minute period, to the stirred solution maintained at 0–10° C., and the resulting mixture stirred for an additional 2 hours. The first solution was added dropwise, over a 45 minute period, to the later solution. The resulting reaction mixture was stored overnight in a cold room. Salts were filtered from the reaction mixture and the solution was evaporated. The residue was dissolved in EtOAc (1 L) and the insoluble solids were removed by filtration. The filtrate was washed with 1×300 mL of $NaHCO_3$ and 2×300 mL of saturated NaCl, dried over sodium sulfate and evaporated. The residue was triturated with EtOAc to give the title compound.

2'-O-Methoxyethyl-5'-O-dimethoxytrityl-5-methylcytidine

A solution of 3'-O-acetyl-2'-O-methoxyethyl-5'-O-dimethoxytrityl-5-methyl-4-triazoleuridine (103 g, 0.141 M) in dioxane (500 mL) and NH$_4$OH (30 mL) was stirred at room temperature for 2 hours. The dioxane solution was evaporated and the residue azeotroped with MeOH (2×200 mL). The residue was dissolved in MeOH (300 mL) and transferred to a 2 liter stainless steel pressure vessel. MeOH (400 mL) saturated with NH$_3$ gas was added and the vessel heated to 100° C. for 2 hours (tlc showed complete conversion). The vessel contents were evaporated to dryness and the residue was dissolved in EtOAc (500 mL) and washed once with saturated NaCl (200 mL). The organics were dried over sodium sulfate and the solvent was evaporated to give 85 g (95%) of the title compound.

N$^4$-Benzoyl-2'-O-methoxyethyl-5'-O-dimethoxytrityl-5-methyl-cytidine

2'-O-Methoxyethyl-5'-O-dimethoxytrityl-5-methylcytidine (85 g, 0.134 M) was dissolved in DMF (800 mL) and benzoic anhydride (37.2 g, 0.165 M) was added with stirring. After stirring for 3 hours, tlc showed the reaction to be approximately 95% complete. The solvent was evaporated and the residue azeotroped with MeOH (200 mL). The residue was dissolved in CHCl$_3$ (700 mL) and extracted with saturated NaHCO, (2×300 mL) and saturated NaCl (2×300 mL), dried over MgSO, and evaporated to give a residue (96 g). The residue was chromatographed on a 1.5 kg silica column using EtOAc/Hexane (1:1) containing 0.5% Et$_3$NH as the eluting solvent. The pure product fractions were evaporated to give 90 g (90%) of the title compound.

N$^4$-Benzoyl-2'-O-methoxyethyl-5'-O-dimethoxytrityl-5-methylcytidine-3'-amidite N$^4$-Benzoyl-2'-O-methoxyethyl-5'-O-dimethoxytrityl-5-methylcytidine (74 g, 0.10 M) was dissolved in CH$_2$Cl$_2$ (1 L). Tetrazole diisopropylamine (7.1 g) and 2-cyanoethoxy-tetra-(isopropyl)phosphite (40.5 mL, 0.123 M) were added with stirring, under a nitrogen atmosphere. The resulting mixture was stirred for 20 hours at room temperature (tlc showed the reaction to be 95% complete) The reaction mixture was extracted with saturated NaHCO$_3$ (1×300 mL) and saturated NaCl (3×300 mL). The aqueous washes were back-extracted with CH$_2$Cl$_2$ (300 mL), and the extracts were combined, dried over MgSO$_4$ and concentrated. The residue obtained was chromatographed on a 1.5 kg silica column using EtOAc\Hexane (3:1) as the eluting solvent. The pure fractions were combined to give 90.6 g (87%) of the title compound.

5-methyl-2'-deoxycytidine (5-me-C) containing oligonucleotides were synthesized according to published methods (Sanghvi et al., *Nucl. Acids Res.* 1993, 21, 3197–3203) using commercially available phosphoramidites (Glen Research, Sterling Va. or ChemGenes, Needham Mass.).

Oligonucleotides having methylene(methylimino) (MMI) backbones are synthesized according to U.S. Pat. No. 5,378, 825, which is coassigned to the assignee of the present invention and is incorporated herein in its entirety. For ease of synthesis, various nucleoside dimers containing MMI linkages were synthesized and incorporated into oligonucleotides. other nitrogen-containing backbones are synthesized according to WO 92/20823 which is also coassigned to the assignee of the present invention and incorporated herein in its entirety.

Oligonucleotides having amide backbones are synthesized according to De Mesmaeker et al. (*Acc. Chem. Res.* 1995, 28, 366–374). The amide moiety is readily accessible by simple and well-known synthetic methods and is compatible with the conditions required for solid phase synthesis of oligonucleotides.

Oligonucleotides with morpholino backbones are synthesized according to U.S. Pat. No. 5,034,506 (Summerton and Weller).

Peptide-nucleic acid (PNA) oligomers are synthesized according to P. E. Nielsen et al. (*Science* 1991, 254, 1497–1500).

After cleavage from the controlled pore glass column (Applied Biosystems) and deblocking in concentrated ammonium hydroxide at 55° C. for 18 hours, the oligonucleotides are purified by precipitation twice out of 0.5 M NaCl with 2.5 volumes ethanol. Synthesized oligonucleotides were analyzed by polyacrylamide gel electrophoresis on denaturing gels and judged to be at least 85% full length material. The relative amounts of phosphorothioate and phosphodiester linkages obtained in synthesis were periodically checked by $^{31}$P nuclear magnetic resonance spectroscopy, and for some studies oligonucleotides were purified by HPLC, as described by Chiang et al. (*J. Biol. Chem.* 1991, 266, 18162). Results obtained with HPLC-purified material were similar to those obtained with non-HPLC purified material.

Example 2

Human RhoA Oligonucleotide Sequences

Antisense oligonucleotides were designed to target human RhoA. Target sequence data are from the RhoA cDNA sequence published by Yeramian, P., et al. (*Nucleic Acids Res.* 1987, 15, 1869); Genbank accession number X05026, provided herein as SEQ ID NO: 1. Oligonucleotides were synthesized primarily with phosphorothioate linkages. Oligonucleotide sequences are shown in Table 1.

A549 cells, human lung carcinoma cells (obtained from American Type Culture Collection) were cultured in Dulbecco's modified Eagle's medium (DMEM) low glucose, 10% fetal calf serum, and penicillin (50 units/ml)/streptomycin (50 mg/ml). Cells were passaged at 90–956 confluency. All culture reagents were obtained from Life Technologies (GIBCO BRL, Rockville, Md.).

A549 cells were plated at a starting cell number of approximately 2×10$^5$ cells per well. After twenty-four hours, at 80–90% confluency, the cells were washed twice with Opti-Mem (GIBCO BRL) and the oligonucleotide formulated in LIPOFECTIN (GIBCO BRL), a 1:1 (w/w) liposome formulation of the cationic lipid N-(1-(2,3-dioleyloxy) propyl]-n,n,n-trimethylammonium chloride (DOTMA), and dioleoyl phosphotidylethanolamine (DOPE) in membrane filtered water, at a constant ratio of 2.5 mg/ml LIPOFECTIN to 100 nM oligonucleotide, in Opti-Mem. For an initial screen, the oligonucleotide concentration was 300 nM. Treatment was for four hours. After treatment, the media was removed and the cells were further incubated in DMEM containing 10% FCS, and penicillin/streptomycin for 24 or 48 hours.

mRNA was isolated using the MICRO-FASTTRACK kit (Invitrogen, Carlsbad, Calif.), separated on a 1% agarose gel, transferred to Hybond-N+ membrane (Amersham, Arlington Heights, Ill.), a positively charged nylon membrane, and probed. A RhoA probe was generated using asymmetric PCR, in the presence of a [$^{32}$P]-dCTP (Amersham), with the following primers:

Forward: 5'-TGCAAGCACAGCCCTTATG-3' SEQ ID NO. 2

Reverse: 5'-TGTCAAAGGACCCTGGTG-3' SEQ ID NO. 3

A glyceraldehyde 3-phosphate dehydrogenase (G3PDH) probe was purchased from Clontech (Palo Alto, Calif.), Catalog Number 9801-1. The probe was labeled by random primer using the Large Fragment of DNA polymerase (Klenow fragment) (GIBCO BRL) as described in Maniatis, T., et al., Molecular Cloning: A Laboratory Manual, 1989. mRNA was quantitated by a PhosphoImager (Molecular Dynamics, Sunnyvale, Calif.).

TABLE 1

Nucleotide Sequences of RhoA Oligonucleotides

| ISIS NO. | NUCLEOTIDE SEQUENCE (5' -> 3') | SEQ ID NO: | NUCLEOTIDE CO-ORDINATES[1] | TARGET GENE GENE TARGET REGION |
|---|---|---|---|---|
| 16191 | AGTCGCAAACTCGGAGAC | 4 | 0085–0102 | 5'-UTR |
| 16192 | TTGCTCAGGCAACGAATC | 5 | 0142–0159 | AUG |
| 16193 | CTGAAGACTATGAGCAAGCATG | 6 | 0214–0235 | Coding |
| 16194 | CTCATCATTCCGAAGATCC | 7 | 0515–0533 | Coding |
| 16195 | CCAATCCTGTTTGCCATATCTC | 8 | 0592–0613 | Coding |
| 16196 | CCATCTTTGGTCTTTGCTGAAC | 9 | 0634–0655 | Coding |
| 16197 | GCAGAGCAGCTCTCGTAGCCA | 10 | 0676–0696 | Coding |
| 16198 | TCACAAGACAAGGCAACCAG | 11 | 0721–0740 | Stop |
| 16199 | AGGCCAGTAATCATACACTA | 12 | 0799–0818 | 3'-UTR |
| 16200 | GTTGGCTTCTAAATACTGGT | 13 | 0871–0890 | 3'-UTR |
| 16201 | GGCTGTTAGAGCAGTGTCAA | 14 | 0937–0956 | 3'-UTR |
| 16202 | AGCGCCTGGTGTGTCAGGTG | 15 | 0971–0990 | 3'-UTR |
| 16203 | TAGTTACAGCCTAATTGACA | 16 | 1051–1073 | 3'-UTR |
| 16913 | GGCACCTGTTGGGTGAGCTG | 17 | 16202 control | |
| 16914 | ACACTCTTGCTTACCGTACCTT | 18 | 16195 control | |
| 16915 | TGCGGTAAGTGCGGTATCAA | 19 | 16201 control | |

[1]All linkages are phosphorothioate linkages.
[2]Co-ordinates from Genbank Accession No. X05026, locus name "HSRHOB" SEQ ID NO. 1.

Results are shown in Table 2. Oligonucleotides 16193 (SEQ ID NO. 6), 16195 (SEQ ID NO. 8), 16196 (SEQ ID NO. 9), 16197 (SEQ ID NO. 10), 16198 (SEQ ID NO. 11), 16199 (SEQ ID NO. 12), 16200 (SEQ ID NO. 13), 16201 (SEQ ID NO. 14), and 16202 (SEQ ID NO. 15) gave better than 50% inhibition of RhoA expression. Oligonucleotides 16195 (SEQ ID NO. 8), 16197 (SEQ ID NO. 10), 16199 (SEQ ID NO. 12), 16201 (SEQ ID NO. 14), and 16202 (SEQ ID NO. 15) gave better than 75% inhibition of RhoA expression.

TABLE 2

Activities of Phosphorothioate Oligonucleotides Targeted to Human RhoA

| ISIS No: | SEQ ID NO: | GENE TARGET REGION | % mRNA EXPRESSION | % mRNA INHIBITION |
|---|---|---|---|---|
| LIPOFECTIN only | — | — | 100.0% | 0.0% |
| 16191 | 4 | 5'-UTR | 66.4% | 33.6% |
| 16192 | 5 | AUG | 68.0% | 32.0% |
| 16193 | 6 | Coding | 31.9% | 68.1% |
| 16194 | 7 | Coding | 79.9% | 20.1% |
| 16195 | 8 | Coding | 3.9% | 96.1% |
| 16196 | 9 | Coding | 31.4% | 68.6% |
| 16197 | 10 | Coding | 19.2% | 81.8% |
| 16198 | 11 | Stop | 46.4% | 53.6% |
| 16199 | 12 | 3'-UTR | 22.9% | 77.1% |
| 16200 | 13 | 3'-UTR | 36.9% | 63.1% |
| 16201 | 14 | 3'-UTR | 22.0% | 78.0% |
| 16202 | 15 | 3'-UTR | 14.4% | 85.6% |
| 16203 | 16 | 3'-UTR | 88.0% | 12.0% |

TABLE 2-continued (merged above)

Example 3

Dose Response and Specificity of Antisense Oligonucleotide Effects on Human RhoA mRNA Levels in A549 Cells Three of the most active oligonucleotides from the initial screen were chosen for dose response assays. These include oligonucleotides 16195 (SEQ ID NO. 8), 16201 (SEQ ID NO. 14), and 16202 (SEQ ID NO. 15). A549 cells were grown, treated and processed as described in Example 2. LIPOFECTIN was added at a ratio of 2.5 mg/ml per 100 nM of oligonucleotide. The control included LIPOFECTIN at a concentration of 7.5 mg/ml. Results are shown in Table 3. Each oligonucleotide showed a dose response effect with in maximal inhibition greater than 90%.

The specificity of these oligonucleotides was investigated using scrambled controls, i.e. oligonucleotides with the same base composition and a scrambled sequence. Oligonucleotide 16915 (SEQ ID NO. 19) is a scrambled control for 16201 (SEQ ID NO. 14) and oligonucleotide 16913 (SEQ ID NO. 17) is a scrambled control for 16202 (SEQ ID NO. 15). Both antisense oligonucleotides showed a dose dependent effect on mRNA expression, while scrambled controls showed much less inhibition which was only seen at higher does.

TABLE 3

Dose Response of A549 Cells to RhoA Antisense Oligonucleotides (ASOs)

| ISIS # | SEQ ID NO: | ASO Gene Target | Dose | % mRNA Expression | % mRNA Inhibition |
|---|---|---|---|---|---|
| control | — | LIPOFECTIN only | — | 100.0% | 0.0% |
| 16195 | 8 | Coding | 75 nM | 72.7% | 27.3% |
| 16195 | 8 | " | 150 nM | 35.0% | 65.0% |
| 16195 | 8 | " | 300 nM | 20.3% | 79.7% |
| 16201 | 14 | 3'-UTR | 75 nM | 79.1% | 20.9% |
| 16201 | 14 | " | 150 nM | 35.7% | 64.3% |
| 16201 | 14 | " | 300 nM | 9.5% | 90.5% |
| 16202 | 15 | 3'-UTR | 75 nM | 68.7% | 31.3% |
| 16202 | 15 | " | 150 nM | 28.8% | 71.2% |
| 16202 | 15 | " | 300 nM | 6.1% | 93.7% |

TABLE 4

Specificity of RhoA Antisense Oligonucleotides (ASOs) in A549 Cells

| ISIS # | SEQ ID NO: | ASO Gene Target | Dose | % mRNA Expression | % mRNA Inhibition |
|---|---|---|---|---|---|
| control | — | LIPOFECTIN only | — | 100% | 0% |
| 16201 | 14 | 3'-UTR | 75 nM | 64.4% | 35.6% |
| 16201 | 14 | " | 150 nM | 35.3% | 64.7% |

TABLE 4-continued

Specificity of RhoA Antisense Oligonucleotides (ASOs) in A549 Cells

| ISIS # | SEQ ID NO: | ASO Gene Target | Dose | % mRNA Expression | % mRNA Inhibition |
|---|---|---|---|---|---|
| 16201 | 14 | " | 300 nM | 5.7% | 94.3% |
| 16915 | 19 | control | 75 nM | 89.9% | 10.1% |
| 16915 | 19 | " | 150 nM | 98.3% | 1.7% |
| 16915 | 19 | " | 300 nM | 84.8% | 15.2% |
| 16202 | 15 | 3'-UTR | 75 nM | 39.9% | 60.1% |
| 16202 | 15 | " | 150 nM | 20.2% | 79.8% |
| 16202 | 15 | " | 300 nM | 10.8% | 89.2% |
| 16913 | 17 | control | 75 nM | 97.6% | 2.4% |
| 16913 | 17 | " | 150 nM | 89.8% | 10.2% |
| 16913 | 17 | " | 300 nM | 55.6% | 44.4% |

Example 4
Design and Testing of Chimeric (Deoxy Gapped) 2'-O-methoxyethyl RhoA Antisense Oligonucleotides on RhoA Levels in A549 Cells Oligonucleotides having SEQ ID NO: 14 were synthesized as a uniformly phosphorothioate or mixed phosphorothioate/phosphodiester chimeric oligonucleotides having variable regions of 2'-O-methoxyethyl (2'-MOE) nucleotides and deoxynucleotides. All 2'-MOE cytosines were 5-methyl-cytosines. Additionally, some oligonucleotides were synthesized with deoxycytosines as 5-methyl-cytosines. Additional oligonucleotides were synthesized, with similar chemistries, as scrambled controls.

TABLE 6

Dose Response of A549 Cells to RhoA Antisense Gapmer Oligonucleotides (ASOs)

| ISIS # | SEQ ID NO: | ASO Gene Target | Dose | % mRNA Expression | % mRNA Inhibition |
|---|---|---|---|---|---|
| control | — | LIPOFECTIN only | — | 100% | 0% |
| 16201 | 14 | 3'-UTR | 75 nM | 119.5% | — |
| 16201 | 14 | " | 150 nM | 54.5% | 45.5% |
| 16201 | 14 | " | 300 nM | 39.5% | 60.5% |
| 17130 | 14 | 3'-UTR | 75 nM | 56.2% | 43.8% |
| 17130 | 14 | " | 150 nM | 31.5% | 68.5% |
| 17130 | 14 | " | 300 nM | 14.1% | 85.9% |
| 17131 | 14 | 3'-UTR | 75 nM | 55.5% | 44.5% |
| 17131 | 14 | " | 150 nM | 35.4% | 64.6% |
| 17131 | 14 | " | 300 nM | 24.7% | 75.3% |
| 17132 | 14 | 3'-UTR | 75 nM | 71.3% | 28.7% |
| 17132 | 14 | " | 150 nM | 31.3% | 68.7% |
| 17132 | 14 | " | 300 nM | 13.1% | 86.9% |
| 17133 | 14 | 3'-UTR | 75 nM | 41.7% | 58.3% |
| 17133 | 14 | " | 150 nM | 33.8% | 66.2% |
| 17133 | 14 | " | 300 nM | 14.4% | 85.6% |
| 17134 | 14 | 3'-UTR | 75 nM | 76.6% | 23.4% |
| 17134 | 14 | " | 150 nM | 35.9% | 64.1% |
| 17134 | 14 | " | 300 nM | 68.5% | 31.5% |

Example 5
Time Course of Antisense Oligonucleotide Effects on Human RhoA Protein Levels in A549 Cells Oligonucleotide 17131 was tested by treating for varying times and measuring the effect of the oligo on RhoA protein

TABLE 5

Nucleotide Sequences of 16201 Analogues

| ISIS NO. | NUCLEOTIDE SEQUENCE (5' -> 3')[1] | SEQ ID NO: | TARGET GENE NUCLEOTIDE CO-ORDINATES[2] | GENE TARGET REGION |
|---|---|---|---|---|
| 17130 | GsGsCsTsGsTsTsAsGsAsGsCsAsGsTsGsTsCsAsA | 14 | 0937–0956 | 3'-UTR |
| 17131 | GsGsCsTsGsTsTsAsGsAsGsCsAsGsTsGsTsCsAsA | 14 | 0937–0956 | 3'-UTR |
| 17132 | GsGsCsTsGsTsTsAsGsAsGsCsAsGsTsGsTsCsAsA | 14 | 0937–0956 | 3'-UTR |
| 17133 | GsGsCsTsGsTsTsAsGsAsGsCsAsGsTsGsTsCsAsA | 14 | 0937–0956 | 3'-UTR |
| 17134 | GsGsCsTsGsTsTsAsGsAsGsCsAsGsTsGsTsCsAsA | 14 | 0937–0956 | 3'-UTR |
| 17818 | GoGoCsTsGsTsTsAsGsAsGsCsAoGoToGoToCoAoA | 14 | 0937–0956 | all 5-meC |
| 17819 | ToGoCsGsGsTsAsAsGsTsGsCsGoGoToAoToCoAoA | 19 | 16201 control | all 5-meC |
| 18550 | TsGsCsGsGsTsAsAsGsTsGsCsGsGsTsAsTsCsAsA | 19 | 16201 control | |
| 20459 | GsGsCsTsGsTsTsAsGsAsGsCsAsGsTsGsTsCsAsA | 14 | 0937–0956 | all 5-meC |
| 21919 | GsTsCsGsTsTsAsGsTsCsGsAsAsAsTsGsAsGsGsC | 20 | 16201 control | |
| 21920 | AsGsCsTsGsTsGsAsAsCsGsAsGsTsGsTsCsGsA | 21 | 16201 control | |
| 21921 | TsGsCsAsGsTsTsGsGsCsAsGsAsGsTsCsTsGsAsA | 22 | 16201 control | |

[1] Emboldened residues are 2'-methoxyethoxy residues (others are 2'-deoxy). All 2'-methoxyethoxy cytidines are 5-methyl-cytidines; where indicated "all 5-meC", 2'-deoxycytidines are also 5-methyl-cytidines; "s" linkages are phosphorothioate linkages, "o" linkages are phosphodiester linkages.
[2] Co-ordinates from Genbank Accession No. X05026, locus name "HSRHOB" SEQ ID NO. 1.

Dose response experiments were performed using chimeric oligonucleotides as discussed in Example 3. Results are shown in Table 6. The introduction of 2'-MOE nucleotides into the sequence improved the maximum inhibition from 60%, with a phosphorothioate oligodeoxynucleotide, to greater than 75%. The exception was the fully modified 2-MOE oligonucleotide which was less effective than the oligodeoxynucleotide.

levels. A549 cells were grown and treated with oligonucleotide (300 nM) as described in Example 2. Cells were harvested at 24, 48 and 72 hours after treatment. RhoA protein levels were measured by Western blotting. After oligonucleotide treatment, cells were washed twice in phosphate-buffered saline (PBS) and lysed in 25 mM Tris-HCl pH 7.5, 1% Triton X-100, 0.2% SDS, 0.5% sodium deoxycholate, 450 mM NaCl, and 10 mg/ml aprotinin and leupeptin. After 15 minutes on ice, the samples were centrifuged at maximum speed in a microfuge. Protein concentration was determined by Bradford reagent (Bio-Rad Laboratories, Hercules, Calif.). Fifty mg of protein was separated by SDS-PAGE (15%). Following electrophoresis, proteins were transferred to IMMOBILON-P membranes (Millipore, Bedford, Mass.) The membrane was blocked in 5% fish gelatin (Sigma Chemicals, St. Louis, Mo.) and RhoA specific antibodies were used to visualize the proteins. After incubation with the appropriate secondary antibody, proteins were visualized using either LUMIGLO Reagent (New England Biolabs, Beverly, Mass.) or ECL PLUS (Amersham Pharmacia Biotech, Piscataway, N.J.). Inhibition of RhoA protein was observable after 24 hours. After 48 hours, RhoA protein concentration was reduced by 80% using 17131 (SEQ ID NO. 14). Minimal inhibition was seen with 17163 (SEQ ID NO. 190), an oligonucleotide targeted to Rac1. Results are shown in Table 7.

TABLE 7

Time course of RhoA Antisense Oligonucleotides (ASOs) in A549 Cells

| ISIS # | SEQ ID NO: | ASO Gene Target | Time after treatmt | % protein Expression | % protein Inhibition |
|---|---|---|---|---|---|
| control | — | LIPOFECTIN only | — | 100% | 0% |
| 17131 | 14 | 3'-UTR | 24 hr | 46.2% | 53.8% |
| 17131 | 14 | " | 48 hr | 16.0% | 84.0% |
| 17131 | 14 | " | 72 hr | 12.4% | 87.6% |
| 17163 | 190 | Rac1 control | 24 hr | 104.1% | — |
| 17163 | 190 | " | 48 hr | 82.3% | 17.7% |
| 17163 | 190 | " | 72 hr | 95.2% | 4.8% |

Example 6
Dose Response of Antisense Oligonucleotide Effects on Human RhoA Protein Levels in A549 Cells Oligonucleotide 17131 was tested for a dose response by using varying concentrations of oligonucleotide and measuring the effect of the oligonucleotide on RhoA protein levels. A549 cells were grown and treated with oligonucleotide (concentrations indicated in Table 8) as described in Example 2. Western blotting was performed to measure protein levels as described in Example 5. A dose response effect is seen with 17131 (SEQ ID NO. 14), whereas the scrambled control 18550 (SEQ ID NO. 19) had no effect on RhoA protein levels.

TABLE 8

Dose response of RhoA antisense oligonucleotide on protein levels in A549 cells

| ISIS # | SEQ ID NO: | ASO Gene Target | Dose | % protein Expression | % protein Inhibition |
|---|---|---|---|---|---|
| control | — | LIPOFECTIN only | — | 100% | 0% |
| 17131 | 14 | 3'-UTR | 75 nM | 51% | 49% |
| 17131 | 14 | " | 150 nM | 23% | 77% |
| 17131 | 14 | " | 300 nM | 20% | 80% |
| 18550 | 19 | control | 75 nM | 101% | — |
| 18550 | 19 | " | 150 nM | 101% | — |
| 18550 | 19 | " | 300 nM | 104% | — |

Example 7
Inhibition of JNK Activation by RhoA Antisense Oligonucleotides in A549 Cells Stimulated with $H_2O_2$ Oligonucleotide 17131 (SEQ ID NO. 14) was tested for its ability to inhibit JNK activation by stimulation with $H_2O_2$ or Il-1b. A549 cells were grown as described in Example 2. Cells were treated with 150 nM of oligonucleotide for four hours. After treatment, the media was replaced with DMEM, 0.1% FCS, and the cells were left in culture for 48 hours prior to stimulation. Stimulation was with either 30 ng/ml IL-1b or 1 mM $H_2O_2$ for 30 minutes. After stimulation, the cells were washed twice in PBS, and lysed in 25 mM Hepes pH 7.7, 0.3 M NaCl, 1.5 mM $MgCl_2$, 0.1% Triton X-100, 20 mM b-glycerophosphate, 0.1 mM sodium orthovanadate ($Na_3VO_4$), 0.5 mM PMSF, and 10 mg/ml of aprotinin and leupeptin. After 20 minutes on ice, the lysates were centrifuged at maximum speed in a microfuge for 20 minutes. The protein concentration in the supernatant was determined using Bradford reagent (Bio-Rad Laboratories, Hercules, Calif.). To 150 mg of protein, 25 ml of c-Jun fusion beads (New England Biolabs, Beverly, Mass.) were added and incubated at 4° C. on a rotating wheel overnight. The samples were then washed four times in 20 mM Hepes pH 7.7, 50 mM NaCl, 0.1 mM EDTA, 2.5 mM $MgCl_2$, and 0.05% Triton X-100 (HIBI buffer). The kinase reaction was run for 20 minutes at 30° C. in 20 mM Hepes pH 7.7, 20 mM $MgCl_2$, 20 mM b-glycerophosphate, 20 mM p-nitrophenyl phosphate, 0.1 mM $Na_3VO_4$, 2 mM DTT, 20 mM ATP, and 5 mCi of $g[^{32}P]$-ATP. The reaction was stopped with 500 ml of ice cold HIBI buffer. The beads were pelleted, resuspended in PAGE loading buffer, boiled for 5 minutes, and the products separated on a 12% SDS gel (Novex, La Jolla, Calif.). Bands were quantitated using a PhosphorImager.

Results are shown in Table 9. Oligonucleotide 17131 (SEQ ID NO. 14) showed moderate but specific inhibition of $H_2O_2$-induced JNK activation.

TABLE 9

Inhibition of JNK activation by RhoA antisense oligonucleotides

| ISIS # | SEQ ID NO: | ASO Gene Target | Dose | % inhibition Il-1b induced | % inhibition $H_2O_2$ induced |
|---|---|---|---|---|---|
| control | — | LIPOFECTIN only | — | 0% | 0% |
| 17131 | 14 | 3'-UTR | 150 nM | — | 37.6% |
| 18550 | 19 | control | 150 nM | 2.2% | 5.8% |

Example 8
Synthesis of Additional RhoA Sequences

Additional oligonucleotides were synthesized in 96 well plate format via solid phase P(III) phosphoramidite chemistry on an automated synthesizer capable of assembling 96 sequences simultaneously in a standard 96 well format. Phosphodiester internucleotide linkages were afforded by oxidation with aqueous iodine. Phosphorothioate internucleotide linkages were generated by sulfurization utilizing 3,H-1,2 benzodithiole-3-one 1,1 dioxide (Beaucage Reagent) in anhydrous acetonitrile-. Standard base-protected beta-cyanoethyl-di-isopropyl phosphoramidites were purchased from commercial vendors (e.g. PE-Applied Biosystems, Foster City, Calif., or Pharmacia, Piscataway, N.J.) Non-standard nucleosides are synthesized as per published methods. They are utilized as base protected beta-cyanoethyldiisopropyl phosphoramidites.

Oligonucleotides were cleaved from support and deprotected with concentrated $NH_4OH$ at elevated temperature (55–60° C.) for 12–16 hours and the released product then dried in vacuo. The dried product was then re-suspended in sterile water to afford a master plate from which all analytical and test plate samples are then diluted utilizing robotic pipettors.

A series of oligonucleotides were designed to target different regions of the human RhoA RNA, using published sequences (GenBank accession number X05026, incorporated herein as SEQ ID NO: 1). The oligonucleotides are shown in Table 10. Target sites are indicated by nucleotide numbers, as given in the sequence source reference (Genbank accession no. X05026), to which the oligonucleotide binds.

All compounds in Table 10 are oligodeoxynucleotides with phosphorothioate backbones (internucleoside linkages) throughout. All compounds in Table 11 are chimeric oligonucleotides ("gapmers") 18 nucleotides in length, composed of a central "gap" region consisting of ten 2'-deoxynucleotides, which is flanked on both sides (5' and 3' directions) by four-nucleotide "wings." The wings are composed of 2'-methoxyethyl (2'-MOE)nucleotides. The internucleoside (backbone) linkages are phosphorothioate (P=S) throughout the oligonucleotide. Cytidine residues in the 2'-MOE wings are 5-methylcytidines.

seconds. 1 mL of Buffer RPE was then added to each well of the RNEASY 96 plate and the vacuum applied for a period of 15 seconds. The Buffer RPE wash was then repeated and the vacuum was applied for an additional 10 minutes. The plate was then removed from the QIAVAC manifold and blotted dry on paper towels. The plate was then re-attached to the QIAVAC manifold fitted with a collection tube rack containing 1.2 mL collection tubes. RNA was then eluted by pipetting 60 μL water into each well, incubating 1 minute, and then applying the vacuum for 30 seconds. The elution step was repeated with an additional 60 μL water.

Poly(A)+ mRNA may be isolated according to Miura et al., Clin. Chem., 42, 1758 (1996). other methods for poly (A)+ mRNA isolation are taught in, for example, Ausubel, F. M. et al., Current Protocols in Molecular Biology, Volume 1, pp. 4.5.1–4.5.3, John Wiley & Sons, Inc., (1993). Briefly, for cells grown on 96-well plates, growth medium was removed from the cells and each well was washed with 200 ml cold PBS. 60 ml lysis buffer (10 mM Tris-HCl, pH 7.6, 1 mM

TABLE 10

Nucleotide Sequences of Human RhoA Phosphorothioate Oligodeoxynucleotides

| ISIS NO. | NUCLEOTIDE SEQUENCE (5' -> 3') | SEQ ID NO: | TARGET GENE NUCLEOTIDE CO-ORDINATES[1] | GENE TARGET REGION |
|---|---|---|---|---|
| 25544 | AGAGAACCGACGGAGGAC | 23 | 0030–0047 | 5'-UTR |
| 25545 | GTGGACTAATGAGAGAAC | 24 | 0041–0058 | 5'-UTR |
| 25546 | GACCGTGGACTAATGAGA | 25 | 0045–0062 | 5'-UTR |
| 25547 | AGCTGAAGACCAGACCGT | 26 | 0057–0074 | 5'-UTR |
| 25548 | AGTCGCAAACTCGGAGAC | 4 | 0085–0102 | 5'-UTR |
| 25549 | AATCCGAGTCCAGCCTCT | 27 | 0128–0145 | 5'-UTR |
| 25550 | AACGAATCCGAGTCCAGC | 28 | 0132–0149 | 5'-UTR |
| 25551 | TCAGGCAACGAATCCGAG | 29 | 0138–0155 | 5'-UTR |
| 25552 | CACCAACAATCACCAGTT | 30 | 0178–0195 | Coding |
| 25553 | AAGACTATGAGCAAGCAT | 31 | 0215–0232 | Coding |
| 25554 | ATACACCTCTGGGAACTG | 32 | 0243–0260 | Coding |
| 25555 | ACATAGTTCTCAAACACT | 33 | 0269–0286 | Coding |
| 25556 | ACTCTACCTGCTTTCCAT | 34 | 0304–0321 | Coding |
| 25557 | CACAAAGCCAACTCTACC | 35 | 0314–0331 | Coding |
| 25558 | AACATCGGTATCTGGGTA | 36 | 0378–0395 | Coding |
| 25559 | TTCTGGGATGTTTTCTAA | 37 | 0432–0449 | Coding |
| 25560 | GGACAGAAATGCTTGACT | 38 | 0464–0481 | Coding |
| 25561 | GTGCTCATCATTCCGAAG | 39 | 0519–0536 | Coding |
| 25562 | CTTGTGTGCTCATCATTC | 40 | 0524–0541 | Coding |
| 25563 | TAGCTCCCGCCTTGTGTG | 41 | 0534–0551 | Coding |
| 25564 | CCAATCCTGTTTGCCATA | 42 | 0596–0613 | Coding |
| 25565 | GTCTTTGCTGAACACTCC | 43 | 0629–0646 | Coding |
| 25566 | AAAACCTCTCTCACTCCA | 44 | 0653–0670 | Coding |
| 25567 | AAGACAAGGCAACCAGAT | 45 | 0719–0736 | Coding |
| 25568 | TTTCACAAGACAAGGCAA | 46 | 0725–0742 | Stop |

Example 9
Total RNA Isolation

Total mRNA was isolated using an RNEASY 96 kit and buffers purchased from Qiagen Inc. (Valencia Calif.) following the manufacturer's recommended procedures. Briefly, for cells grown on 96-well plates, growth medium was removed from the cells and each well was washed with 200 μL cold PBS. 100 μL Buffer RLT was added to each well and the plate vigorously agitated for 20 seconds. 100 μL of 70% ethanol was then added to each well and the contents mixed by pippeting three times up and down. The samples were then transferred to the RNEASY 96 well plate attached to a QIAVAC manifold fitted with a waste collection tray and attached to a vacuum source. Vacuum was applied for 15 seconds. 1 mL of Buffer RW1 was added to each well of the RNEASY 96 plate and the vacuum again applied for 15

EDTA, 0.5 M NaCl, 0.5% NP-40, 20 mM vanadyl-ribonucleoside complex) was added to each well, the plate was gently agitated and then incubated at room temperature for five minutes. 55 ml of lysate was transferred to Oligo d(T) coated 96-well plates (AGCT Inc., Irvine Calif.). Plates were incubated for 60 minutes at room temperature, washed 3 times with 200 ml of wash buffer (10 mM Tris-HCl pH 7.6, 1 mM EDTA, 0.3 M NaCl). After the final wash, the plate was blotted on paper towels to remove excess wash buffer and then air-dried for 5 minutes. 60 ml of elution buffer (5 mM Tris-HCl pH 7.6), preheated to 70° C. was added to each well, the plate was incubated on a 90° hot plate for 5 minutes, and the eluate was then transferred to a fresh 96-well plate.

Cells grown on 100 mm or other standard plates may be treated similarly, using appropriate volumes of all solutions.

Example 10
Real-time Quantitative PCR Analysis of RhoA mRNA Levels

Quantitation of RhoA mRNA levels was determined by real-time quantitative PCR using the ABI PRISM 7700 Sequence Detection System (PE-Applied Biosystems, Foster City, Calif.) according to manufacturer's instructions. This is a closed-tube, non-gel-based, fluorescence detection system which allows high-throughput quantitation of polymerase chain reaction (PCR) products in real-time. As opposed to standard PCR, in which amplification products are quantitated after the PCR is completed, products in real-time quantitative PCR are quantitated as they accumulate. This is accomplished by including in the PCR reaction an oligonucleotide probe that anneals specifically between the forward and reverse PCR primers, and contains two fluorescent dyes. A reporter dye (e.g., JOE or FAM, obtained from either Operon Technologies Inc., Alameda, Calif. or PE-Applied Biosystems, Foster City, Calif.) is attached to the 5' end of the probe and a quencher dye (e.g., TAMRA, obtained from either Operon Technologies Inc., Alameda, Calif. or PE-Applied Biosystems, Foster City, Calif.) is attached to the 3' end of the probe. When the probe and dyes are intact, reporter dye emission is quenched by the proximity of the 3' quencher dye. During amplification, annealing of the probe to the target sequence creates a substrate that can be cleaved by the 5'-exonuclease activity of Taq polymerase. During the extension phase of the PCR amplification cycle, cleavage of the probe by Taq polymerase releases the reporter dye from the remainder of the probe (and hence from the quencher moiety) and a sequence-specific fluorescent signal is generated. With each cycle, additional reporter dye molecules are cleaved from their respective probes, and the fluorescence intensity is monitored at regular (six-second) intervals by laser optics built into the ABI PRISM 7700 Sequence Detection System. In each assay, a series of parallel reactions containing serial dilutions of mRNA from untreated control samples generates a standard curve that is used to quantitate the percent inhibition after antisense oligonucleotide treatment of test samples.

PCR reagents were obtained from PE-Applied Biosystems, Foster City, Calif. RT-PCR reactions were carried out by adding 25 μL PCR cocktail (1x TAQMAN buffer A, 5.5 mM MgCl$_2$, 300 μM each of dATP, dCTP and dGTP, 600 μM of dUTP, 100 nM each of forward primer, reverse primer, and probe, 20 Units RNAse inhibitor, 1.25 Units AMPLITAQ GOLD, and 12.5 Units MuLV reverse transcriptase) to 96 well plates containing 25 μL poly(A) mRNA solution. The RT reaction was carried out by incubation for 30 minutes at 48° C. Following a 10 minute incubation at 95° C. to activate the AMPLITAQ GOLD, 40 cycles of a two-step PCR protocol were carried out: 95° C. for 15 seconds (denaturation) followed by 60° C. for 1.5 minutes (annealing/extension). RhoA probes and primers were designed to hybridize to the human RhoA sequence, using published sequence information (GenBank accession number X05026, incorporated herein as SEQ ID NO:1).

For RhoA the PCR primers were:
forward primer: GGCTGGACTCGGATTCGTT (SEQ ID NO: 62)
reverse primer: CCATCACCAACAATCACCAGTT (SEQ ID NO: 63) and the
PCR probe was: FAM-CCTGAGCAATGGCTGCCATCCG-TAMRA (SEQ ID NO: 64) where FAM (PE-Applied Biosystems, Foster City, Calif.) is the fluorescent reporter dye) and TAMRA (PE-Applied Biosystems, Foster City, Calif.) is the quencher dye.

For GAPDH the PCR primers were:
forward primer: GAAGGTGAAGGTCGGAGTC (SEQ ID NO: 65)
reverse primer: GAAGATGGTGATGGGATTTC (SEQ ID NO: 66)and the
PCR probe was: 5' JOE-CAAGCTTCCCGTTCTCAGCC-TAMRA 3' (SEQ ID NO: 67) where JOE (PE-Applied Biosystems, Foster City, Calif.) is the fluorescent reporter dye) and TAMRA (PE-Applied Biosystems, Foster City, Calif.) is the quencher dye.

Example 11
Antisense Inhibition of RhoA Expression-phosphorothioate Oligodeoxynucleotides In accordance with the present invention, a series of oligonucleotides were designed to target different regions of the human RhoA RNA, using published sequences (GenBank accession number X05026, incorporated herein as SEQ ID NO: 1). The oligonucleotides are shown in Table 10. Target sites are indicated by nucleotide numbers, as given in the sequence source reference (Genbank accession no. X05026), to which the oligonucleotide binds. All compounds in Table 10 are oligodeoxynucleotides with phosphorothioate backbones (internucleoside linkages) throughout. The compounds were analyzed for effect on RhoA mRNA levels by quantitative real-time PCR as described in other examples herein. Data are shown in Table 11 and are averages from three experiments. If present, "N.D." indicates "no data".

TABLE 11

Inhibition of RhoA mRNA levels by phosphorothioate oligodeoxynucleotides

| ISIS # | REGION | TARGET SITE | SEQUENCE | % Inhibition | SEQ ID NO. |
|---|---|---|---|---|---|
| 25544 | 5' UTR | 30 | AGAGAACCGACGGAGGAC | 47 | 23 |
| 25545 | 5' UTR | 41 | GTGGACTAATGAGAGAAC | 0 | 24 |
| 25546 | 5' UTR | 45 | GACCGTGGACTAATGAGA | 40 | 25 |
| 25547 | 5' UTR | 57 | AGCTGAAGACCAGACCGT | 76 | 26 |
| 25548 | 5' UTR | 85 | AGTCGCAAACTCGGAGAC | 36 | 4 |
| 25549 | 5' UTR | 128 | AATCCGAGTCCAGCCTCT | 67 | 27 |
| 25550 | 5' UTR | 132 | AACGAATCCGAGTCCAGC | 34 | 28 |
| 25551 | 5' UTR | 138 | TCAGGCAACGAATCCGAG | 59 | 29 |
| 25552 | CODING | 178 | CACCAACAATCACCAGTT | 47 | 30 |
| 25553 | CODING | 215 | AAGACTATGAGCAAGCAT | 36 | 31 |
| 25554 | CODING | 243 | ATACACCTCTGGGAACTG | 74 | 32 |
| 25555 | CODING | 269 | ACATAGTTCTCAAACACT | 31 | 33 |
| 25556 | CODING | 304 | ACTCTACCTGCTTTCCAT | 64 | 34 |
| 25557 | CODING | 314 | CACAAAGCCAACTCTACC | 25 | 35 |
| 25558 | CODING | 378 | AACATCGGTATCTGGGTA | 35 | 36 |
| 25559 | CODING | 432 | TTCTGGGATGTTTTCTAA | 21 | 37 |
| 25560 | CODING | 464 | GGACAGAAATGCTTGACT | 64 | 38 |
| 25561 | CODING | 519 | GTGCTCATCATTCCGAAG | 71 | 39 |
| 25562 | CODING | 524 | CTTGTGTGCTCATCATTC | 38 | 40 |
| 25563 | CODING | 534 | TAGCTCCCGCCTTGTGTG | 78 | 41 |
| 25564 | CODING | 596 | CCAATCCTGTTTGCCATA | 82 | 42 |
| 25565 | CODING | 629 | GTCTTTGCTGAACACTCC | 56 | 43 |
| 25566 | CODING | 653 | AAAACCTCTCTCACTCCA | 68 | 44 |
| 25567 | CODING | 719 | AAGACAAGGCAACCAGAT | 55 | 45 |
| 25568 | STOP | 725 | TTTCACAAGACAAGGCAA | 0 | 46 |
| 25569 | STOP | 731 | GCAAGGTTTCACAAGACA | 37 | 47 |
| 25570 | 3' UTR | 758 | ATTAACCGCATAAGGGCT | 77 | 48 |
| 25571 | 3' UTR | 777 | TAATAAACAGCACTTCAA | 19 | 49 |
| 25572 | 3' UTR | 798 | CCAGTAATCATACACTAA | 26 | 50 |
| 25573 | 3' UTR | 847 | ATGACTTCTGATTTGTAA | 27 | 51 |
| 25574 | 3' UTR | 854 | TAGCAAGATGACTTCTGA | 62 | 52 |
| 25575 | 3' UTR | 858 | CTGGTAGCAAGATGACTT | 59 | 53 |
| 25576 | 3' UTR | 865 | CTAAATACTGGTAGCAAG | 29 | 54 |
| 25577 | 3' UTR | 872 | TTGGCTTCTAAATACTGG | 57 | 55 |
| 25578 | 3' UTR | 878 | TCATAGTTGGCTTCTAAA | 60 | 56 |

TABLE 11-continued

Inhibition of RhoA mRNA levels by phosphorothioate oligodeoxynucleotides

| ISIS # | REGION | TARGET SITE | SEQUENCE | % Inhibition | SEQ ID NO. |
|---|---|---|---|---|---|
| 25579 | 3' UTR | 883 | AATAATCATAGTTGGCTT | 33 | 57 |
| 25580 | 3' UTR | 923 | TCAAAAGGACCCTGGTGG | 25 | 58 |
| 25581 | 3' UTR | 950 | GTGCAGAGGAGGGCTGTT | 68 | 59 |
| 25582 | 3' UTR | 1026 | CCAACTGTTTCTCTTTCT | 52 | 60 |
| 25583 | 3' UTR | 1056 | AAGTAGTTACAGCCTAAT | 26 | 61 |

As shown in Table 11, SEQ ID NOs 23, 26, 27, 29, 30, 32, 34, 38, 39, 41, 42, 43, 44, 45, 48, 52, 53, 56, 57, 59 and 60 demonstrated at least 45% inhibition of RhoA expression in this assay and are therefore preferred.

Example 12
Antisense Inhibition of RhoA Expression-phosphorothioate 2'-MOE gapmer Oligonucleotides In accordance with the present invention, a second series of oligonucleotides targeted to human RhoA were synthesized. The oligonucleotide sequences are shown in Table 12. Target sites are indicated by nucleotide numbers, as given in the sequence source reference (Genbank accession no. X05026), to which the oligonucleotide binds.

All compounds in Table 12 are chimeric oligonucleotides ("gapmers") 18 nucleotides in length, composed of a central "gap" region consisting of ten 2'-deoxynucleotides, which is flanked on both sides (5' and 3' directions) by four-nucleotide "wings". The wings are composed of 2'-methoxyethyl (2'-MOE)nucleotides. The internucleoside (backbone) linkages are phosphorothioate (P=S) throughout the oligonucleotide. Cytidine residues in the 2'-MOE wings are 5-methylcytidines.

TABLE 12

Nucleotide Sequences of Human RhoA Gapmer oligonucleotides

| ISIS NO. | NUCLEOTIDE SEQUENCE (5' - >3') | TARGET GENE SEQ NUCLEOTIDE ID CO- NO: ORDINATES[1] | GENE TARGET REGION |
|---|---|---|---|
| 25584 | AGAGAACCGACGGAGGAC | 23 0030-0047 | 5'-UTR |
| 25585 | GTGGACTAATGAGAGAAC | 24 0041-0058 | 5'-UTR |
| 25586 | GACCGTGGACTAATGAGA | 25 0045-0062 | 5'-UTR |
| 25587 | AGCTGAAGACCAGACCGT | 26 0057-0074 | 5'-UTR |
| 25588 | AGTCGCAAACTCGGAGAC | 4 0085-0102 | 5'-UTR |
| 25589 | AATCCGAGTCCAGCCTCT | 27 0128-0145 | 5'-UTR |
| 25590 | AACGAATCCGAGTCCAGC | 28 0132-0149 | 5'-UTR |
| 25591 | TCAGGCAACGAATCCGAG | 29 0138-0155 | 5'-UTR |
| 25592 | CACCAACAATCACCAGTT | 30 0178-0195 | Coding |
| 25593 | AAGACTATGAGCAAGCAT | 31 0215-0232 | Coding |
| 25594 | ATACACCTCTGGGAACTG | 32 0243-0260 | Coding |
| 25595 | ACATAGTTCTCAAACACT | 33 0269-0286 | Coding |
| 25596 | ACTCTACCTGCTTTCCAT | 34 0304-0321 | Coding |
| 25597 | CACAAAGCCAACTCTACC | 35 0314-0331 | Coding |
| 25598 | AACATCGGTATCTGGGTA | 36 0378-0395 | Coding |
| 25599 | TTCTGGGATGTTTTCTAA | 37 0432-0449 | Coding |
| 25600 | GGACAGAAATGCTTGACT | 38 0464-0481 | Coding |
| 25601 | GTGCTCATCATTCCGAAG | 39 0519-0536 | Coding |
| 25602 | CTTGTGTGCTCATCATTC | 40 0524-0541 | Coding |
| 25603 | TAGCTCCCGCCTTGTGTG | 41 0534-0551 | Coding |
| 25604 | CCAATCCTGTTTGCCATA | 42 0596-0613 | Coding |
| 25605 | GTCTTTGCTGAACACTCC | 43 0629-0646 | Coding |
| 25606 | AAAACCTCTCTCACTCCA | 44 0653-0670 | Coding |
| 25607 | AAGACAAGGCAACCAGAT | 45 0719-0736 | Coding |
| 25608 | TTTCACAAGACAAGGCAA | 46 0725-0742 | Stop |
| 25609 | GCAAGGTTTCACAAGACA | 47 0731-0748 | Stop |
| 25610 | ATTAACCGCATAAGGGCT | 48 0758-0775 | 3'-UTR |
| 25611 | TAATAAACAGCACTTCAA | 49 0777-0794 | 3'-UTR |
| 25612 | CCAGTAATCATACACTAA | 50 0798-0815 | 3'-UTR |
| 25613 | ATGACTTCTGATTTGTAA | 51 0847-0864 | 3'-UTR |
| 25614 | TAGCAAGATGACTTCTGA | 52 0854-0871 | 3'-UTR |
| 25615 | CTGGTAGCAAGATGACTT | 53 0858-0875 | 3'-UTR |
| 25616 | CTAAATACTGGTAGCAAG | 54 0865-0882 | 3'-UTR |
| 25617 | TTGGCTTCTAAATACTGG | 55 0872-0889 | 3'-UTR |
| 25618 | TCATAGTTGGCTTCTAAA | 56 0878-0895 | 3'-UTR |
| 25619 | AATAATCATAGTTGGCTT | 57 0883-0900 | 3'-UTR |
| 25620 | TCAAAAGGACCCTGGTGG | 58 0923-0940 | 3'-UTR |
| 25621 | GTGCAGAGGAGGGCTGTT | 59 0950-0967 | 3'-UTR |
| 25622 | CCAACTGTTTCTCTTTCT | 60 1026-1043 | 3'-UTR |
| 25623 | AAGTAGTTACAGCCTAAT | 61 1056-1073 | 3'-UTR |

[1]Emboldened residues are 2'-methoxyethoxy residues (others are 2'-deoxy-). All 2'-methoxyethoxy cytidines and cytidines are 5-methyl-cytidines; all linkages are phosphorothioate linkages.
[2]Co-ordinates from Genbank Accession No. X05026, locus name "HSRHOB" SEQ ID NO. 1.

The oligonucleotides shown in Table 12 were tested by real-time quantitative PCR as described in other examples herein and data are shown in Table 13 (average from three experiments). If present, "N.D." indicated "no data".

TABLE 13

Inhibition of RhoA mRNA levels by chimeric phosphorothioate oligonucleotides having 2'-MOE wings and a deoxy gap

| ISIS # | REGION | TARGET SITE | SEQUENCE | % Inhibition | SEQ ID NO. |
|---|---|---|---|---|---|
| 25584 | 5' UTR | 30 | AGAGAACCGACGGAGGAC | 44 | 23 |
| 25585 | 5' UTR | 41 | GTGGACTAATGAGAGAAC | 35 | 24 |
| 25586 | 5' UTR | 45 | GACCGTGGACTAATGAGA | 53 | 25 |
| 25587 | 5' UTR | 57 | AGCTGAAGACCAGACCGT | 62 | 26 |
| 25588 | 5' UTR | 85 | AGTCGCAAACTCGGAGAC | 54 | 4 |
| 25589 | 5' UTR | 128 | AATCCGAGTCCAGCCTCT | 38 | 27 |
| 25590 | 5' UTR | 132 | AACGAATCCGAGTCCAGC | 47 | 28 |
| 25591 | 5' UTR | 138 | TCAGGCAACGAATCCGAG | 31 | 29 |
| 25592 | CODING | 178 | CACCAACAATCACCAGTT | 0 | 30 |
| 25593 | CODING | 215 | AAGACTATGAGCAAGCAT | 43 | 31 |
| 25594 | CODING | 243 | ATACACCTCTGGGAACTG | 23 | 32 |
| 25595 | CODING | 269 | ACATAGTTCTCAAACACT | 16 | 33 |
| 25596 | CODING | 304 | ACTCTACCTGCTTTCCAT | 0 | 34 |
| 25597 | CODING | 314 | CACAAAGCCAACTCTACC | 0 | 35 |
| 25598 | CODING | 378 | AACATCGGTATCTGGGTA | 65 | 36 |
| 25599 | CODING | 432 | TTCTGGGATGTTTTCTAA | 53 | 37 |
| 25600 | CODING | 464 | GGACAGAAATGCTTGACT | 50 | 38 |
| 25601 | CODING | 519 | GTGCTCATCATTCCGAAG | 45 | 39 |
| 25602 | CODING | 524 | CTTGTGTGCTCATCATTC | 26 | 40 |
| 25603 | CODING | 534 | TAGCTCCCGCCTTGTGTG | 59 | 41 |
| 25604 | CODING | 596 | CCAATCCTGTTTGCCATA | 40 | 42 |
| 25605 | CODING | 629 | GTCTTTGCTGAACACTCC | 47 | 43 |
| 25606 | CODING | 653 | AAAACCTCTCTCACTCCA | 30 | 44 |
| 25607 | CODING | 719 | AAGACAAGGCAACCAGAT | 0 | 45 |
| 25608 | STOP | 725 | TTTCACAAGACAAGGCAA | 7 | 46 |
| 25609 | STOP | 731 | GCAAGGTTTCACAAGACA | 53 | 47 |
| 25610 | 3' UTR | 758 | ATTAACCGCATAAGGGCT | 56 | 48 |
| 25611 | 3' UTR | 777 | TAATAAACAGCACTTCAA | 7 | 49 |
| 25612 | 3' UTR | 798 | CCAGTAATCATACACTAA | 41 | 50 |
| 25613 | 3' UTR | 847 | ATGACTTCTGATTTGTAA | 53 | 51 |
| 25614 | 3' UTR | 854 | TAGCAAGATGACTTCTGA | 59 | 52 |
| 25615 | 3' UTR | 858 | CTGGTAGCAAGATGACTT | 67 | 53 |

TABLE 13-continued

Inhibition of RhoA mRNA levels by chimeric phosphorothioate oligonucleotides having 2'-MOE wings and a deoxy gap

| ISIS # | REGION | TARGET SITE | SEQUENCE | % Inhibition | SEQ ID NO. |
|---|---|---|---|---|---|
| 25616 | 3' UTR | 865 | CTAAATACTGGTAGCAAG | 65 | 54 |
| 25617 | 3' UTR | 872 | TTGGCTTCTAAATACTGG | 74 | 55 |
| 25618 | 3' UTR | 878 | TCATAGTTGGCTTCTAAA | 52 | 56 |
| 25619 | 3' UTR | 883 | AATAATCATAGTTGGCTT | 49 | 57 |
| 25620 | 3' UTR | 923 | TCAAAAGGACCCTGGTGG | 58 | 58 |
| 25621 | 3' UTR | 950 | GTGCAGAGGAGGGCTGTT | 60 | 59 |
| 25622 | 3' UTR | 1026 | CCAACTGTTTCTCTTTCT | 62 | 60 |
| 25623 | 3' UTR | 1056 | AAGTAGTTACAGCCTAAT | 44 | 61 |

As shown in Table 13, SEQ ID NOs 23, 24, 25, 26, 4, 27, 28, 31, 36, 37, 38, 39, 41, 42, 43, 47, 48, 50, 51, 52, 53, 54, 55, 56, 57, 58, 59, 60 and 61 demonstrated at least 35% inhibition of RhoA expression in this experiment and are therefore preferred.

Example 13
Synthesis of RhoB Antisense Oligonucleotide Sequences

Oligonucleotide sequences were synthesized as described in previous examples. Antisense oligonucleotides were designed to target human RhoB. Target sequence data are from the RhoB cDNA sequence published by Chardin, P., et al. (*Nucleic Acids Res.*, 1988, 16, 2717); Genbank accession number X06820, provided herein as SEQ ID NO: 68.

TABLE 14

Nucleotide Sequences of Human RhoB Phosphorothioate Oligodeoxynucleotides

| ISIS NO. | NUCLEOTIDE SEQUENCE (5' - >3') | SEQ ID NO: | TARGET GENE NUCLEOTIDE CO-ORDINATES[1] | GENE TARGET REGION |
|---|---|---|---|---|
| 25384 | CCACCACCAGCTTCTTGC | 69 | 0014-0031 | Coding |
| 25385 | CCGTCGCCCACCACCACC | 70 | 0024-0041 | Coding |
| 25386 | GCACGTCTTGCCACACGC | 71 | 0043-0060 | Coding |
| 25387 | ACTGAACACGATCAGCAG | 72 | 0061-0078 | Coding |
| 25388 | TTACTGAACACGATCAGC | 73 | 0063-0080 | Coding |
| 25389 | CCTTACTGAACACGATCA | 74 | 0065-0082 | Coding |
| 25390 | GTCCTTACTGAACACGAT | 75 | 0067-0084 | Coding |
| 25391 | CTCGTCCTTACTGAACAC | 76 | 0070-0087 | Coding |
| 25392 | AACTCGTCCTTACTGAAC | 77 | 0072-0089 | Coding |
| 25393 | CATAGTTCTCGAAGACGG | 78 | 0110-0127 | Coding |
| 25394 | TCGGCCACATAGTTCTCG | 79 | 0117-0134 | Coding |
| 25395 | CCGTCCACCTCAATGTCG | 80 | 0132-0149 | Coding |
| 25396 | AAGCACATGAGAATGACG | 81 | 0234-0251 | Coding |
| 25397 | GAGTCCGGGCTGTCCACC | 82 | 0255-0272 | Coding |
| 25398 | ATGTTCTCCAGCGAGTCC | 83 | 0267-0284 | Coding |
| 25399 | GGGATGTTCTCCAGCGAG | 84 | 0270-0287 | Coding |
| 25400 | GACATGCTCGTCGCTGCG | 85 | 0364-0381 | Coding |
| 25401 | CGGACATGCTCGTCGCTG | 86 | 0366-0383 | Coding |
| 25402 | TGTGCGGACATGCTCGTC | 87 | 0370-0387 | Coding |
| 25403 | CTCTGTGCGGACATGCTC | 88 | 0373-0390 | Coding |
| 25404 | CCAGCTCTGTGCGGACAT | 89 | 0377-0394 | Coding |
| 25405 | CGGGCCAGCTCTGTGCGG | 90 | 0381-0398 | Coding |
| 25406 | TGCGGGCCAGCTCTGTGC | 91 | 0383-0400 | Coding |
| 25407 | GTTCCTGCTTCATGCGGG | 92 | 0395-0412 | Coding |
| 25408 | ACGGGTTCCTGCTTCATG | 93 | 0399-0416 | Coding |
| 25409 | GTAGTCGTAGGCTTGGAT | 94 | 0451-0468 | Coding |
| 25410 | CGAGGTAGTCGTAGGCTT | 95 | 0455-0472 | Coding |
| 25411 | GTCTTGGCAGAGCACTCG | 96 | 0471-0488 | Coding |
| 25412 | ACCTCGCGCACGCCTTCC | 97 | 0492-0509 | Coding |
| 25413 | AGACCTCGCGCACGCCTT | 98 | 0494-0511 | Coding |
| 25414 | CGAAGACCTCGCGCACGC | 99 | 0497-0514 | Coding |
| 25415 | CTCGAAGACCTCGCGCAC | 100 | 0499-0516 | Coding |
| 25416 | GCCGTCTCGAAGACCTCG | 101 | 0504-0521 | Coding |
| 25417 | CGTGGCCGTCTCGAAGAC | 102 | 0508-0525 | Coding |
| 25418 | GTTCTGGGAGCCGTAGCG | 103 | 0544-0561 | Coding |
| 25419 | GCCGTTCTGGGAGCCGTA | 104 | 0547-0564 | Coding |
| 25420 | GATGCAGCCGTTCTGGGA | 105 | 0553-0570 | Coding |
| 25421 | GTTGATGCAGCCGTTCTG | 106 | 0556-0573 | Coding |
| 25422 | CAGCAGTTGATGCAGCCG | 107 | 0561-0578 | Coding |
| 25423 | AGCACCTTGCAGCAGTTG | 108 | 0570-0587 | Coding |

[1] All cytidines are 5-methyl-cytidines; all linkages are phosphorothioate linkages.
[2] Co-ordinates from Genbank Accession No. X06820, locus name "HSRHOB6" SEQ ID NO. 68.

Example 14
Antisense Inhibition of RhoB Expression-phosphorothioate Oligodeoxynucleotides In accordance with the present invention, the oligonucleotides shown in Table 14 were analyzed for effect on RhoB mRNA levels by quantitative real-time PCR as described in examples herein. Data are averages from three experiments. If present, "N.D." indicates "no data".

TABLE 15

Inhibition of RhoB mRNA levels by phosphorothioate oligodeoxynucleotides

| ISIS # | REGION | TARGET SITE | SEQUENCE | % Inhibition | SEQ ID NO. |
|---|---|---|---|---|---|
| 25384 | Coding | 14 | CCACCACCAGCTTCTTGC | 0 | 69 |
| 25385 | CODING | 24 | CCGTCGCCCACCACCACC | 0 | 70 |
| 25386 | CODING | 43 | GCACGTCTTGCCACACGC | 0 | 71 |
| 25387 | CODING | 61 | ACTGAACACGATCAGCAG | 0 | 72 |
| 25388 | CODING | 63 | TTACTGAACACGATCAGC | 0 | 73 |
| 25389 | CODING | 65 | CCTTACTGAACACGATCA | 0 | 74 |
| 25390 | CODING | 67 | GTCCTTACTGAACACGAT | 5 | 75 |
| 25391 | CODING | 70 | CTCGTCCTTACTGAACAC | 1 | 76 |
| 25392 | CODING | 72 | AACTCGTCCTTACTGAAC | 30 | 77 |
| 25393 | CODING | 110 | CATAGTTCTCGAAGACGG | 0 | 78 |
| 25394 | CODING | 117 | TCGGCCACATAGTTCTCG | 13 | 79 |
| 25395 | CODING | 132 | CCGTCCACCTCAATGTCG | 0 | 80 |
| 25396 | CODING | 234 | AAGCACATGAGAATGACG | 0 | 81 |
| 25397 | CODING | 255 | GAGTCCGGGCTGTCCACC | 0 | 82 |
| 25398 | CODING | 267 | ATGTTCTCCAGCGAGTCC | 0 | 83 |
| 25399 | CODING | 270 | GGGATGTTCTCCAGCGAG | 33 | 84 |
| 25400 | CODING | 364 | GACATGCTCGTCGCTGCG | 0 | 85 |
| 25401 | CODING | 366 | CGGACATGCTCGTCGCTG | 0 | 86 |
| 25402 | CODING | 370 | TGTGCGGACATGCTCGTC | 0 | 87 |
| 25403 | CODING | 373 | CTCTGTGCGGACATGCTC | 39 | 88 |
| 25404 | CODING | 377 | CCAGCTCTGTGCGGACAT | 21 | 89 |
| 25405 | CODING | 381 | CGGGCCAGCTCTGTGCGG | 38 | 90 |
| 25406 | CODING | 383 | TGCGGGCCAGCTCTGTGC | 31 | 91 |
| 25407 | CODING | 395 | GTTCCTGCTTCATGCGGG | 27 | 92 |
| 25408 | CODING | 399 | ACGGGTTCCTGCTTCATG | 0 | 93 |
| 25409 | CODING | 451 | GTAGTCGTAGGCTTGGAT | 29 | 94 |
| 25410 | CODING | 455 | CGAGGTAGTCGTAGGCTT | 39 | 95 |
| 25411 | CODING | 471 | GTCTTGGCAGAGCACTCG | 20 | 96 |
| 25412 | CODING | 492 | ACCTCGCGCACGCCTTCC | 0 | 97 |
| 25413 | CODING | 494 | AGACCTCGCGCACGCCTT | 16 | 98 |
| 25414 | CODING | 497 | CGAAGACCTCGCGCACGC | 0 | 99 |
| 25415 | CODING | 499 | CTCGAAGACCTCGCGCAC | 0 | 100 |
| 25416 | CODING | 504 | GCCGTCTCGAAGACCTCG | 0 | 101 |
| 25417 | CODING | 508 | CGTGGCCGTCTCGAAGAC | 0 | 102 |
| 25418 | CODING | 544 | GTTCTGGGAGCCGTAGCG | 36 | 103 |
| 25419 | CODING | 547 | GCCGTTCTGGGAGCCGTA | 0 | 104 |
| 25420 | CODING | 553 | GATGCAGCCGTTCTGGGA | 0 | 105 |

TABLE 15-continued

Inhibition of RhoB mRNA levels by phosphorothioate oligodeoxynucleotides

| ISIS # | REGION | TARGET SITE | SEQUENCE | % Inhibition | SEQ ID NO. |
|---|---|---|---|---|---|
| 25421 | CODING | 556 | GTTGATGCAGCCGTTCTG | 7 | 106 |
| 25422 | CODING | 561 | CAGCAGTTGATGCAGCCG | 31 | 107 |
| 25423 | CODING | 570 | AGCACCTTGCAGCAGTTG | 0 | 108 |

As shown in Table 15, SEQ ID Nos 77, 84, 88, 90, 91, 92, 94, 95, 103 and 107 demonstrated at least 25% inhibition of RhoB expression in this assay and are therefore preferred.

Example 15
Antisense Inhibition of RhoB Expression-phosphorothioate 2'-MOE gapmer Oligonucleotides In accordance with the present invention, a second series of oligonucleotides targeted to human RhoB were synthesized. The oligonucleotide sequences are shown in Table 16. Target sites are indicated by nucleotide numbers, as given in the sequence source reference (Genbank accession no. X06820), to which the oligonucleotide binds.

All compounds in Table 16 are chimeric oligonucleotides ("gapmers") 18 nucleotides in length, composed of a central "gap" region consisting of ten 2'-deoxynucleotides, which is flanked on both sides (5' and 3' directions) by four-nucleotide "wings". The wings are composed of 2'-methoxyethyl (2'-MOE)nucleotides. The internucleoside (backbone) linkages are phosphorothioate (P=S) throughout the oligonucleotide. Cytidine residues in the 2'-MOE wings are 5-methylcytidines.

TABLE 16

Nucleotide Sequences of Human RhoB Gapiner Oligonucleotides

| ISIS NO. | NUCLEOTIDE SEQUENCE (51 ->31) | SEQ ID NO: | TARGET GENE NUCLEOTIDE CO-ORDINATES[1] | GENE TARGET REGION |
|---|---|---|---|---|
| 25424 | CCACCACCAGCTTCTTGC | 69 | 0014–0031 | Coding |
| 25425 | CCGTCGCCCACCACCACC | 70 | 0024–0041 | Coding |
| 25426 | GCACGTCTTGCCACACGC | 71 | 0043–0060 | Coding |
| 25427 | ACTGAACACGATCAGCAG | 72 | 0061–0078 | Coding |
| 25428 | TTACTGAACACGATCAGC | 73 | 0063–0080 | Coding |
| 25429 | CCTTACTGAACACGATCA | 74 | 0065–0082 | Coding |
| 25430 | GTCCTTACTGAACACGAT | 75 | 0067–0084 | Coding |
| 25431 | CTCGTCCTTACTGAACAC | 76 | 0070–0087 | Coding |
| 25432 | AACTCGTCCTTACTGAAC | 77 | 0072–0089 | Coding |
| 25433 | CATAGTTCTCGAAGACGG | 78 | 0110–0127 | Coding |
| 25434 | TCGGCCACATAGTTCTCG | 79 | 0117–0134 | Coding |
| 25435 | CCGTCCACCTCAATGTCG | 80 | 0132–0149 | Coding |
| 25436 | AAGCACATGAGAATGACG | 81 | 0234–0251 | Coding |
| 25437 | GAGTCCGGGCTGTCCACC | 82 | 0255–0272 | Coding |
| 25438 | ATGTTCTCCAGCGAGTCC | 83 | 0267–0284 | Coding |
| 25439 | GGGATGTTCTCCAGCGAG | 84 | 0270–0287 | Coding |
| 25440 | GACATGCTCGTCGCTGCG | 85 | 0364–0381 | Coding |
| 25441 | CGGACATGCTCGTCGCTG | 86 | 0366–0383 | Coding |
| 25442 | TGTGCGGACATGCTCGTC | 87 | 0370–0387 | Coding |
| 25443 | CTCTGTGCGGACATGCTC | 88 | 0373–0390 | Coding |
| 25444 | CCAGCTCTGTGCGGACAT | 89 | 0377–0394 | Coding |
| 25445 | CGGGCCAGCTCTGTGCGG | 90 | 0381–0398 | Coding |
| 25446 | TGCGGGCCAGCTCTGTGC | 91 | 0383–0400 | Coding |
| 25447 | GTTCCTGCTTCATGCGGG | 92 | 0395–0412 | Coding |
| 25448 | ACGGGTTCCTGCTTCATG | 93 | 0399–0416 | Coding |
| 25449 | GTAGTCGTAGGCTTGGAT | 94 | 0451–0468 | Coding |
| 25450 | CGAGGTAGTCGTAGGCTT | 95 | 0455–0472 | Coding |
| 25451 | GTCTTGGCAGAGCACTCG | 96 | 0471–0488 | Coding |
| 25452 | ACCTCGCGCACGCCTTCC | 97 | 0492–0509 | Coding |
| 25453 | AGACCTCGCGCACGCCTT | 98 | 0494–0511 | Coding |
| 25454 | CGAAGACCTCGCGCACGC | 99 | 0497–0514 | Coding |
| 25455 | CTCGAAGACCTCGCGCAC | 100 | 0499–0516 | Coding |
| 25456 | GCCGTCTCGAAGACCTCG | 101 | 0504–0521 | Coding |
| 25457 | CGTGGCCGTCTCGAAGAC | 102 | 0508–0525 | Coding |
| 25458 | GTTCTGGGAGCCGTAGCG | 103 | 0544–0561 | Coding |
| 25459 | GCCGTTCTGGGAGCCGTA | 104 | 0547–0564 | Coding |
| 25460 | GATGCAGCCGTTCTGGGA | 105 | 0553–0570 | Coding |
| 25461 | GTTGATGCAGCCGTTCTG | 106 | 0556–0573 | Coding |
| 25462 | CAGCAGTTGATGCAGCCG | 107 | 0561–0578 | Coding |
| 25463 | AGCACCTTGCAGCAGTTG | 108 | 0570–0587 | Coding |

[1]Emboldened residues are 2'-methaxyethoxy residues (others are 2'-deoxy-). All 2'-methoxyethoxy cytidines and cytidines are 5-methyl-cytidines; all linkages are phosphorothioate linkages.
[2]Co-ordinates from Genbank Accession No. X06820, locus name "HSRHOB6" SEQ ID NO. 68.

Data for the compounds in Table 16 were obtained by real-time quantitative PCR as described in other examples herein and are averaged from three experiments. Results are shown in Table 17. If present, "N.D." indicates "no data".

TABLE 17

Inhibition of RhoB mRNA levels by chimeric phosphorothioate oligonucleotides having 2'-MOE wings and a deoxy gap

| ISIS # | REGION | TARGET SITE | SEQUENCE | % Inhibition | SEQ ID NO. |
|---|---|---|---|---|---|
| 25424 | Coding | 14 | CCACCACCAGCTTCTTGC | 29 | 69 |
| 25425 | CODING | 24 | CCGTCGCCCACCACCACC | 23 | 70 |
| 25426 | CODING | 43 | GCACGTCTTGCCACACGC | 46 | 71 |
| 25427 | CODING | 61 | ACTGAACACGATCAGCAG | 37 | 72 |
| 25428 | CODING | 63 | TTACTGAACACGATCAGC | 47 | 73 |
| 25429 | CODING | 65 | CCTTACTGAACACGATCA | 7 | 74 |
| 25430 | CODING | 67 | GTCCTTACTGAACACGAT | 46 | 75 |
| 25431 | CODING | 70 | CTCGTCCTTACTGAACAC | 52 | 76 |
| 25432 | CODING | 72 | AACTCGTCCTTACTGAAC | 35 | 77 |
| 25433 | CODING | 110 | CATAGTTCTCGAAGACGG | 29 | 78 |
| 25434 | CODING | 117 | TCGGCCACATAGTTCTCG | 65 | 79 |
| 25435 | CODING | 132 | CCGTCCACCTCAATGTCG | 40 | 80 |
| 25436 | CODING | 234 | AAGCACATGAGAATGACG | 44 | 81 |
| 25437 | CODING | 255 | GAGTCCGGGCTGTCCACC | 36 | 82 |
| 25438 | CODING | 267 | ATGTTCTCCAGCGAGTCC | 28 | 83 |
| 25439 | CODING | 270 | GGGATGTTCTCCAGCGAG | 54 | 84 |
| 25440 | CODING | 364 | GACATGCTCGTCGCTGCG | 49 | 85 |
| 25441 | CODING | 366 | CGGACATGCTCGTCGCTG | 46 | 86 |
| 25442 | CODING | 370 | TGTGCGGACATGCTCGTC | 65 | 87 |
| 25443 | CODING | 373 | CTCTGTGCGGACATGCTC | 39 | 88 |
| 25444 | CODING | 377 | CCAGCTCTGTGCGGACAT | 19 | 89 |
| 25445 | CODING | 381 | CGGGCCAGCTCTGTGCGG | 21 | 90 |
| 25446 | CODING | 383 | TGCGGGCCAGCTCTGTGC | 9 | 91 |
| 25447 | CODING | 395 | GTTCCTGCTTCATGCGGG | 16 | 92 |
| 25448 | CODING | 399 | ACGGGTTCCTGCTTCATG | 7 | 93 |
| 25449 | CODING | 451 | GTAGTCGTAGGCTTGGAT | 38 | 94 |
| 25450 | CODING | 455 | CGAGGTAGTCGTAGGCTT | 0 | 95 |
| 25451 | CODING | 471 | GTCTTGGCAGAGCACTCG | 42 | 96 |
| 25452 | CODING | 492 | ACCTCGCGCACGCCTTCC | 9 | 97 |
| 25453 | CODING | 494 | AGACCTCGCGCACGCCTT | 7 | 98 |
| 25454 | CODING | 497 | CGAAGACCTCGCGCACGC | 12 | 99 |
| 25455 | CODING | 499 | CTCGAAGACCTCGCGCAC | 23 | 100 |
| 25456 | CODING | 504 | GCCGTCTCGAAGACCTCG | 34 | 101 |
| 25457 | CODING | 508 | CGTGGCCGTCTCGAAGAC | 27 | 102 |
| 25458 | CODING | 544 | GTTCTGGGAGCCGTAGCG | 58 | 103 |
| 25459 | CODING | 547 | GCCGTTCTGGGAGCCGTA | 63 | 104 |
| 25460 | CODING | 553 | GATGCAGCCGTTCTGGGA | 17 | 105 |

TABLE 17-continued

Inhibition of RhoB mRNA levels by chimeric phosphorothioate oligonucleotides having 2'-MOE wings and a deoxy gap

| ISIS # | TARGET REGION | SITE | SEQUENCE | % Inhibition | SEQ ID NO. |
|---|---|---|---|---|---|
| 25461 | CODING | 556 | GTTGATGCAGCCGTTCTG | 21 | 106 |
| 25462 | CODING | 561 | CAGCAGTTGATGCAGCCG | 50 | 107 |
| 25463 | CODING | 570 | AGCACCTTGCAGCAGTTG | 55 | 108 |

As shown in Table 17, SEQ ID Nos 71, 62, 63, 75, 76, 77, 79, 80, 81, 82, 84, 85, 86, 87, 88, 94, 96, 101, 103, 104, 107 and 108 demonstrated at least 30% inhibition of RhoB expression in this experiment and are therefore preferred.

Example 16
Synthesis of RhoC Antisense Oligonucleotide Sequences

Oligonucleotide sequences were synthesized as described in previous examples. Antisense oligonucleotides were designed to target human RhoC. Target sequence data are from the RhoC cDNA sequence determined by Fagan, K. P., et al.; Genbank accession number L25081, provided herein as SEQ ID NO: 109.

TABLE 18

Nucleotide Sequences of Human RhoC Phosphorothioate Oligonucleotides

| ISIS NO. | NUCLEOTIDE SEQUENCE (5'->3') | SEQ ID NO: | TARGET GENE NUCLEOTIDE CO-ORDINATES[1] | GENE TARGET REGION |
|---|---|---|---|---|
| 25304 | GAGCTGAGATGAAGTCAA | 110 | 0004–0021 | 5'-UTR |
| 25305 | GCTGAAGTTCCCAGGCTG | 111 | 0044–0061 | 5'-UTR |
| 25306 | CCGGCTGAAGTTCCCAGG | 112 | 0047–0064 | 5'-UTR |
| 25307 | GGCACCATCCCCAACGAT | 113 | 0104–0121 | Coding |
| 25308 | AGGCACCATCCCCAACGA | 114 | 0105–0122 | Coding |
| 25309 | TCCCACAGGCACCATCCC | 115 | 0111–0128 | Coding |
| 25310 | AGGTCTTCCCACAGGCAC | 116 | 0117–0134 | Coding |
| 25311 | ATGAGGAGGCAGGTCTTC | 117 | 0127–0144 | Coding |
| 25312 | TTGCTGAAGACGATGAGG | 118 | 0139–0156 | Coding |
| 25313 | TCAAAGACAGTAGGGACG | 119 | 0178–0195 | Coding |
| 25314 | TTCTCAAAGACAGTAGGG | 120 | 0181–0198 | Coding |
| 25315 | AGTTCTCAAAGACAGTAG | 121 | 0183–0200 | Coding |
| 25316 | TGTTTTCCAGGCTGTCAG | 122 | 0342–0359 | Coding |
| 25317 | TCGTCTTGCCTCAGGTCC | 123 | 0433–0450 | Coding |
| 25318 | GTGTGCTCGTCTTGCCTC | 124 | 0439–0456 | Coding |
| 25319 | CTCCTGGTGTGCTCGTCT | 125 | 0445–0462 | Coding |
| 25320 | CAGACCGAACGGGCTCCT | 126 | 0483–0500 | Coding |
| 25321 | TTCCTCAGACCGAACGGG | 127 | 0488–0505 | Coding |
| 25322 | ACTCAAGGTAGCCAAAGG | 128 | 0534–0551 | Coding |
| 25323 | CTCCCGCACTCCCTCCTT | 129 | 0566–0583 | Coding |
| 25324 | CTCAAACACCTCCCGCAC | 130 | 0575–0592 | Coding |
| 25325 | GGCCATCTCAAACACCTC | 131 | 0581–0598 | Coding |
| 25326 | CTTGTTCTTGCGGACCTG | 132 | 0614–0631 | Coding |
| 25327 | CCCCTCCGACGCTTGTTC | 133 | 0625–0642 | Coding |
| 25328 | GTATGGAGCCCTCAGGAG | 134 | 0737–0754 | 3'-UTR |
| 25329 | GAGCCTTCAGTATGGAGC | 135 | 0746–0763 | 3'-UTR |
| 25330 | GAAAATGGAGCCTTCAGT | 136 | 0753–0770 | 3'-UTR |
| 25331 | GGAACTGAAAATGGAGCC | 137 | 0759–0776 | 3'-UTR |
| 25332 | GGAGGGAACTGAAAATGG | 138 | 0763–0780 | 3'-UTR |
| 25333 | GCAGGAGGGAACTGAAAA | 139 | 0766–0783 | 3'-UTR |
| 25334 | AGGGCAGGGCATAGGCGT | 140 | 0851–0868 | 3'-UTR |
| 25335 | GGAAGGGCAGGGCATAGG | 141 | 0854–0871 | 3'-UTR |
| 25336 | CATGAGGAAGGGCAGGGC | 142 | 0859–0876 | 3'-UTR |
| 25337 | TAAAGTGCTGGTGTGTGA | 143 | 0920–0937 | 3'-UTR |
| 25338 | CCTGTGAGCCAGAAGTGT | 144 | 0939–0956 | 3'-UTR |
| 25339 | TTCCTGTGAGCCAGAAGT | 145 | 0941–0958 | 3'-UTR |
| 25340 | CACTTTCCTGTGAGCCAG | 146 | 0945–0962 | 3'-UTR |
| 25341 | AGACACTTTCCTGTGAGC | 147 | 0948–0965 | 3'-UTR |
| 25342 | ACTCTGGGTCCCTACTGC | 148 | 0966–0983 | 3'-UTR |
| 25343 | TGCAGAAACAACTCCAGG | 149 | 0992–1009 | 3'-UTR |

[1]All cytidines are 5-methyl-cytidines; all linkages are phosphorothioate linkages.
[2]Co-ordinates from Genbank Accession No. L25081, locus name "HUMRHOCA" SEQ ID NO. 109.

The compounds shown in Table 18 were analyzed for effect on RhoC mRNA levels by quantitative real-time PCR as described in examples herein. Data are shown in Table 19 and are averages from three experiments. If present, "N.D." indicates "no data".

TABLE 19

Inhibition of RhoC mRNA levels by phosphorothioate oligodeoxynucleotides

| ISIS # | TARGET REGION | SITE | SEQUENCE | % Inhibition | SEQ ID NO |
|---|---|---|---|---|---|
| 25304 | 5'UTR | 4 | GAGCTGAGATGAAGTCAA | 29 | 110 |
| 25305 | 5'UTR | 44 | GCTGAAGTTCCCAGGCTG | 25 | 111 |
| 25306 | 5'UTR | 47 | CCGGCTGAAGTTCCCAGG | 42 | 112 |
| 25307 | CODING | 104 | GGCACCATCCCCAACGAT | 81 | 113 |
| 25308 | CODING | 105 | AGGCACCATCCCCAACGA | 81 | 114 |
| 25309 | CODING | 111 | TCCCACAGGCACCATCCC | 70 | 115 |
| 25310 | CODING | 117 | AGGTCTTCCCACAGGCAC | 40 | 116 |
| 25311 | CODING | 127 | ATGAGGAGGCAGGTCTTC | 41 | 117 |
| 25312 | CODING | 139 | TTGCTGAAGACGATGAGG | 23 | 118 |
| 25313 | CODING | 178 | TCAAAGACAGTAGGGACG | 0 | 119 |
| 25314 | CODING | 181 | TTCTCAAAGACAGTAGGG | 2 | 120 |
| 25315 | CODING | 183 | AGTTCTCAAAGACAGTAG | 38 | 121 |
| 25316 | CODING | 342 | TGTTTTCCAGGCTGTCAG | 59 | 122 |
| 25317 | CODING | 433 | TCGTCTTGCCTCAGGTCC | 79 | 123 |
| 25318 | CODING | 439 | GTGTGCTCGTCTTGCCTC | 67 | 124 |
| 25319 | CODING | 445 | CTCCTGGTGTGCTCGTCT | 67 | 125 |
| 25320 | CODING | 483 | CAGACCGAACGGGCTCCT | 65 | 126 |
| 25321 | CODING | 488 | TTCCTCAGACCGAACGGG | 57 | 127 |
| 25322 | CODING | 534 | ACTCAAGGTAGCCAAAGG | 33 | 128 |
| 25323 | CODING | 566 | CTCCCGCACTCCCTCCTT | 91 | 129 |
| 25324 | CODING | 575 | CTCAAACACCTCCCGCAC | 34 | 130 |
| 25325 | CODING | 581 | GGCCATCTCAAACACCTC | 64 | 131 |
| 25326 | CODING | 614 | CTTGTTCTTGCGGACCTG | 72 | 132 |
| 25327 | CODING | 625 | CCCCTCCGACGCTTGTTC | 66 | 133 |
| 25328 | 3'UTR | 737 | GTATGGAGCCCTCAGGAG | 60 | 134 |
| 25329 | 3'UTR | 746 | GAGCCTTCAGTATGGAGC | 63 | 135 |
| 25330 | 3'UTR | 753 | GAAAATGGAGCCTTCAGT | 24 | 136 |
| 25331 | 3'UTR | 759 | GGAACTGAAAATGGAGCC | 2 | 137 |
| 25332 | 3'UTR | 763 | GGAGGGAACTGAAAATGG | 13 | 138 |
| 25333 | 3'UTR | 766 | GCAGGAGGGAACTGAAAA | 27 | 139 |
| 25334 | 3'UTR | 851 | AGGGCAGGGCATAGGCGT | 31 | 140 |
| 25335 | 3'UTR | 854 | GGAAGGGCAGGGCATAGG | 21 | 141 |
| 25336 | 3'UTR | 859 | CATGAGGAAGGGCAGGGC | 0 | 142 |
| 25337 | 3'UTR | 920 | TAAAGTGCTGGTGTGTGA | 39 | 143 |
| 25338 | 3'UTR | 939 | CCTGTGAGCCAGAAGTGT | 69 | 144 |
| 25339 | 3'UTR | 941 | TTCCTGTGAGCCAGAAGT | 69 | 145 |
| 25340 | 3'UTR | 945 | CACTTTCCTGTGAGCCAG | 82 | 146 |
| 25341 | 3'UTR | 948 | AGACACTTTCCTGTGAGC | 69 | 147 |
| 25342 | 3'UTR | 966 | ACTCTGGGTCCCTACTGC | 20 | 148 |
| 25343 | 3'UTR | 992 | TGCAGAAACAACTCCAGG | 0 | 149 |

As shown in Table 19, SEQ ID NOs 113, 114, 115, 122, 123, 124, 125, 126, 127, 129, 131, 132, 133, 134, 135, 144, 145, 146 and 147 demonstrated at least 50% inhibition of RhoC expression in this assay and are therefore preferred.

Example 17
Antisense Inhibition of RhoC Expression-phosphorothioate 2'-MOE Gapmer Oligonucleotides In accordance with the present invention, a second series of oligonucleotides targeted to human RhoC were synthesized. The oligonucleotide sequences are shown in Table 20. Target sites are indicated by nucleotide numbers, as given in the sequence source reference (Genbank accession no. L25081), to which the oligonucleotide binds.

All compounds in Table 20 are chimeric oligonucleotides ("gapmers") 18 nucleotides in length, composed of a central "gap" region consisting of ten 2'-deoxynucleotides, which is flanked on both sides (5' and 3' directions) by four-nucleotide "wings". The wings are composed of 2$^1$-methoxyethyl (2'-MOE)nucleotides. The internucleoside (backbone) linkages are phosphorothioate (P=S) throughout the oligonucleotide. Cytidine residues in the 2'-MOE wings are 5-methylcytidines.

TABLE 20

Nucleotide Sequences of Human RhoC Gapmer Oligonucleotides

| ISIS NO. | NUCLEOTIDE SEQUENCE (5'->3') | SEQ ID NO: | TARGET GENE NUCLEOTIDE CO-ORDINATES[1] | GENE TARGET REGION |
|---|---|---|---|---|
| 25344 | GAGCTGAGATGAAGTCAA | 110 | 0004-0021 | 5'-UTR |
| 25345 | GCTGAAGTTCCCAGGCTG | 111 | 0044-0061 | 5'-UTR |
| 25346 | CCGGCTGAAGTTCCCAGG | 112 | 0047-0064 | 5'-UTR |
| 25347 | GGCACCATCCCCAACGAT | 113 | 0104-0121 | Coding |
| 25348 | AGGCACCATCCCCAACGA | 114 | 0105-0122 | Coding |
| 25349 | TCCCACAGGCACCATCCC | 115 | 0111-0128 | Coding |
| 25350 | AGGTCTTCCCACAGGCAC | 116 | 0117-0134 | Coding |
| 25351 | ATGAGGAGGCAGGTCTTC | 117 | 0127-0144 | Coding |
| 25352 | TTGCTGAAGACGATGAGG | 118 | 0139-0156 | Coding |
| 25353 | TCAAAGACAGTAGGGACG | 119 | 0178-0195 | Coding |
| 25354 | TTCTCAAAGACAGTAGGG | 120 | 0181-0198 | Coding |
| 25355 | AGTTCTCAAAGACAGTAG | 121 | 0183-0200 | Coding |
| 25356 | TGTTTTCCAGGCTGTCAG | 122 | 0342-0359 | Coding |
| 25357 | TCGTCTTGCCTCAGGTCC | 123 | 0433-0450 | Coding |
| 25358 | GTGTGCTCGTCTTGCCTC | 124 | 0439-0456 | Coding |
| 25359 | CTCCTGGTGTGCTCGTCT | 125 | 0445-0462 | Coding |
| 25360 | CAGACCGAACGGGCTCCT | 126 | 0483-0500 | Coding |
| 25361 | TTCCTCAGACCGAACGGG | 127 | 0488-0505 | Coding |
| 25362 | ACTCAAGGTAGCCAAAGG | 128 | 0534-0551 | Coding |
| 25363 | CTCCCGCACTCCCTCCTT | 129 | 0566-0583 | Coding |
| 25364 | CTCAAACACCTCCCGCAC | 130 | 0575-0592 | Coding |
| 25365 | GGCCATCTCAAACACCTC | 131 | 0581-0598 | Coding |
| 25366 | CTTGTTCTTGCGGACCTG | 132 | 0614-0631 | Coding |
| 25367 | CCCCTCCGACGCTTGTTC | 133 | 0625-0642 | Coding |
| 25368 | GTATGGAGCCCTCAGGAG | 134 | 0737-0754 | 3'-UTR |
| 25369 | GAGCCTTCAGTATGGAGC | 135 | 0746-0763 | 3'-UTR |
| 25370 | GAAAATGGAGCCTTCAGT | 136 | 0753-0770 | 3'-UTR |
| 25371 | GGAACTGAAAATGGAGCC | 137 | 0759-0776 | 3'-UTR |
| 25372 | GGAGGGAACTGAAAATGG | 138 | 0763-0780 | 3'-UTR |
| 25373 | GCAGGAGGGAACTGAAAA | 139 | 0766-0783 | 3'-UTR |
| 25374 | AGGGCAGGGCATAGGCGT | 140 | 0851-0868 | 3'-UTR |
| 25375 | GGAAGGGCAGGGCATAGG | 141 | 0854-0871 | 3'-UTR |
| 25376 | CATGAGGAAGGGCAGGGC | 142 | 0859-0876 | 3'-UTR |
| 25377 | TAAAGTGCTGGTGTGTGA | 143 | 0920-0937 | 3'-UTR |
| 25378 | CCTGTGAGCCAGAAGTGT | 144 | 0939-0956 | 3'-UTR |
| 25379 | TTCCTGTGAGCCAGAAGT | 145 | 0941-0958 | 3'-UTR |
| 25380 | CACTTTCCTGTGAGCCAG | 146 | 0945-0962 | 3'-UTR |
| 25381 | AGACACTTTCCTGTGAGC | 147 | 0948-0965 | 3'-UTR |
| 25382 | ACTCTGGGTCCCTACTGC | 148 | 0966-0983 | 3'-UTR |
| 25383 | TGCAGAAACAACTCCAGG | 149 | 0992-1009 | 3'-UTR |

[1]Emboldened residues are 2'-methoxyethoxy residues (others are 2'-deoxy-). All 2'-methoxyethoxy cytidines and cytidines are 5-methyl-cytidines; all linkages are phosphorothioate linkages.
[2]Co-ordinates from Genbank Accession No. L25081, locus name "HUMRHOCA" SEQ ID NO. 109.

RhoC inhibition data for these compounds were obtained by real-time quantitative PCR as described in other examples herein and are averaged from three experiments.

Data are shown in Table 21. If present, "N.D." indicates "no data".

TABLE 21

Inhibition of RhoC mRNA levels by chimeric phosphorothioate oligonucleotides having 2'-MOE wings and a deoxy gap

| ISIS# | TARGET REGION | TARGET SITE | SEQUENCE | % Inhibition | SEQ ID NO. |
|---|---|---|---|---|---|
| 25344 | 5'UTR | 4 | GAGCTGAGATGAAGTCAA | 0 | 110 |
| 25345 | 5'UTR | 44 | GCTGAAGTTCCCAGGCTG | 35 | 111 |
| 25346 | 5'UTR | 47 | CCGGCTGAAGTTCCCAGG | 53 | 112 |
| 25347 | Coding | 104 | GGCACCATCCCCAACGAT | 50 | 113 |
| 25348 | Coding | 105 | AGGCACCATCCCCAACGA | 56 | 114 |
| 25349 | Coding | 111 | TCCCACAGGCACCATCCC | 4 | 115 |
| 25350 | Coding | 117 | AGGTCTTCCCACAGGCAC | 11 | 116 |
| 25351 | Coding | 127 | ATGAGGAGGCAGGTCTTC | 6 | 117 |
| 25352 | Coding | 139 | TTGCTGAAGACGATGAGG | 15 | 118 |
| 25353 | Coding | 178 | TCAAAGACAGTAGGGACG | 32 | 119 |
| 25354 | Coding | 181 | TTCTCAAAGACAGTAGGG | 7 | 120 |
| 25355 | Coding | 183 | AGTTCTCAAAGACAGTAG | 39 | 121 |
| 25356 | Coding | 342 | TGTTTTCCAGGCTGTCAG | 59 | 122 |
| 25357 | Coding | 433 | TCGTCTTGCCTCAGGTCC | 48 | 123 |
| 25358 | Coding | 439 | GTGTGCTCGTCTTGCCTC | 36 | 124 |
| 25359 | Coding | 445 | CTCCTGGTGTGCTCGTCT | 61 | 125 |
| 25360 | Coding | 483 | CAGACCGAACGGGCTCCT | 50 | 126 |
| 25361 | Coding | 488 | TTCCTCAGACCGAACGGG | 14 | 127 |
| 25362 | Coding | 534 | ACTCAAGGTAGCCAAAGG | 32 | 128 |
| 25363 | Coding | 566 | CTCCCGCACTCCCTCCTT | 21 | 129 |
| 25364 | Coding | 575 | CTCAAACACCTCCCGCAC | 9 | 130 |
| 25365 | Coding | 581 | GGCCATCTCAAACACCTC | 66 | 131 |
| 25366 | Coding | 614 | CTTGTTCTTGCGGACCTG | 61 | 132 |
| 25367 | Coding | 625 | CCCCTCCGACGCTTGTTC | 0 | 133 |
| 25368 | 3'UTR | 737 | GTATGGAGCCCTCAGGAG | 28 | 134 |
| 25369 | 3'UTR | 746 | GAGCCTTCAGTATGGAGC | 32 | 135 |
| 25370 | 3'UTR | 753 | GAAAATGGAGCCTTCAGT | 0 | 136 |
| 25371 | 3'UTR | 759 | GGAACTGAAAATGGAGCC | 40 | 137 |
| 25372 | 3'UTR | 763 | GGAGGGAACTGAAAATGG | 45 | 138 |
| 25373 | 3'UTR | 766 | GCAGGAGGGAACTGAAAA | 35 | 139 |
| 25374 | 3'UTR | 851 | AGGGCAGGGCATAGGCGT | 5 | 140 |
| 25375 | 3'UTR | 854 | GGAAGGGCAGGGCATAGG | 0 | 141 |
| 25376 | 3'UTR | 859 | CATGAGGAAGGGCAGGGC | 0 | 142 |
| 25377 | 3'UTR | 920 | TAAAGTGCTGGTGTGTGA | 20 | 143 |
| 25378 | 3'UTR | 939 | CCTGTGAGCCAGAAGTGT | 67 | 144 |
| 25379 | 3'UTR | 941 | TTCCTGTGAGCCAGAAGT | 61 | 145 |
| 25380 | 3'UTR | 945 | CACTTTCCTGTGAGCCAG | 80 | 146 |
| 25381 | 3'UTR | 948 | AGCAACTTTCCTGTGAGC | 0 | 147 |
| 25382 | 3'UTR | 966 | ACTCTGGGTCCCTACTGC | 0 | 148 |
| 25383 | 3'UTR | 992 | TGCAGAAACAACTCCAGG | 0 | 149 |

As shown in Table 21, SEQ ID NOs 111, 112, 113, 114, 119, 121, 122, 123, 124, 125, 126, 128, 131, 132, 134, 135, 137, 138, 139, 144, 145 and 146 demonstrated at least 25% inhibition of RhoC expression in this experiment and are therefore preferred.

Example 18

Synthesis of RhoG Antisense Oligonucleotide Sequences

Oligonucleotide sequences designed to target human RhoG were synthesized as described in previous examples and are shown in Table 22. Target sequence data are from the RhoG cDNA sequence published by Vincent, S., et al. (*Mol. Cell. Biol.* 1992, 12, 3138–3148); Genbank accession number X61587, provided herein as SEQ ID NO: 150.

TABLE 22

Nucleotide Sequences of Human RhoG Phosphorothioate Oligodeoxynucleotide

| ISIS NO. | NUCLEOTIDE SEQUENCE (5' -> 3') | SEQ ID NO: | TARGET GENE NUCLEOTIDE CO-ORDINATES[1] | GENE TARGET REGION |
|---|---|---|---|---|
| 25464 | GACCTGGTGCCCCTCCCG | 151 | 0048-0065 | 5'-UTR |
| 25465 | TCTTCTGGACCCCTCTGG | 152 | 0073-0090 | 5'-UTR |
| 25466 | GGCAGTGCCTCCTCTCTC | 153 | 0089-0106 | 5'-UTR |
| 25467 | GTGCAGTTGCTGTAGTGA | 154 | 0107-0124 | 5'-UTR |
| 25468 | GCATCGTGGGTGCAGTTG | 155 | 0116-0133 | AUG |
| 25469 | CCACCACGCACTTGATGC | 156 | 0137-0154 | Coding |
| 25470 | TTGTGTAGCAGATGAGCA | 157 | 0185-0202 | Coding |
| 25471 | AAAGCGTTAGTTGTGTAG | 158 | 0195-0212 | Coding |
| 25472 | GCGCGCTGTAATTGTCGA | 159 | 0239-0256 | Coding |
| 25473 | GGTTCACTGTGCGCCCGT | 160 | 0269-0286 | Coding |
| 25474 | GTCCCACAGGTTCAGGTT | 161 | 0283-0300 | Coding |
| 25475 | TGTACGGAGGCGGTCATA | 162 | 0319-0336 | Coding |
| 25476 | ACGTTGGTCTGAGGGTAG | 163 | 0342-0359 | Coding |
| 25477 | CAATGGAGAAACAGATGA | 164 | 0365-0382 | Coding |
| 25478 | CATAGGACGGCGGACTGG | 165 | 0383-0400 | Coding |
| 25479 | CGCACGTTCTCATAGGAC | 166 | 0393-0410 | Coding |
| 25480 | ACCTCTGGATGCCACTTG | 167 | 0414-0431 | Coding |
| 25481 | AGGGCAGTGGTGGCACAC | 168 | 0430-0447 | Coding |
| 25482 | CAGCAGGATGGGCACATC | 169 | 0448-0465 | Coding |
| 25483 | GGGTGTCAGGCTGGGCTC | 170 | 0488-0505 | Coding |
| 25484 | CCCTGCTGCGGTGTGATG | 171 | 0537-0554 | Coding |
| 25485 | CGCGAGTGCCTGGCCCTG | 172 | 0550-0567 | Coding |
| 25486 | GTAGCGCACAGCGTGGAT | 173 | 0574-0591 | Coding |
| 25487 | CATTCGAGGTAGCGCACA | 174 | 0582-0599 | Coding |
| 25488 | ACACCATCCTGTTGCAGG | 175 | 0606-0623 | Coding |
| 25489 | GAACACTTCCTTGACACC | 176 | 0619-0636 | Coding |
| 25490 | ACAGCCTCGGCGAACACT | 177 | 0630-0647 | Coding |
| 25491 | AAGAGGATGCAGGACCGC | 178 | 0684-0701 | Coding |
| 25492 | GCAGCCTCCAAGCCAAGT | 179 | 0713-0730 | 3'-UTR |
| 25493 | AAAAGGCATTCAGGGAAC | 180 | 0818-0835 | 3'-UTR |
| 25494 | GGGTCCAACCTTGGCTTG | 181 | 0936-0953 | 3'-UTR |
| 25495 | GTCAGTAGCGGAAAATGG | 182 | 0984-1001 | 3'-UTR |
| 25496 | AGCTGGATGAACTGGTCA | 183 | 0998-1015 | 3'-UTR |
| 25497 | AACTGTGTGGAAAGCTGG | 184 | 1010-1027 | 3'-UTR |
| 25498 | ACCACAATAGGCAGCAAC | 185 | 1028-1045 | 3'-UTR |
| 25499 | GAGGGCAGAGGTTAGAGA | 186 | 1074-1091 | 3'-UTR |
| 25500 | CAATTCCAAGAGCAGCGA | 187 | 1090-1107 | 3'-UTR |
| 25501 | TGGAGAAGGGAGAGAGCA | 188 | 1119-1136 | 3'-UTR |
| 25502 | ACATTCACCTTCTCAGGA | 189 | 1154-1171 | 3'-UTR |
| 25503 | GTCAGCAAATGCGTAAGG | 190 | 1199-1216 | 3'-UTR |

[1] All cytidines are 5-methyl-cytidines; all linkages are phosphorothioate linkages.
[2] Co-ordinates from Genbank Accession No. X61587, locus name "HSRHOG" SEQ ID NO. 150.

The compounds in Table 22 were analyzed for effect on RhoG mRNA levels by quantitative real-time PCR as described in other examples herein. Data, shown in Table 23, are averages from three experiments. If present, "N.D." indicates "no data".

TABLE 23

Inhibition of RhoG mRNA levels by phosphorothioate Oligodeoxynucleotides

| ISIS# | TARGET REGION | TARGET SITE | SEQUENCE | % Inhibition | SEQ ID NO. |
|---|---|---|---|---|---|
| 25464 | 5' UTR | 48 | GACCTGGTGCCCCTCCCG | 35 | 151 |
| 25465 | 5' UTR | 73 | TCTTCTGGACCCCTCTGG | 36 | 152 |
| 25466 | 5' UTR | 89 | GGCAGTGCCTCCTCTCTC | 35 | 153 |
| 25467 | 5' UTR | 107 | GTGCAGTTGCTGTAGTGA | 10 | 154 |
| 25468 | 5' UTR | 116 | GCATCGTGGGTGCAGTTG | 47 | 155 |
| 25469 | CODING | 137 | CCACCACGCACTTGATGC | 14 | 156 |
| 25470 | CODING | 185 | TTGTGTAGCAGATGAGCA | 35 | 157 |
| 25471 | CODING | 195 | AAAGCGTTAGTTGTGTAG | 0 | 158 |
| 25472 | CODING | 239 | GCGCGCTGTAATTGTCGA | 36 | 159 |
| 25473 | CODING | 269 | GGTTCACTGTGCGCCCGT | 16 | 160 |
| 25474 | CODING | 283 | GTCCCACAGGTTCAGGTT | 31 | 161 |
| 25475 | CODING | 319 | TGTACGGAGGCGGTCATA | 37 | 162 |
| 25476 | CODING | 342 | ACGTTGGTCTGAGGGTAG | 38 | 163 |
| 25477 | CODING | 365 | CAATGGAGAAACAGATGA | 0 | 164 |
| 25478 | CODING | 383 | CATAGGACGGCGGACTGG | 17 | 165 |
| 25479 | CODING | 393 | CGCACGTTCTCATAGGAC | 24 | 166 |
| 25480 | CODING | 414 | ACCTCTGGATGCCACTTG | 35 | 167 |
| 25481 | CODING | 430 | AGGGCAGTGGTGGCACAC | 15 | 168 |
| 25482 | CODING | 448 | CAGCAGGATGGGCACATC | 20 | 169 |
| 25483 | CODING | 488 | GGGTGTCAGGCTGGGCTC | 15 | 170 |
| 25484 | CODING | 537 | CCCTGCTGCGGTGTGATG | 44 | 171 |
| 25464 | 5' UTR | 48 | GACCTGGTGCCCCTCCCG | 35 | 151 |
| 25465 | 5' UTR | 73 | TCTTCTGGACCCCTCTGG | 36 | 152 |
| 25466 | 5' UTR | 89 | GGCAGTGCCTCCTCTCTC | 35 | 153 |
| 25485 | CODING | 550 | CGCGAGTGCCTGGCCCTG | 9 | 172 |
| 25486 | CODING | 574 | GTAGCGCACAGCGTGGAT | 35 | 173 |
| 25487 | CODING | 582 | CATTCGAGGTAGCGCACA | 39 | 174 |
| 25488 | CODING | 606 | ACACCATCCTGTTGCAGG | 23 | 175 |
| 25489 | CODING | 619 | GAACACTTCCTTGACACC | 31 | 176 |
| 25490 | CODING | 630 | ACAGCCTCGGCGAACACT | 6 | 177 |
| 25491 | CODING | 684 | AAGAGGATGCAGGACCGC | 18 | 178 |
| 25492 | 3' UTR | 713 | GCAGCCTCCAAGCCAAGT | 42 | 179 |
| 25493 | 3' UTR | 818 | AAAAGGCATTCAGGGAAC | 0 | 180 |
| 25494 | 3' UTR | 936 | GGGTCCAACCTTGGCTTG | 58 | 181 |
| 25495 | 3' UTR | 984 | GTCAGTAGCGGAAAATGG | 0 | 182 |
| 25496 | 3' UTR | 998 | AGCTGGATGAACTGGTCA | 23 | 183 |
| 25497 | 3' UTR | 1010 | AACTGTGTGGAAAGCTGG | 8 | 184 |
| 25498 | 3' UTR | 1028 | ACCACAATAGGCAGCAAC | 31 | 185 |
| 25499 | 3' UTR | 1074 | GAGGGCAGAGGTTAGAGA | 21 | 186 |
| 25500 | 3' UTR | 1090 | CAATTCCAAGAGCAGCGA | 18 | 187 |
| 25501 | 3' UTR | 1119 | TGGAGAAGGGAGAGAGCA | 32 | 188 |
| 25502 | 3' UTR | 1154 | ACATTCACCTTCTCAGGA | 20 | 189 |
| 25503 | 3' UTR | 1199 | GTCAGCAAATGCGTAAGG | 24 | 190 |

As shown in Table 23, SEQ ID NOs 151, 152, 153, 155, 157, 159, 61, 162, 163, 167, 171, 173, 174, 176, 179, 181, 185 and 188 demonstrated at least 25% inhibition of RhoG expression in this assay and are therefore preferred.

Example 19

Antisense Inhibition of RhoG Expression-phosphorothioate 2'-MOE Gapmer Oligonucleotides In accordance with the present invention, a second series of oligonucleotides targeted to human RhoG were synthesized. The oligonucleotide sequences are shown in Table 24. Target sites are indicated by nucleotide numbers, as given in the sequence source reference (Genbank accession no. X61587), to which the oligonucleotide binds.

All compounds in Table 24 are chimeric oligonucleotides ("gapmers") 18 nucleotides in length, composed of a central "gap" region consisting of ten 2'-deoxynucleotides, which is flanked on both sides (5' and 3' directions) by four-nucleotide "wings". The wings are composed of 2'-methoxyethyl (2'-MOB)nucleotides. The internucleoside (backbone) linkages are phosphorothioate (P=S) throughout the oligonucleotide. Cytidine residues in the 2'-MOE wings are 5-methylcytidines.

TABLE 24

Nucleotide Sequences of Human RhoG Gapmer Oligonucleotides

| ISIS NO. | NUCLEOTIDE SEQUENCE (5' -> 3') | SEQ ID NO: | TARGET GENE NUCLEOTIDE CO-ORDINATES[2] | GENE TARGET REGION |
|---|---|---|---|---|
| 25504 | GACCTGGTGCCCCTCCCG | 151 | 0048–0065 | 5'-UTR |
| 25505 | TCTTCTGGACCCCTCTGG | 152 | 0073–0090 | 5'-UTR |
| 25506 | GGCAGTGCCTCCTCTCTC | 153 | 0089–0106 | 5'-UTR |
| 25507 | GTGCAGTTGCTGTAGTGA | 154 | 0107–0124 | 5'-UTR |
| 25508 | GCATCGTCCOTGCAGTTG | 155 | 0116–0133 | AUG |
| 25509 | CCACCACGCACTTGATGC | 156 | 0137–0154 | Coding |
| 25510 | TTGTGTAGCAGATGAGCA | 157 | 0185–0202 | Coding |
| 25511 | AAAGCGTTAGTTGTGTAG | 158 | 0195–0212 | Coding |
| 25512 | GCGCGCTGTAATTGTCGA | 159 | 0239–0256 | Coding |
| 25513 | GGTTCACTGTGCGCCCGT | 160 | 0269–0286 | Coding |
| 25514 | GTCCCACAGGTTCAGGTT | 161 | 0283–0300 | Coding |
| 25515 | TGTACGGAGGCGGTCATA | 162 | 0319–0336 | Coding |
| 25516 | ACGTTGGTCTGAGGGTAG | 163 | 0342–0359 | Coding |
| 25517 | CAATGGAGAAACAGATGA | 164 | 0365–0382 | Coding |
| 25518 | CATAGGACGGCGGACTGG | 165 | 0383–0400 | Coding |
| 25519 | CGCACGTTCTCATAGGAC | 166 | 0393–0410 | Coding |
| 25520 | ACCTCTGGATGCCACTTG | 167 | 0414–0431 | Coding |
| 25521 | AGGGCAGTGGTGGCACAC | 168 | 0430–0447 | Coding |
| 25522 | CAGCAGGATGGGCACATC | 169 | 0448–0465 | Coding |
| 25523 | GGGTGTCAGGCTGGGCTC | 170 | 0488–0505 | Coding |
| 25524 | CCCTGCTGCGGTGTGATG | 171 | 0537–0554 | Coding |
| 25525 | CGCGAGTGCCTGGCCCTG | 172 | 0550–0567 | Coding |
| 25526 | GTAGCGCACAGCGTGGAT | 173 | 0574–0591 | Coding |
| 25527 | CATTCGAGGTAGCGCACA | 174 | 0582–0599 | Coding |
| 25528 | ACACCATCCTGTTGCAGG | 175 | 0606–0623 | Coding |
| 25529 | GAACACTTCCTTGACACC | 176 | 0619–0636 | Coding |
| 25530 | ACAGCCTCGGCGAACACT | 177 | 0630–0647 | Coding |
| 25531 | AAGAGGATGCAGGACCGC | 178 | 0684–0701 | Coding |
| 25532 | GCAGCCTCCAAGCCAAGT | 179 | 0713–0730 | 3'-UTR |
| 25533 | AAAAGGCATTCAGGGAAC | 180 | 0818–0835 | 3'-UTR |
| 25534 | GGGTCCAACCTTGGCTTG | 181 | 0936–0953 | 3'-UTR |
| 25535 | GTCAGTAGCGGAAAATGG | 182 | 0984–1001 | 3'-UTR |
| 25536 | AGCTGGATGAACTGGTCA | 183 | 0998–1015 | 3'-UTR |
| 25537 | AACTGTGTGGAAAGCTGG | 184 | 1010–1027 | 3'-UTR |
| 25538 | ACCACAATAGGCAGCAAC | 185 | 1028–1045 | 3'-UTR |
| 25539 | GAGGGCAGAGGTTAGAGA | 186 | 1074–1091 | 3'-UTR |
| 25540 | CAATTCCAAGAGCAGCGA | 187 | 1090–1107 | 3'-UTR |
| 25541 | TGGAGAAGGGAGAGAGCA | 188 | 1119–1136 | 3'-UTR |
| 25542 | ACATTCACCTTCTCAGGA | 189 | 1154–1171 | 3'-UTR |
| 25543 | GTCAGCAAATGCGTAAGG | 190 | 1199–1216 | 3'-UTR |

[1]Emboldened residues are 2'-methoxyethoxy residues (others are 2'-deoxy-). All 2'-methoxyethoxy cytidines and cytidines are 5-methyl-cytidines; all linkages are phosphorothioate linkages.
[2]Co-ordinates from Genbank Accession No. X61587, locus name "HSRHOG" SEQ ID NO. 150.

RhoG inhibition data for compounds in Table 24 were obtained by real-time quantitative PCR as described in other examples herein and are averaged from three experiments. Data are shown in Table 25. If present, "N.D." indicates "no data".

TABLE 25

Inhibition of RhoG mRNA levels by chimeric phosphorothioate oligonucleotides having 2'-MOE wings and a deoxy gap

| ISIS# | TARGET REGION | TARGET SITE | SEQUENCE | % Inhibition | SEQ ID NO. |
|---|---|---|---|---|---|
| 25504 | 5'UTR | 48 | GACCTGGTGCCCCTCCCG | 0 | 151 |
| 25505 | 5'UTR | 73 | TCTTCTGGACCCCTCTGG | 32 | 152 |
| 25506 | 5'UTR | 89 | GGCAGTGCCTCCTCTCTC | 28 | 153 |
| 25507 | 5'UTR | 107 | GTGCAGTTGCTGTAGTGA | 0 | 154 |
| 25508 | 5'UTR | 116 | GCATCGTGGGTGCAGTTG | 12 | 155 |
| 25509 | Coding | 137 | CCACCACGCACTTGATGC | 0 | 156 |
| 25510 | Coding | 185 | TTGTGTAGCAGATGAGCA | 0 | 157 |
| 25511 | Coding | 195 | AAAGCGTTAGTTGTGTAG | 33 | 158 |
| 25512 | Coding | 239 | GCGCGCTGTAATTGTCGA | 0 | 159 |
| 25513 | Coding | 269 | GGTTCACTGTGCGCCCGT | 82 | 160 |
| 25514 | Coding | 283 | GTCCCACAGGTTCAGGTT | 0 | 161 |
| 25515 | Coding | 319 | TGTACGGAGGCGGTCATA | 13 | 162 |
| 25516 | Coding | 342 | ACGTTGGTCTGAGGGTAG | 53 | 163 |
| 25517 | Coding | 365 | CAATGGAGAAACAGATGA | 0 | 164 |
| 25518 | Coding | 383 | CATAGGACGGCGGACTGG | 55 | 165 |
| 25519 | Coding | 393 | CGCACGTTCTCATAGGAC | 9 | 166 |
| 25520 | Coding | 414 | ACCTCTGGATGCCACTTG | 56 | 167 |
| 25521 | Coding | 430 | AGGGCAGTGGTGGCACAC | 0 | 168 |
| 25522 | Coding | 448 | CAGCAGGATGGGCACATC | 0 | 169 |
| 25523 | Coding | 488 | GGGTGTCAGGCTGGGCTC | 27 | 170 |
| 25524 | Coding | 537 | CCCTGCTGCGGTGTGATG | 55 | 171 |
| 25525 | Coding | 550 | CGCGAGTGCCTGGCCCTG | 41 | 172 |
| 25526 | Coding | 574 | GTAGCGCACAGCGTGGAT | 41 | 173 |
| 25527 | Coding | 582 | CATTCGAGGTAGCGCACA | 0 | 174 |
| 25528 | Coding | 606 | ACACCATCCTGTTGCAGG | 37 | 175 |
| 25529 | Coding | 619 | GAACACTTCCTTGACACC | 23 | 176 |
| 25530 | Coding | 630 | ACAGCCTCGGCGAACACT | 59 | 177 |
| 25531 | Coding | 684 | AAGAGGATGCAGGACCGC | 39 | 178 |
| 25532 | 3'UTR | 713 | GCAGCCTCCAAGCCAAGT | 13 | 179 |
| 25533 | 3'UTR | 818 | AAAAGGCATTCAGGGAAC | 43 | 180 |
| 25534 | 3'UTR | 936 | GGGTCCAACCTTGGCTTG | 78 | 181 |
| 25535 | 3'UTR | 984 | GTCAGTAGCGGAAAATGG | 54 | 182 |
| 25536 | 3'UTR | 998 | AGCTGGATGAACTGGTCA | 54 | 183 |
| 25537 | 3'UTR | 1010 | AACTGTGTGGAAAGCTGG | 59 | 184 |
| 25538 | 3'UTR | 1028 | ACCACAATAGGCAGCAAC | 48 | 185 |
| 25539 | 3'UTR | 1074 | GAGGGCAGAGGTTAGAGA | 0 | 188 |
| 25540 | 3'UTR | 1090 | CAATTCCAAGAGCAGCGA | 26 | 187 |
| 25541 | 3'UTR | 1119 | TGGAGAAGGGAGAGAGCA | 0 | 188 |
| 25542 | 3'UTR | 1154 | ACATTCACCTTCTCAGGA | 26 | 189 |
| 25543 | 3'UTR | 1199 | GTCAGCAAATGCGTAAGG | 73 | 190 |

As shown in Table 25, SEQ ID NOs 152, 158, 160, 163, 165, 167, 171, 172, 173, 175, 177, 178, 180, 181, 182, 183, 184, 185 and 190 demonstrated at least 30% inhibition of RhoG expression in this experiment and are therefore preferred.

Example 20

Human Rac1 Oligonucleotide Sequences

Antisense oligonucleotides were designed to target human Rac1. Target sequence data are from the Rac1 cDNA sequence published by Didsbury, J., et al. (*J. Biol. Chem.* 1989, 264, 16378–16382); Genbank accession number M29870, provided herein as SEQ ID NO: 191. Oligonucleotides were synthesized primarily with phosphorothioate linkages. Oligonucleotide sequences are shown in Table 26.

Cells were cultured, treated with oligonucleotides, and mRNA was isolated and quantitated as described in Example 2. A 45-mer antisense oligonucleotide to Rac1 (5'-ATAGAATGTGAGTCTGAACTCTTACATTTAGAACA AACAAAACCT-3' SEQ ID NO. 192) was used as a probe as described in Didsbury, J., et al. (*J. Biol. Chem.* 1989, 264, 16378–16382).

An initial screen of Rac1 specific antisense oligonucleotides was performed using a oligonucleotide concentration of 300 nM.

Results are shown in Table 27. Oligonucleotides 16052 (SEQ ID NO. 195), 16056 (SEQ ID NO. 199), 16058 (SEQ ID NO. 201), 16062 (SEQ ID NO. 204) and 16063 (SEQ ID NO. 205) gave better than 50% inhibition of Rac1 mRNA levels. Oligonucleotides 16052 (SEQ ID NO. 195), 16058 (SEQ ID NO. 201) and 16062 (SEQ ID NO. 204) gave better than 75% inhibition.

204) and 16143 SEQ ID NO. 206) were chosen for dose response studies. Oligonucleotide 16057 (SEQ ID NO. 200) was chosen as a negative control because it was inactive in the initial screen. Results are shown in Table 28. Oligonucleotides 16050, 16052, 16058 and 16062 inhibited Rac1 mRNA expression in a dose dependent manner with maximum expression of 65% to 82%.

The specificity of oligonucleotides 16052 and 16058 was tested using scrambled controls. Results are shown in Table 29. Both sequences inhibited Rac1 mRNA expression in a dose dependent manner and were significantly better than their scrambled controls.

TABLE 26

Nucleotide Sequences of Rac-1 Phosphorothioate Oligonucleotides

| ISIS NO. | NUCLEOTIDE SEQUENCE (5' -> 3') | SEQ ID NO: | TARGET GENE NUCLEOTIDE CO-ORDINATES[1] | GENE TARGET REGION |
|---|---|---|---|---|
| 16050 | CAAATGATGCAGGACTCACA | 193 | 0252–0271 | Coding |
| 16051 | CACCACCACACACTTGATG | 194 | 0009–0027 | Coding |
| 16052 | ATAAGCCCAGATTCACCG | 195 | 0149–0166 | Coding |
| 16053 | TGTTTGCGGATAGGATAGG | 196 | 0207–0225 | Coding |
| 16054 | GCTTCTTCTCCTTCAGTTTCTC | 197 | 0379–0400 | Coding |
| 16055 | CAGCACCAATCTCCTTAGC | 198 | 0436–0454 | Coding |
| 16056 | CTCTTCCTCTTCTTCACGG | 199 | 0542–0560 | Coding |
| 16057 | CCTAAGATCAAGTTTAGTTC | 200 | 0341–0360 | Coding |
| 16058 | CGCACCTCAGGATACCACTT | 201 | 0286–0305 | Coding |
| 16059 | ATCTACCATAACATTGGCAG | 202 | 0122–0141 | Coding |
| 16060 | TAATTGTCAAAGACAGTAGG | 203 | 0100–0119 | Coding |
| 16062 | GAGCGCCGAGCACTCCAGGT | 204 | 0461–0480 | Coding |
| 16063 | GTCAAACACTGTCTTGAGGC | 205 | 0491–0510 | Coding |
| 16143 | ATAGAATGTGAGTCTGAACT | 206 | unknown[3] | 3'-UTR |
| 16144 | CTTACATTTAGAACAAACAAAACCT | 207 | unknown[3] | 3'-UTR |
| 16849 | CCCAGCTAAGAATTCCGCTC | 208 | 16058 control | |
| 16850 | TAAACGCCGAATCTACGC | 209 | 16052 control | |

[1]all linkages are phosphorothioate linkages.
[2]Co-ordinates from Genbank Accession No. M29870, locus name "HUMRACA" SEQ ID NO. 191.
[3]These oligonucleotides were designed based on a probe to the 3'-UTR region of Rac1 (Didsbury, J., et al., J. Biol. Chem. 1989, 264, 16378–16382).

TABLE 27

Activities of Phosphorothioate Oligonucleotides Targeted to Human Rac1

| ISIS No: | SEQ ID NO: | GENE TARGET REGION | % mRNA EXPRESSION | % mRNA INHIBITION |
|---|---|---|---|---|
| LIPOFECTIN only | — | — | 100.0% | 0.0% |
| 16051 | 194 | Coding | 77.1% | 22.9% |
| 16052 | 195 | Coding | 3.7% | 96.3% |
| 16053 | 196 | Coding | 68.4% | 31.6% |
| 16054 | 197 | Coding | 67.6% | 32.4% |
| 16055 | 198 | Coding | 70.8% | 29.2% |
| 16056 | 199 | Coding | 48.0% | 52.0% |
| 16057 | 200 | Coding | 97.3% | 2.7% |
| 16058 | 201 | Coding | 22.2% | 77.8% |
| 16059 | 202 | Coding | 57.7% | 42.3% |
| 16060 | 203 | Coding | 91.6% | 8.4% |
| 16062 | 204 | Coding | 21.7% | 78.3% |
| 16063 | 205 | Coding | 32.4% | 67.6% |
| 16143 | 206 | 3'-UTR | 56.1% | 43.9% |
| 16144 | 207 | 3'-UTR | 72.9% | 27.1% |

Example 21

Dose Response and Specificity of Antisense Oligonucleotide Effects on Human Rac1 mRNA Levels in A549 Cells Oligonucleotides 16050 (SEQ ID NO. 193), 16052 (SEQ ID No. 195), 16058 (SEQ ID NO. 201), 16062 (SEQ ID NO.

TABLE 28

Dose Response of A549 Cells to Rac1 Antisense Oligonucleotides (ASOs)

| ISIS # | SEQ ID NO: | ASO Gene Target | Dose | % mRNA Expression | % mRNA Inhibition |
|---|---|---|---|---|---|
| control | — | LIPOFECTIN only | — | 100% | 0% |
| 16050 | 193 | coding | 75 nM | 71.1% | 28.9% |
| 16050 | 193 | " | 150 nM | 53.6% | 46.4% |
| 16050 | 193 | " | 300 nM | 33.6% | 66.4% |
| 16052 | 195 | coding | 75 nM | 68.2% | 31.8% |
| 16052 | 195 | " | 150 nM | 40.5% | 59.5% |
| 16052 | 195 | " | 300 nM | 28.3% | 71.7% |
| 16057 | 200 | coding | 75 nM | 81.7% | 18.3% |
| 16057 | 200 | " | 150 nM | 80.2% | 19.8% |
| 16057 | 200 | " | 300 nM | 85.8% | 14.2% |

TABLE 28-continued

Dose Response of A549 Cells to Rac1 Antisense Oligonucleotides (ASOs)

| ISIS # | SEQ ID NO: | ASO Gene Target | Dose | % mRNA Expression | % mRNA Inhibition |
|---|---|---|---|---|---|
| 16058 | 201 | coding | 75 nM | 60.1% | 39.9% |
| 16058 | 201 | " | 150 nM | 42.9% | 57.1% |
| 16058 | 201 | " | 300 nM | 17.7% | 82.3% |
| 16062 | 204 | coding | 75 nM | 50.5% | 49.5% |
| 16062 | 204 | " | 150 nM | 40.2% | 59.8% |
| 16062 | 204 | " | 300 nM | 25.2% | 74.8% |
| 16143 | 206 | 3'-UTR | 75 nM | 294.8% | — |
| 16143 | 206 | " | 150 nM | 100.8% | — |
| 16143 | 206 | " | 300 nM | 88.6% | 11.4% |

TABLE 29

Specificity of Rac1 Antisense Oligonucleotides (ASOs) in A549 Cells

| ISIS # | SEQ ID NO: | ASO Gene Target | Dose | % mRNA Expression | % mRNA Inhibition |
|---|---|---|---|---|---|
| control | — | LIPOFECTIN only | — | 100% | 0% |
| 16052 | 195 | coding | 75 nM | 86.6% | 13.4% |
| 16052 | 195 | " | 150 nM | 52.8% | 47.2% |
| 16052 | 195 | " | 300 nM | 18.5% | 81.5% |
| 16850 | 209 | control | 75 nM | 88.9% | 11.1% |
| 16850 | 209 | " | 150 nM | 97.2% | 2.8% |
| 16850 | 209 | " | 300 nM | 107.4% | — |
| 16058 | 201 | coding | 75 nM | 82.7% | 17.3% |
| 16058 | 201 | " | 150 nM | 36.8% | 63.2% |
| 16058 | 201 | " | 300 nM | 21.1% | 78.9% |
| 16849 | 208 | control | 75 nM | 90.7% | 9.3% |
| 16849 | 208 | " | 150 nM | 70.2% | 29.8% |
| 16849 | 208 | " | 300 nM | 68.2% | 31.8% |

Example 22
Design and Testing of Chimeric (Deoxy Gapped) 2'-O-methoxyethyl Rac1 Antisense Oligonucleotides on Rac1 mRNA Levels in A549 Cells Oligonucleotides targeted to Rac1 were synthesized as a uniformly phosphorothioate or mixed phosphorothioate/phosphodiester chimeric oligonucleotides having variable regions of 2'-methoxyethyl (2'-MOE) nucleotides and deoxynucleotides. All 2'-MOE cytosines were 5-methyl-cytosines. Additionally, some oligonucleotides were synthesized with deoxycytosines as 5-methyl-cytosines. Additional oligonucleotides were synthesized, with similar chemistries, as scrambled controls. Oligonucleotide sequences and chemistries are shown in Tables 30 and 31. A dose response experiment was performed using a number of these oligonucleotides as described in Example 3.

Results are shown in Table 32. All of the chimeric oligonucleotides tested showed a dose dependent effect and showed inhibition of Rac mRNA levels comparable to that of the phosphorothioate oligodeoxynucleotide.

TABLE 30

Nucleotide Sequences of Rac1 Gapmer Oligonucleotides

| ISIS NO. | NUCLEOTIDE SEQUENCE (5' -> 3') | SEQ ID NO: | TARGET GENE NUCLEOTIDE CO-ORDINATES[1] | GENE TARGET REGION |
|---|---|---|---|---|
| 16899 | ATAAGCCCAGATTCACCG | 195 | 0149–0166 | Coding |
| 16900 | CAAATGATGCAGGACTCACA | 193 | 0252–0271 | Coding |
| 16901 | CGCACCTCAGGATACCACTT | 201 | 0286–0305 | Coding |
| 17161 | ATAAGCCCAGATTCACCG | 195 | 0149–0166 | Coding |
| 17162 | ATAAGCCCAGATTCACCG | 195 | 0149–0166 | Coding |
| 17163 | ATAAGCCCAGATTCACCG | 195 | 0149–0166 | Coding |
| 17164 | ATAAGCCCAGATTCACCG | 195 | 0149–0166 | Coding |
| 18540 | ATAAGCCCTGATTCACCG | 210 | 16899 | mismatch |
| 18541 | ATACGCCCTGATTCACCG | 211 | 16899 | mismatch |
| 18542 | ATACGCCCTGATTAACCG | 212 | 16899 | mismatch |
| 18549 | TAAACGCCGAATCTACGC | 213 | 16899 | control |

[1]Emboldened residues are 2'-methoxyethoxy residues (others are 2'-deoxy-). All 2'-methoxyethoxy cytidines are 5-methyl-cytidines; all linkages are phosphorothioate linkages.
[2]Co-ordinates from Genbank Accession No. M29870, locus name "HUMRACA" SEQ ID NO. 191.

TABLE 31

Nucleotide Sequences of Rac1 Mixed Backbone Oligonucleotides

| ISIS NO. | NUCLEOTIDE SEQUENCE (5' -> 3') | SEQ ID NO: | TARGET GENE NUCLEOTIDE CO-ORDINATES[1] | GENE TARGET REGION |
|---|---|---|---|---|
| 17814 | ToAoAoAoCoGoCoCoGsAsAsTsCsTsAsCsGsC | 213 | 16899 | control |
| 17815 | AoToAoAoGoCoCoCoAsGsAsTsTsCsAsCsCsG | 195 | 0149–0166 | Coding |
| 17816 | CoAoAoAoToGsAsTsGsCsAsGsGsAsCsToCoAoCoA | 193 | 0252–0271 | Coding |
| 17817 | AoAoAoCoToGsCsTsGsAsAsGsTsAsCsGoCoAoCoA | 214 | 17816 | control |
| 24686 | ToAoAoAoCoGoCoCoGoAoAoToCoToAoCoGoC | 213 | 16899 | control |
| 24687 | TsAsAsAsCsGsCsCsGsAsAsTsCsTsAsCsGsC | 213 | 16899 | control |

[1]Emboldened residues are 2'-methoxyethoxy residues (others are 2'-deoxy-). All 2'-methoxyethoxy cytidines and 2'-deoxy cytidines are 5-methyl-cytidines; "s" linkages are phosphorothioate linkages, "o" linkages are phosphodiester linkages.
[2]Co-ordinates from Genbank Accession No. M29870, locus name "HUMRACA" SEQ ID NO. 191.

TABLE 32

Dose Response of A549 Cells to Rac1 Antisense Gapmer Oligonucleotides (ASOs)

| ISIS # | SEQ ID NO: | ASO Gene Target | Dose | % mRNA Expression | % mRNA Inhibition |
|---|---|---|---|---|---|
| control | — | LIPOFECTIN only | — | 100 | 0.0% |
| 16899 | 195 | coding | 75 nM | 79.9% | 20.1% |
| " | " | " | 150 nM | 40.8% | 59.2% |
| " | " | " | 300 nM | 21.8% | 78.2% |
| 17161 | 195 | coding | 75 nM | 31.3% | 68.7% |
| " | " | " | 150 nM | 16.9% | 83.1% |
| " | " | " | 300 nM | 12.3% | 87.7% |
| 17162 | 195 | coding | 75 nM | 89.2% | 10.8% |
| " | " | " | 150 nM | 63.0% | 37.0% |
| " | " | " | 300 nM | 18.4% | 81.6% |
| 17163 | 195 | coding | 75 nM | 93.4% | 6.6% |
| " | " | " | 150 nM | 67.3% | 32.7% |
| " | " | " | 300 nM | 34.4% | 65.6% |
| 17164 | 195 | coding | 75 nM | 94.7% | 5.3% |
| " | " | " | 150 nM | 65.9% | 34.1% |
| " | " | " | 300 nM | 36.2% | 63.8% |

Example 23
Human cdc42 Chimeric (Deoxy Gapped) 2'-O-methoxyethyl oligonucleotide Sequences Antisense oligonucleotides were designed to target human cdc42. Target sequence data are from the cdc42 cDNA sequence published by Shinjo, K. et al. (*Proc. Natl. Acad. Sci. U.S.A.* 1990, 87, 9853–9857); Genbank accession number M57298, provided herein as SEQ ID NO: 215. Oligonucleotides were synthesized as uniformly phosphorothioate chimeric oligonucleotides having a centered deoxy gap of eight nucleotides flanked by 2'-O-methoxyethyl (2'-MOE) regions. All 2'-MOE cytosines were 5-methyl-cytosines. Oligonucleotide sequences are shown in Table 33.

A549 cells were cultured and treated with oligonucleotide as described in Example 2. Quantitation of cdc42 mRNA levels was determined by real-time PCR (RT-PCR) as described in previous examples.

For cdc42 the PCR primers were:
Forward: 5'-TTCAGCAATGCAGACAATTAAGTGT-3' SEQ ID NO. 216
Reverse: 5'-TGTTGTGTAGGATATCAGGAGACATGT-3' SEQ ID NO. 217
and the PCR probe was: FAM-TTGTGGGCGATGGTGCTGTTGGTA-TAMRA (SEQ ID NO. 218) where FAM or JOE (PE-Applied Biosystems, Foster City, Calif.) is the fluorescent reporter dye) and TAMRA (PE-Applied Biosystems, Foster City, Calif.) is the quencher dye.

For GAPDH the PCR primers were:
Forward primer: 5'-GAAGGTGAAGGTCGGAGTC-3' SEQ ID NO. 65
Reverse primer: 5'-GAAGATGGTGATGGGATTTC-3' SEQ ID NO. 66
and the PCR probe was: 5' JOE-CAAGCTTCCCGTTCTCAGCC-TAMRA 3' (SEQ ID NO. 67) where FAM or JOE (PE-Applied Biosystems, Foster City, Calif.) is the fluorescent reporter dye) and TAMRA (PE-Applied Biosystems, Foster City, Calif.) is the quencher dye.

Results are shown in Table 34. All oligonucleotides tested gave greater than 40% inhibition of cdc42 mRNA expression.

TABLE 33

Nucleotide Sequences of cdc42 oligonucleotides

| ISIS NO. | NUCLEOTIDE SEQUENCE (5' -> 3') | SEQ ID NO: | TARGET GENE NUCLEOTIDE CO-ORDINATES[1] | GENE TARGET REGION |
|---|---|---|---|---|
| 17208 | TAATTGTCTGCATTGCTGAA | 219 | 0063–0082 | AUG |
| 17209 | TTACCAACAGCACCATCGCC | 220 | 0097–0116 | Coding |
| 17210 | CCACCAATCATAACTGTGAC | 221 | 0193–0212 | Coding |
| 17211 | GTGGATAACTCAGCGGTCGT | 222 | 0270–0289 | Coding |
| 17212 | GAAGATGGAGAGACCACTGA | 223 | 0316–0335 | Coding |
| 17213 | GTGAGTTATCTCAGGCACCC | 224 | 0359–0378 | Coding |
| 17214 | GCTTCTGTTTGTTCTTGGCA | 225 | 0456–0475 | Coding |
| 17215 | TGACAGCCTTCAGGTCACGG | 226 | 0507–0526 | Coding |
| 17216 | CACCTGCGGCTCTTCTTCGG | 227 | 0613–0632 | Coding |
| 17217 | TTGTCTCACACGAGTGCATG | 228 | 0774–0793 | 3'-UTR |
| 17218 | TTCTGACAATACAATTACTC | 229 | 0844–0863 | 3'-UTR |
| 17219 | TTACAGAGTCATCCACAAGC | 230 | 0961–0980 | 3'-UTR |
| 20457 | CGATAGTC̲T̲C̲C̲A̲CGTGAGGC | 231 | 17215 control | |
| 21668 | CGATAGTCTCCACGTGAGGC | 231 | 17215 control | |
| 21917 | GTAACGCTCCTATGCCAGG | 232 | 17215 control | |
| 21918 | AGACTGACTGCTCGTCGCGA | 233 | 17215 control | |

[1]Emboldened residues are 2'-methoxyethoxy residues (others are 2'-deoxy-). All 2'-methoxyethoxy cytidines are 5-methyl-cytidines, underlined "C" residues are 5-methyl-cytidines; all linkages are phosphorothioate linkages.
[2]Co-ordinates from Genbank Accession No. M57298, locus name "HUMGPG25K" SEQ ID NO. 215.

TABLE 34

Activities of Phosphorothioate Oligonucleotides Targeted to Human Cdc42

| ISIS No: | SEQ ID NO: | GENE TARGET REGION | % mRNA EXPRESSION | % mRNA INHIBITION |
|---|---|---|---|---|
| LIPOFECTIN only | — | — | 100% | 0% |
| 17208 | 219 | AUG | 40.6% | 59.4% |
| 17209 | 220 | Coding | 43.4% | 56.6% |
| 17210 | 221 | Coding | 55.4% | 44.6% |
| 17211 | 222 | Coding | 25.5% | 74.5% |
| 17212 | 223 | Coding | 31.1% | 68.9% |
| 17213 | 224 | Coding | 14.0% | 86.0% |
| 17214 | 225 | Coding | 27.4% | 72.6% |
| 17215 | 226 | Coding | 16.9% | 83.1% |
| 17216 | 227 | Coding | 26.0% | 74.0% |
| 17217 | 228 | 3'-UTR | 28.4% | 71.6% |
| 17218 | 229 | 3'-UTR | 17.2% | 82.8% |
| 17219 | 230 | 3'-UTR | 20.2% | 79.8% |

Example 24
Dose Response of Antisense Oligonucleotide Effects cdc42 mRNA Levels in A549 Cells Oligonucleotides 17213 (SEQ ID NO. 224), 17215 (SEQ ID No. 226), 17218 (SEQ ID NO. 229), and 17219 (SEQ ID NO. 230) were chosen for dose response studies. Results are shown in Table 35.

TABLE 35

Dose Response of A549 Cells to Cdc42 Antisense Oligonucleotides (ASOs)

| ISIS # | SEQ ID NO: | ASO Gene Target | Dose | % mRNA Expression | % mRNA Inhibition |
|---|---|---|---|---|---|
| control | — | LIPOFECTIN only | — | 100 | 0% |

TABLE 35-continued

Dose Response of A549 Cells to Cdc42 Antisense Oligonucleotides (ASOs)

| ISIS # | SEQ ID NO: | ASO Gene Target | Dose | % mRNA Expression | % mRNA Inhibition |
|---|---|---|---|---|---|
| 17213 | 224 | coding | 75 nM | 158% | — |
| 17213 | " | " | 300 nM | 16% | 84% |
| 17215 | 226 | coding | 75 nM | 90% | 10% |
| 17215 | " | " | 300 nM | 21% | 79% |
| 17218 | 229 | 3'-UTR | 75 nM | 53% | 47% |
| 17218 | " | " | 300 nM | 38% | 62% |
| 17219 | 230 | 3'-UTR | 75 nM | 102% | — |
| 17219 | " | " | 300 nM | 41% | 59% |

Example 25

Additional cdc42 Chimeric Oligonucleotides

Oligonucleotides having SEQ ID NO: 226 were synthesized as mixed phosphorothioate/phosphodiester chimeric oligonucleotides having variable wing regions of 2'-O-methoxyethyl (2'-MOE) nucleotides and a central stretch of nine deoxynucleotides. All 2'-MOE cytosines were 5-methyl-cytosines. Oligonucleotide sequences and chemistries are shown in Table 36.

TABLE 36

Nucleotide Sequence of 17215 Analog

| ISIS NO. | NUCLEOTIDE SEQUENCE (51 ->31) | SEQ ID NO: | TARGET GENE NUCLEOTIDE CO-ORDINATES[1] | GENE TARGET REGION |
|---|---|---|---|---|
| 22276 | ToGoAoCoAoGsCsCsTsTsCsAsGsGsTsCoAoCoGoG | 226 | 0507–0526 | Coding |
| 22277 | CoGoAoToAoGsTsCsTsCsCsAsCsGsTsGoAoGoGoC | 231 | 22276 control | |

[1]Emboldened residues are 2'-methoxyethoxy residues (others are 2'-deoxy). All 2'-methoxyethoxy cytidines are 5-methyl-cytidines; "s" linkages are phosphorothioate linkages, "o" linkages are phosphodiester linkages.
[2]Co-ordinates from Genbank Accession No. M57298, locus name "HUMGPG25K" SEQ ID NO. 215.

What is claimed is:

1. An antisense compound 8 to 30 nucleobases in length targeted to an nucleic acid molecule encoding human cdc42 that comprises at least an 8 nucleobase portion of SEQ ID NO: 219, 220, 221, 222, 223, 224, 225, 226, 227, 228, 229 or 230, and wherein said antisense compound inhibits expression of human cdc42.

2. The antisense compound of claim 1, which is an antisense oligonucleotide.

3. The antisense compound of claim 2, wherein the oligonucleotide comprises at least one modified internucleoside linkage.

4. The antisense compound of claim 3, wherein the modified internucleoside linkage is a phosphorothioate linkage.

5. The antisense compound of claim 2 wherein the oligonucleotide comprises at least one modified sugar moiety.

6. The antisense compound of claim 5 wherein the modified sugar moiety is a 2'-O-methoxyethyl sugar moiety.

7. The antisense compound of claim 2 wherein the oligonucleotide comprises at least one modified nucleobase.

8. The antisense compound of claim 7 wherein the modified nucleobase is a 5-methylcytosine.

9. The antisense compound of claim 2, wherein the oligonucleotide is a chimeric oligonucleotide.

10. A composition comprising the antisense compound of claim 2, and a pharmaceutically acceptable carrier or diluent.

11. The composition of claim 10, further comprising a colloidal dispersion system.

12. The composition of claim 2, wherein the antisense compound is an antisense oligonucleotide.

13. A method of inhibiting the expression of human cdc42 in human cells and tissues comprising contacting said cells or tissues in vitro with the antisense compound of claim 1, is so that expression of said human cdc42 is inhibited.

* * * * *

SEQUENCE LISTING

```
<160> NUMBER OF SEQ ID NOS: 233

<210> SEQ ID NO 1
<211> LENGTH: 1074
<212> TYPE: DNA
<213> ORGANISM: Homo sapiens

<400> SEQUENCE: 1
gaattcgggc taccctcgcc ccgcccgcgg tcctccgtcg gttctctcat t agtccacgg    60 tctggtcttc agctacccgc cttcgtctcc gagtttgcga ctcgcgggac c ggcgtcccc   120 ggcgcgaaga ggctggactc ggattcgttg cctgagcaat ggctgccatc c ggaagaaac   180 tggtgattgt tggtgatgga gcctgtggaa agacatgctt gctcatagtc t tcagcaagg   240 accagttccc agaggtgtat gtgcccacag tgtttgagaa ctatgtggca g atatcgagg   300 tggatggaaa gcaggtagag ttggctttgt gggacacagc tgggcaggaa g attatgatc   360 gcctgaggcc cctctcctac ccagataccg atgttatact gatgtgtttt t ccatcgaca   420 gccctgatag tttagaaaac atcccagaaa agtggacccc agaagtcaag c atttctgtc   480 ccaacgtgcc catcatcctg gttgggaata agaaggatct tcggaatgat g agcacacaa   540 ggcgggagct agccaagatg aagcaggagc cggtgaaacc tgaagaaggc a gagatatgg   600 caaacaggat tggcgctttt gggtacatgg agtgttcagc aaagaccaaa g atggagtga   660 gagaggtttt tgaaatggct acgagagctg ctctgcaagc tagacgtggg a agaaaaaat   720
```

```
ctggttgcct tgtcttgtga aaccttgctg caagcacagc ccttatgcgg t taattttga    780 agtgctgttt attaatctta gtgtatgatt actggccttt ttcatttatc t ataatttac    840 ctaagattac aaatcagaag tcatcttgct accagtattt agaagccaac t atgattatt    900 aacgatgtcc aacccgtctg gcccaccagg gtccttttga cactgctcta a cagccctcc    960 tctgcactcc cacctgacac accaggcgct aattcaagga atttcttaac t tcttgcttc   1020 tttctagaaa gagaaacagt tggtaacttt tgtcaattag gctgtaacta c ttt         1074
```

<210> SEQ ID NO 2
<211> LENGTH: 19
<212> TYPE: DNA
<213> ORGANISM: Artificial Sequence
<220> FEATURE:
<223> OTHER INFORMATION: Description of Artificial Sequence:Synthetic

<400> SEQUENCE: 2
tgcaagcaca gcccttatg                                                    19

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence:Synthetic

<400> SEQUENCE: 3
tgtcaaaagg accctggtg                                                    19

<210> SEQ ID NO 4
<211> LENGTH: 18
<212> TYPE: DNA
<213> ORGANISM: Artificial Sequence
<220> FEATURE:
<223> OTHER INFORMATION: Description of Artificial Sequence:Synthetic

<400> SEQUENCE: 4
agtcgcaaac tcggagac                                                     18

<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence:Synthetic

<400> SEQUENCE: 5
ttgctcaggc aacgaatc                                                     18

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence:Synthetic

<400> SEQUENCE: 6
ctgaagacta tgagcaagca tg                                                22

<210> SEQ ID NO 7
<211> LENGTH: 19
<212> TYPE: DNA
<213> ORGANISM: Artificial Sequence
<220> FEATURE:

-continued

<223> OTHER INFORMATION: Description of Artificial Sequence:Synthetic

<400> SEQUENCE: 7
ctcatcattc cgaagatcc                                              19

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence:Synthetic

<400> SEQUENCE: 8
ccaatcctgt ttgccatatc tc                                          22

<210> SEQ ID NO 9
<211> LENGTH: 22
<212> TYPE: DNA
<213> ORGANISM: Artificial Sequence
<220> FEATURE:
<223> OTHER INFORMATION: Description of Artificial Sequence:Synthetic

<400> SEQUENCE: 9
ccatctttgg tctttgctga ac                                          22

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence:Synthetic

<400> SEQUENCE: 10
gcagagcagc tctcgtagcc a                                           21

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 11
tcacaagaca aggcaaccag                                             20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 12
aggccagtaa tcatacacta                                             20

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 13
gttggcttct aaatactggt                                             20

```
<210> SEQ ID NO 14
<211> LENGTH: 20
<212> TYPE: DNA
<213> ORGANISM: Artificial Sequence
<220> FEATURE:
<223> OTHER INFORMATION: Description of Artificial  Sequence:Synthetic

<400> SEQUENCE: 14
ggctgttaga gcagtgtcaa                                              20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial  Sequence:Synthetic

<400> SEQUENCE: 15
agcgcctggt gtgtcaggtg                                              20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial  Sequence:Synthetic

<400> SEQUENCE: 16
tagttacagc ctaattgaca                                              20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial  Sequence:Synthetic

<400> SEQUENCE: 17
ggcacctgtt gggtgagctg                                              20

<210> SEQ ID NO 18
<211> LENGTH: 22
<212> TYPE: DNA
<213> ORGANISM: Artificial Sequence
<220> FEATURE:
<223> OTHER INFORMATION: Description of Artificial  Sequence:Synthetic

<400> SEQUENCE: 18
acactcttgc ttaccgtacc tt                                           22

<210> SEQ ID NO 19
<211> LENGTH: 20
<212> TYPE: DNA
<213> ORGANISM: Artificial Sequence
<220> FEATURE:
<223> OTHER INFORMATION: Description of Artificial  Sequence:Synthetic

<400> SEQUENCE: 19
tgcggtaagt gcggtatcaa                                              20

<210> SEQ ID NO 20
<211> LENGTH: 19
<212> TYPE: DNA
<213> ORGANISM: Artificial Sequence
<220> FEATURE:
<223> OTHER INFORMATION: Description of Artificial  Sequence:Synthetic
```

```
<400> SEQUENCE: 20
gtcgttagtc gaaatgagg                                                        19

<210> SEQ ID NO 21
<211> LENGTH: 20
<212> TYPE: DNA
<213> ORGANISM: Artificial Sequence
<220> FEATURE:
<223> OTHER INFORMATION: Description of Artificial  Sequence:Synthetic

<400> SEQUENCE: 21
agcttgtgaa cgagtgtcga                                                       20

<210> SEQ ID NO 22
<211> LENGTH: 20
<212> TYPE: DNA
<213> ORGANISM: Artificial Sequence
<220> FEATURE:
<223> OTHER INFORMATION: Description of Artificial  Sequence:Synthetic

<400> SEQUENCE: 22
tgcagttggc agagtctgaa                                                       20

<210> SEQ ID NO 23
<211> LENGTH: 18
<212> TYPE: DNA
<213> ORGANISM: Artificial Sequence
<220> FEATURE:
<223> OTHER INFORMATION: Description of Artificial  Sequence:Synthetic

<400> SEQUENCE: 23
agagaaccga cggaggac                                                         18

<210> SEQ ID NO 24
<211> LENGTH: 18
<212> TYPE: DNA
<213> ORGANISM: Artificial Sequence
<220> FEATURE:
<223> OTHER INFORMATION: Description of Artificial  Sequence:Synthetic

<400> SEQUENCE: 24
gtggactaat gagagaac                                                         18

<210> SEQ ID NO 25
<211> LENGTH: 18
<212> TYPE: DNA
<213> ORGANISM: Artificial Sequence
<220> FEATURE:
<223> OTHER INFORMATION: Description of Artificial  Sequence:Synthetic

<400> SEQUENCE: 25
gaccgtggac taatgaga                                                         18

<210> SEQ ID NO 26
<211> LENGTH: 18
<212> TYPE: DNA
<213> ORGANISM: Artificial Sequence
<220> FEATURE:
<223> OTHER INFORMATION: Description of Artificial  Sequence:Synthetic

<400> SEQUENCE: 26
agctgaagac cagaccgt                                                         18

<210> SEQ ID NO 27
<211> LENGTH: 18
```

```
<212> TYPE: DNA
<213> ORGANISM: Artificial Sequence
<220> FEATURE:
<223> OTHER INFORMATION: Description of Artificial  Sequence:Synthetic

<400> SEQUENCE: 27
aatccgagtc cagcctct                                                    18

<210> SEQ ID NO 28
<211> LENGTH: 18
<212> TYPE: DNA
<213> ORGANISM: Artificial Sequence
<220> FEATURE:
<223> OTHER INFORMATION: Description of Artificial  Sequence:Synthetic

<400> SEQUENCE: 28
aacgaatccg agtccagc                                                    18

<210> SEQ ID NO 29
<211> LENGTH: 18
<212> TYPE: DNA
<213> ORGANISM: Artificial Sequence
<220> FEATURE:
<223> OTHER INFORMATION: Description of Artificial  Sequence:Synthetic

<400> SEQUENCE: 29
tcaggcaacg aatccgag                                                    18

<210> SEQ ID NO 30
<211> LENGTH: 18
<212> TYPE: DNA
<213> ORGANISM: Artificial Sequence
<220> FEATURE:
<223> OTHER INFORMATION: Description of Artificial  Sequence:Synthetic

<400> SEQUENCE: 30
caccaacaat caccagtt                                                    18

<210> SEQ ID NO 31
<211> LENGTH: 18
<212> TYPE: DNA
<213> ORGANISM: Artificial Sequence
<220> FEATURE:
<223> OTHER INFORMATION: Description of Artificial  Sequence:Synthetic

<400> SEQUENCE: 31
aagactatga gcaagcat                                                    18

<210> SEQ ID NO 32
<211> LENGTH: 18
<212> TYPE: DNA
<213> ORGANISM: Artificial Sequence
<220> FEATURE:
<223> OTHER INFORMATION: Description of Artificial  Sequence:Synthetic

<400> SEQUENCE: 32
atacacctct gggaactg                                                    18

<210> SEQ ID NO 33
<211> LENGTH: 18
<212> TYPE: DNA
<213> ORGANISM: Artificial Sequence
<220> FEATURE:
<223> OTHER INFORMATION: Description of Artificial  Sequence:Synthetic

<400> SEQUENCE: 33
```
acatagttct caaacact                                                 18

<210> SEQ ID NO 34
<211> LENGTH: 18
<212> TYPE: DNA
<213> ORGANISM: Artificial Sequence
<220> FEATURE:
<223> OTHER INFORMATION: Description of Artificial Sequence:Synthetic

<400> SEQUENCE: 34
actctacctg ctttccat                                                 18

<210> SEQ ID NO 35
<211> LENGTH: 18
<212> TYPE: DNA
<213> ORGANISM: Artificial Sequence
<220> FEATURE:
<223> OTHER INFORMATION: Description of Artificial Sequence:Synthetic

<400> SEQUENCE: 35
cacaaagcca actctacc                                                 18

<210> SEQ ID NO 36
<211> LENGTH: 18
<212> TYPE: DNA
<213> ORGANISM: Artificial Sequence
<220> FEATURE:
<223> OTHER INFORMATION: Description of Artificial Sequence:Synthetic

<400> SEQUENCE: 36
aacatcggta tctgggta                                                 18

<210> SEQ ID NO 37
<211> LENGTH: 18
<212> TYPE: DNA
<213> ORGANISM: Artificial Sequence
<220> FEATURE:
<223> OTHER INFORMATION: Description of Artificial Sequence:Synthetic

<400> SEQUENCE: 37
ttctgggatg ttttctaa                                                 18

<210> SEQ ID NO 38
<211> LENGTH: 18
<212> TYPE: DNA
<213> ORGANISM: Artificial Sequence
<220> FEATURE:
<223> OTHER INFORMATION: Description of Artificial Sequence:Synthetic

<400> SEQUENCE: 38
ggacagaaat gcttgact                                                 18

<210> SEQ ID NO 39
<211> LENGTH: 18
<212> TYPE: DNA
<213> ORGANISM: Artificial Sequence
<220> FEATURE:
<223> OTHER INFORMATION: Description of Artificial Sequence:Synthetic

<400> SEQUENCE: 39
gtgctcatca ttccgaag                                                 18

<210> SEQ ID NO 40
<211> LENGTH: 18
<212> TYPE: DNA
<213> ORGANISM: Artificial Sequence

```
<220> FEATURE:
<223> OTHER INFORMATION: Description of Artificial  Sequence:Synthetic

<400> SEQUENCE: 40
cttgtgtgct catcattc                                                 18

<210> SEQ ID NO 41
<211> LENGTH: 18
<212> TYPE: DNA
<213> ORGANISM: Artificial Sequence
<220> FEATURE:
<223> OTHER INFORMATION: Description of Artificial  Sequence:Synthetic

<400> SEQUENCE: 41
tagctcccgc cttgtgtg                                                 18

<210> SEQ ID NO 42
<211> LENGTH: 18
<212> TYPE: DNA
<213> ORGANISM: Artificial Sequence
<220> FEATURE:
<223> OTHER INFORMATION: Description of Artificial  Sequence:Synthetic

<400> SEQUENCE: 42
ccaatcctgt ttgccata                                                 18

<210> SEQ ID NO 43
<211> LENGTH: 18
<212> TYPE: DNA
<213> ORGANISM: Artificial Sequence
<220> FEATURE:
<223> OTHER INFORMATION: Description of Artificial  Sequence:Synthetic

<400> SEQUENCE: 43
gtctttgctg aacactcc                                                 18

<210> SEQ ID NO 44
<211> LENGTH: 18
<212> TYPE: DNA
<213> ORGANISM: Artificial Sequence
<220> FEATURE:
<223> OTHER INFORMATION: Description of Artificial  Sequence:Synthetic

<400> SEQUENCE: 44
aaaacctctc tcactcca                                                 18

<210> SEQ ID NO 45
<211> LENGTH: 18
<212> TYPE: DNA
<213> ORGANISM: Artificial Sequence
<220> FEATURE:
<223> OTHER INFORMATION: Description of Artificial  Sequence:Synthetic

<400> SEQUENCE: 45
aagacaaggc aaccagat                                                 18

<210> SEQ ID NO 46
<211> LENGTH: 18
<212> TYPE: DNA
<213> ORGANISM: Artificial Sequence
<220> FEATURE:
<223> OTHER INFORMATION: Description of Artificial  Sequence:Synthetic

<400> SEQUENCE: 46
tttcacaaga caaggcaa                                                 18
```

<210> SEQ ID NO 47
<211> LENGTH: 18
<212> TYPE: DNA
<213> ORGANISM: Artificial Sequence
<220> FEATURE:
<223> OTHER INFORMATION: Description of Artificial Sequence:Synthetic

<400> SEQUENCE: 47
gcaaggtttc acaagaca                                               18

<210> SEQ ID NO 48
<211> LENGTH: 18
<212> TYPE: DNA
<213> ORGANISM: Artificial Sequence
<220> FEATURE:
<223> OTHER INFORMATION: Description of Artificial Sequence:Synthetic

<400> SEQUENCE: 48
attaaccgca taagggct                                               18

<210> SEQ ID NO 49
<211> LENGTH: 18
<212> TYPE: DNA
<213> ORGANISM: Artificial Sequence
<220> FEATURE:
<223> OTHER INFORMATION: Description of Artificial Sequence:Synthetic

<400> SEQUENCE: 49
taataaacag cacttcaa                                               18

<210> SEQ ID NO 50
<211> LENGTH: 18
<212> TYPE: DNA
<213> ORGANISM: Artificial Sequence
<220> FEATURE:
<223> OTHER INFORMATION: Description of Artificial Sequence:Synthetic

<400> SEQUENCE: 50
ccagtaatca tacactaa                                               18

<210> SEQ ID NO 51
<211> LENGTH: 18
<212> TYPE: DNA
<213> ORGANISM: Artificial Sequence
<220> FEATURE:
<223> OTHER INFORMATION: Description of Artificial Sequence:Synthetic

<400> SEQUENCE: 51
atgacttctg atttgtaa                                               18

<210> SEQ ID NO 52
<211> LENGTH: 18
<212> TYPE: DNA
<213> ORGANISM: Artificial Sequence
<220> FEATURE:
<223> OTHER INFORMATION: Description of Artificial Sequence:Synthetic

<400> SEQUENCE: 52
tagcaagatg acttctga                                               18

<210> SEQ ID NO 53
<211> LENGTH: 18
<212> TYPE: DNA
<213> ORGANISM: Artificial Sequence
<220> FEATURE:
<223> OTHER INFORMATION: Description of Artificial Sequence:Synthetic

```
<400> SEQUENCE: 53
ctggtagcaa gatgactt                                                  18

<210> SEQ ID NO 54
<211> LENGTH: 18
<212> TYPE: DNA
<213> ORGANISM: Artificial Sequence
<220> FEATURE:
<223> OTHER INFORMATION: Description of Artificial  Sequence:Synthetic

<400> SEQUENCE: 54
ctaaatactg gtagcaag                                                  18

<210> SEQ ID NO 55
<211> LENGTH: 18
<212> TYPE: DNA
<213> ORGANISM: Artificial Sequence
<220> FEATURE:
<223> OTHER INFORMATION: Description of Artificial  Sequence:Synthetic

<400> SEQUENCE: 55
ttggcttcta aatactgg                                                  18

<210> SEQ ID NO 56
<211> LENGTH: 18
<212> TYPE: DNA
<213> ORGANISM: Artificial Sequence
<220> FEATURE:
<223> OTHER INFORMATION: Description of Artificial  Sequence:Synthetic

<400> SEQUENCE: 56
tcatagttgg cttctaaa                                                  18

<210> SEQ ID NO 57
<211> LENGTH: 18
<212> TYPE: DNA
<213> ORGANISM: Artificial Sequence
<220> FEATURE:
<223> OTHER INFORMATION: Description of Artificial  Sequence:Synthetic

<400> SEQUENCE: 57
aataatcata gttggctt                                                  18

<210> SEQ ID NO 58
<211> LENGTH: 18
<212> TYPE: DNA
<213> ORGANISM: Artificial Sequence
<220> FEATURE:
<223> OTHER INFORMATION: Description of Artificial  Sequence:Synthetic

<400> SEQUENCE: 58 tcaaaggac cctggtgg                                                   18

<210> SEQ ID NO 59
<211> LENGTH: 18
<212> TYPE: DNA
<213> ORGANISM: Artificial Sequence
<220> FEATURE:
<223> OTHER INFORMATION: Description of Artificial  Sequence:Synthetic

<400> SEQUENCE: 59
gtgcagagga gggctgtt                                                  18

<210> SEQ ID NO 60
```

-continued

```
<211> LENGTH: 18
<212> TYPE: DNA
<213> ORGANISM: Artificial Sequence
<220> FEATURE:
<223> OTHER INFORMATION: Description of Artificial  Sequence:Synthetic

<400> SEQUENCE: 60
ccaactgttt ctctttct                                                      18

<210> SEQ ID NO 61
<211> LENGTH: 18
<212> TYPE: DNA
<213> ORGANISM: Artificial Sequence
<220> FEATURE:
<223> OTHER INFORMATION: Description of Artificial  Sequence:Synthetic

<400> SEQUENCE: 61
aagtagttac agcctaat                                                      18

<210> SEQ ID NO 62
<211> LENGTH: 19
<212> TYPE: DNA
<213> ORGANISM: Artificial Sequence
<220> FEATURE:
<223> OTHER INFORMATION: Description of Artificial  Sequence:Synthetic

<400> SEQUENCE: 62
ggctggactc ggattcgtt                                                     19

<210> SEQ ID NO 63
<211> LENGTH: 22
<212> TYPE: DNA
<213> ORGANISM: Artificial Sequence
<220> FEATURE:
<223> OTHER INFORMATION: Description of Artificial  Sequence:Synthetic

<400> SEQUENCE: 63
ccatcaccaa caatcaccag tt                                                 22

<210> SEQ ID NO 64
<211> LENGTH: 22
<212> TYPE: DNA
<213> ORGANISM: Artificial Sequence
<220> FEATURE:
<223> OTHER INFORMATION: Description of Artificial  Sequence:Synthetic

<400> SEQUENCE: 64
cctgagcaat ggctgccatc cg                                                 22

<210> SEQ ID NO 65
<211> LENGTH: 19
<212> TYPE: DNA
<213> ORGANISM: Artificial Sequence
<220> FEATURE:
<223> OTHER INFORMATION: Description of Artificial  Sequence:Synthetic

<400> SEQUENCE: 65
gaaggtgaag gtcggagtc                                                     19

<210> SEQ ID NO 66
<211> LENGTH: 20
<212> TYPE: DNA
<213> ORGANISM: Homo sapiens
<220> FEATURE:
<223> OTHER INFORMATION: Description of Artificial  Sequence:Synthetic

<400> SEQUENCE: 66
```

-continued

```
gaagatggtg atgggatttc                                           20
```

<210> SEQ ID NO 67
<211> LENGTH: 20
<212> TYPE: DNA
<213> ORGANISM: Artificial Sequence
<220> FEATURE:
<223> OTHER INFORMATION: Description of Artificial  Sequence:Synthetic

<400> SEQUENCE: 67

```
caagcttccc gttctcagcc                                           20
```

<210> SEQ ID NO 68
<211> LENGTH: 591
<212> TYPE: DNA
<213> ORGANISM: Homo sapiens
<220> FEATURE:
<223> OTHER INFORMATION: Description of Artificial  Sequence:Synthetic

<400> SEQUENCE: 68

```
atggcggcca tccgcaagaa gctggtggtg gtgggcgacg gcgcgtgtgg c aagacgtgc    60 ctgctgatcg tgttcagtaa ggacgagttc cccgaggtgt acgtgcccac c gtcttcgag   120 aactatgtgg ccgacattga ggtggacggc aagcaggtgg agctggcgct g tgggacacg   180 gcgggccagg aggactacga ccgcctgcgg ccgctctcct acccggacac c gacgtcatt   240 ctcatgtgct ctcggtgga cagccccgac tcgctggaga acatccccga g aagtgggtc   300 cccgaggtga agcacttctg tcccaatgtg cccatcatcc tggtggccaa c aaaaaagac   360 ctgcgcagcg acgagcatgt ccgcacagag ctggcccgca tgaagcagga a cccgtgcgc   420 acggatgacg gccgcgccat ggccgtgcgc atccaagcct acgactacct c gagtgctct   480 gccaagacca aggaaggcgt gcgcgaggtc ttcgagacgg ccacgcgcgc c gcgctgcag   540 aagcgctacg gctcccagaa cggctgcatc aactgctgca aggtgctatg a            591
```

<210> SEQ ID NO 69
<211> LENGTH: 18
<212> TYPE: DNA
<213> ORGANISM: Artificial Sequence
<220> FEATURE:
<223> OTHER INFORMATION: Description of Artificial  Sequence:Synthetic

<400> SEQUENCE: 69

```
ccaccaccag cttcttgc                                             18
```

<210> SEQ ID NO 70
<211> LENGTH: 18
<212> TYPE: DNA
<213> ORGANISM: Artificial Sequence
<220> FEATURE:
<223> OTHER INFORMATION: Description of Artificial  Sequence:Synthetic

<400> SEQUENCE: 70

```
ccgtcgccca ccaccacc                                             18
```

<210> SEQ ID NO 71
<211> LENGTH: 18
<212> TYPE: DNA
<213> ORGANISM: Artificial Sequence
<220> FEATURE:
<223> OTHER INFORMATION: Description of Artificial  Sequence:Synthetic

<400> SEQUENCE: 71
gcacgtcttg ccacacgc                      18

<210> SEQ ID NO 72
<211> LENGTH: 18
<212> TYPE: DNA
<213> ORGANISM: Artificial Sequence
<220> FEATURE:
<223> OTHER INFORMATION: Description of Artificial Sequence:Synthetic

<400> SEQUENCE: 72
actgaacacg atcagcag                      18

<210> SEQ ID NO 73
<211> LENGTH: 18
<212> TYPE: DNA
<213> ORGANISM: Artificial Sequence
<220> FEATURE:
<223> OTHER INFORMATION: Description of Artificial Sequence:Synthetic

<400> SEQUENCE: 73
ttactgaaca cgatcagc                      18

<210> SEQ ID NO 74
<211> LENGTH: 18
<212> TYPE: DNA
<213> ORGANISM: Artificial Sequence
<220> FEATURE:
<223> OTHER INFORMATION: Description of Artificial Sequence:Synthetic

<400> SEQUENCE: 74
ccttactgaa cacgatca                      18

<210> SEQ ID NO 75
<211> LENGTH: 18
<212> TYPE: DNA
<213> ORGANISM: Artificial Sequence
<220> FEATURE:
<223> OTHER INFORMATION: Description of Artificial Sequence:Synthetic

<400> SEQUENCE: 75
gtccttactg aacacgat                      18

<210> SEQ ID NO 76
<211> LENGTH: 18
<212> TYPE: DNA
<213> ORGANISM: Artificial Sequence
<220> FEATURE:
<223> OTHER INFORMATION: Description of Artificial Sequence:Synthetic

<400> SEQUENCE: 76
ctcgtcctta ctgaacac                      18

<210> SEQ ID NO 77
<211> LENGTH: 18
<212> TYPE: DNA
<213> ORGANISM: Artificial Sequence
<220> FEATURE:
<223> OTHER INFORMATION: Description of Artificial Sequence:Synthetic

<400> SEQUENCE: 77
aactcgtcct tactgaac                      18

<210> SEQ ID NO 78
<211> LENGTH: 18
<212> TYPE: DNA
<213> ORGANISM: Artificial Sequence

```
<220> FEATURE:
<223> OTHER INFORMATION: Description of Artificial Sequence:Synthetic

<400> SEQUENCE: 78
catagttctc gaagacgg                                                18

<210> SEQ ID NO 79
<211> LENGTH: 18
<212> TYPE: DNA
<213> ORGANISM: Artificial Sequence
<220> FEATURE:
<223> OTHER INFORMATION: Description of Artificial Sequence:Synthetic

<400> SEQUENCE: 79
tcggccacat agttctcg                                                18

<210> SEQ ID NO 80
<211> LENGTH: 18
<212> TYPE: DNA
<213> ORGANISM: Artificial Sequence
<220> FEATURE:
<223> OTHER INFORMATION: Description of Artificial Sequence:Synthetic

<400> SEQUENCE: 80
ccgtccacct caatgtcg                                                18

<210> SEQ ID NO 81
<211> LENGTH: 18
<212> TYPE: DNA
<213> ORGANISM: Artificial Sequence
<220> FEATURE:
<223> OTHER INFORMATION: Description of Artificial Sequence:Synthetic

<400> SEQUENCE: 81
aagcacatga gaatgacg                                                18

<210> SEQ ID NO 82
<211> LENGTH: 18
<212> TYPE: DNA
<213> ORGANISM: Artificial Sequence
<220> FEATURE:
<223> OTHER INFORMATION: Description of Artificial Sequence:Synthetic

<400> SEQUENCE: 82
gagtccgggc tgtccacc                                                18

<210> SEQ ID NO 83
<211> LENGTH: 18
<212> TYPE: DNA
<213> ORGANISM: Artificial Sequence
<220> FEATURE:
<223> OTHER INFORMATION: Description of Artificial Sequence:Synthetic

<400> SEQUENCE: 83
atgttctcca gcgagtcc                                                18

<210> SEQ ID NO 84
<211> LENGTH: 18
<212> TYPE: DNA
<213> ORGANISM: Artificial Sequence
<220> FEATURE:
<223> OTHER INFORMATION: Description of Artificial Sequence:Synthetic

<400> SEQUENCE: 84
gggatgttct ccagcgag                                                18
```

-continued

<210> SEQ ID NO 85
<211> LENGTH: 18
<212> TYPE: DNA
<213> ORGANISM: Artificial Sequence
<220> FEATURE:
<223> OTHER INFORMATION: Description of Artificial Sequence:Synthetic

<400> SEQUENCE: 85
gacatgctcg tcgctgcg                                                   18

<210> SEQ ID NO 86
<211> LENGTH: 18
<212> TYPE: DNA
<213> ORGANISM: Artificial Sequence
<220> FEATURE:
<223> OTHER INFORMATION: Description of Artificial Sequence:Synthetic

<400> SEQUENCE: 86
cggacatgct cgtcgctg                                                   18

<210> SEQ ID NO 87
<211> LENGTH: 18
<212> TYPE: DNA
<213> ORGANISM: Artificial Sequence
<220> FEATURE:
<223> OTHER INFORMATION: Description of Artificial Sequence:Synthetic

<400> SEQUENCE: 87
tgtgcggaca tgctcgtc                                                   18

<210> SEQ ID NO 88
<211> LENGTH: 18
<212> TYPE: DNA
<213> ORGANISM: Artificial Sequence
<220> FEATURE:
<223> OTHER INFORMATION: Description of Artificial Sequence:Synthetic

<400> SEQUENCE: 88
ctctgtgcgg acatgctc                                                   18

<210> SEQ ID NO 89
<211> LENGTH: 18
<212> TYPE: DNA
<213> ORGANISM: Artificial Sequence
<220> FEATURE:
<223> OTHER INFORMATION: Description of Artificial Sequence:Synthetic

<400> SEQUENCE: 89
ccagctctgt gcggacat                                                   18

<210> SEQ ID NO 90
<211> LENGTH: 18
<212> TYPE: DNA
<213> ORGANISM: Artificial Sequence
<220> FEATURE:
<223> OTHER INFORMATION: Description of Artificial Sequence:Synthetic

<400> SEQUENCE: 90
cgggccagct ctgtgcgg                                                   18

<210> SEQ ID NO 91
<211> LENGTH: 18
<212> TYPE: DNA
<213> ORGANISM: Artificial Sequence
<220> FEATURE:
<223> OTHER INFORMATION: Description of Artificial Sequence:Synthetic

<400> SEQUENCE: 91
tgcgggccag ctctgtgc                                       18

<210> SEQ ID NO 92
<211> LENGTH: 18
<212> TYPE: DNA
<213> ORGANISM: Artificial Sequence
<220> FEATURE:
<223> OTHER INFORMATION: Description of Artificial   Sequence:Synthetic

<400> SEQUENCE: 92
gttcctgctt catgcggg                                       18

<210> SEQ ID NO 93
<211> LENGTH: 18
<212> TYPE: DNA
<213> ORGANISM: Artificial Sequence
<220> FEATURE:
<223> OTHER INFORMATION: Description of Artificial   Sequence:Synthetic

<400> SEQUENCE: 93
acgggttcct gcttcatg                                       18

<210> SEQ ID NO 94
<211> LENGTH: 18
<212> TYPE: DNA
<213> ORGANISM: Artificial Sequence
<220> FEATURE:
<223> OTHER INFORMATION: Description of Artificial   Sequence:Synthetic

<400> SEQUENCE: 94
gtagtcgtag gcttggat                                       18

<210> SEQ ID NO 95
<211> LENGTH: 18
<212> TYPE: DNA
<213> ORGANISM: Artificial Sequence
<220> FEATURE:
<223> OTHER INFORMATION: Description of Artificial   Sequence:Synthetic

<400> SEQUENCE: 95
cgaggtagtc gtaggctt                                       18

<210> SEQ ID NO 96
<211> LENGTH: 18
<212> TYPE: DNA
<213> ORGANISM: Artificial Sequence
<220> FEATURE:
<223> OTHER INFORMATION: Description of Artificial   Sequence:Synthetic

<400> SEQUENCE: 96
gtcttggcag agcactcg                                       18

<210> SEQ ID NO 97
<211> LENGTH: 18
<212> TYPE: DNA
<213> ORGANISM: Artificial Sequence
<220> FEATURE:
<223> OTHER INFORMATION: Description of Artificial   Sequence:Synthetic

<400> SEQUENCE: 97
acctcgcgca cgccttcc                                       18

<210> SEQ ID NO 98

<211> LENGTH: 18
<212> TYPE: DNA
<213> ORGANISM: Artificial Sequence
<220> FEATURE:
<223> OTHER INFORMATION: Description of Artificial Sequence:Synthetic

<400> SEQUENCE: 98
agacctcgcg cacgcctt                                                 18

<210> SEQ ID NO 99
<211> LENGTH: 18
<212> TYPE: DNA
<213> ORGANISM: Artificial Sequence
<220> FEATURE:
<223> OTHER INFORMATION: Description of Artificial Sequence:Synthetic

<400> SEQUENCE: 99
cgaagacctc gcgcacgc                                                 18

<210> SEQ ID NO 100
<211> LENGTH: 18
<212> TYPE: DNA
<213> ORGANISM: Artificial Sequence
<220> FEATURE:
<223> OTHER INFORMATION: Description of Artificial Sequence:Synthetic

<400> SEQUENCE: 100
ctcgaagacc tcgcgcac                                                 18

<210> SEQ ID NO 101
<211> LENGTH: 18
<212> TYPE: DNA
<213> ORGANISM: Artificial Sequence
<220> FEATURE:
<223> OTHER INFORMATION: Description of Artificial Sequence:Synthetic

<400> SEQUENCE: 101
gccgtctcga agacctcg                                                 18

<210> SEQ ID NO 102
<211> LENGTH: 18
<212> TYPE: DNA
<213> ORGANISM: Artificial Sequence
<220> FEATURE:
<223> OTHER INFORMATION: Description of Artificial Sequence:Synthetic

<400> SEQUENCE: 102
cgtggccgtc tcgaagac                                                 18

<210> SEQ ID NO 103
<211> LENGTH: 18
<212> TYPE: DNA
<213> ORGANISM: Artificial Sequence
<220> FEATURE:
<223> OTHER INFORMATION: Description of Artificial Sequence:Synthetic

<400> SEQUENCE: 103
gttctgggag ccgtagcg                                                 18

<210> SEQ ID NO 104
<211> LENGTH: 18
<212> TYPE: DNA
<213> ORGANISM: Artificial Sequence
<220> FEATURE:
<223> OTHER INFORMATION: Description of Artificial Sequence:Synthetic

<400> SEQUENCE: 104

```
gccgttctgg gagccgta                                                    18

<210> SEQ ID NO 105
<211> LENGTH: 18
<212> TYPE: DNA
<213> ORGANISM: Artificial Sequence
<220> FEATURE:
<223> OTHER INFORMATION: Description of Artificial  Sequence:Synthetic

<400> SEQUENCE: 105
gatgcagccg ttctggga                                                    18

<210> SEQ ID NO 106
<211> LENGTH: 18
<212> TYPE: DNA
<213> ORGANISM: Artificial Sequence
<220> FEATURE:
<223> OTHER INFORMATION: Description of Artificial  Sequence:Synthetic

<400> SEQUENCE: 106
gttgatgcag ccgttctg                                                    18

<210> SEQ ID NO 107
<211> LENGTH: 18
<212> TYPE: DNA
<213> ORGANISM: Artificial Sequence
<220> FEATURE:
<223> OTHER INFORMATION: Description of Artificial  Sequence:Synthetic

<400> SEQUENCE: 107
cagcagttga tgcagccg                                                    18

<210> SEQ ID NO 108
<211> LENGTH: 18
<212> TYPE: DNA
<213> ORGANISM: Artificial Sequence
<220> FEATURE:
<223> OTHER INFORMATION: Description of Artificial  Sequence:Synthetic

<400> SEQUENCE: 108
agcaccttgc agcagttg                                                    18

<210> SEQ ID NO 109
<211> LENGTH: 1058
<212> TYPE: DNA
<213> ORGANISM: Homo sapiens

<400> SEQUENCE: 109
gccttgactt catctcagct ccagagcccg ccctctcttc ctgcagcctg g gaacttcag     60 ccggctggag cccaccatgg ctgcaatccg aaagaagctg gtgatcgttg g ggatggtgc   120 ctgtgggaag acctgcctcc tcatcgtctt cagcaaggat cagtttccgg a ggtctacgt   180 ccctactgtc tttgagaact atattgcgga cattgaggtg gacggcaagc a ggtggagct   240 ggctctgtgg gacgcggaca ttgaggtgga cggcaagcag gtggagctgg c tctgtggga   300 cgacactgat gtcatcctca tgtgcttctc catcgacagc cctgacagcc t ggaaaacat   360 tcctgagaag tggaccccag aggtgaagca cttctgcccc aacgtgccca t catcctggt   420 ggggaataag aaggacctga ggcaagacga gcacaccagg agagagctgg c caagatgaa   480 gcaggagccc gttcggtctg aggaaggccg ggacatggcg aaccggatca g tgcctttgg   540 ctaccttgag tgctcagcca agaccaagga gggagtgcgg gaggtgtttg a gatggccac   600
```

-continued

```
tcgggctggc ctccaggtcc gcaagaacaa gcgtcggagg ggctgtccca t tctctgaga    660 tcccccaaa gggcccttttt cctacatgcc cctcccttc acagggtac a gaaattatc      720 cccctacaac cccagcctcc tgagggctcc atactgaagg ctccatttc a gttccctcc    780 tgcccaggac tgcattgttt tctagccccg aggtgtggca cgggccctcc c tcccagcgc    840 tctgggagcc acgcctatgc cctgcccttc ctcatgggcc cctggggatc t tgcccctt    900 gaccttcccc aaaggatggt cacacaccag cactttatac acttctggct c acaggaaag    960 tgtctgcagt agggacccag agtcccaggc ccctggagtt gtttctgcag g ggccttgtc   1020 tctcactgca tttggtcagg ggggcatgaa taaaggct                             1058

<210> SEQ ID NO 110
<211> LENGTH: 18
<212> TYPE: DNA
<213> ORGANISM: Artificial Sequence
<220> FEATURE:
<223> OTHER INFORMATION: Description of Artificial  Sequence:Synthetic

<400> SEQUENCE: 110
gagctgagat gaagtcaa                                                    18

<210> SEQ ID NO 111
<211> LENGTH: 18
<212> TYPE: DNA
<213> ORGANISM: Artificial Sequence
<220> FEATURE:
<223> OTHER INFORMATION: Description of Artificial  Sequence:Synthetic

<400> SEQUENCE: 111
gctgaagttc ccaggctg                                                    18

<210> SEQ ID NO 112
<211> LENGTH: 18
<212> TYPE: DNA
<213> ORGANISM: Artificial Sequence
<220> FEATURE:
<223> OTHER INFORMATION: Description of Artificial  Sequence:Synthetic

<400> SEQUENCE: 112
ccggctgaag ttcccagg                                                    18

<210> SEQ ID NO 113
<211> LENGTH: 18
<212> TYPE: DNA
<213> ORGANISM: Artificial Sequence
<220> FEATURE:
<223> OTHER INFORMATION: Description of Artificial  Sequence:Synthetic

<400> SEQUENCE: 113
ggcaccatcc ccaacgat                                                    18

<210> SEQ ID NO 114
<211> LENGTH: 18
<212> TYPE: DNA
<213> ORGANISM: Artificial Sequence
<220> FEATURE:
<223> OTHER INFORMATION: Description of Artificial  Sequence:Synthetic

<400> SEQUENCE: 114
aggcaccatc cccaacga                                                    18

<210> SEQ ID NO 115
<211> LENGTH: 18
```

```
<212> TYPE: DNA
<213> ORGANISM: Artificial Sequence
<220> FEATURE:
<223> OTHER INFORMATION: Description of Artificial  Sequence:Synthetic

<400> SEQUENCE: 115
tcccacaggc accatccc                                                  18

<210> SEQ ID NO 116
<211> LENGTH: 18
<212> TYPE: DNA
<213> ORGANISM: Artificial Sequence
<220> FEATURE:
<223> OTHER INFORMATION: Description of Artificial  Sequence:Synthetic

<400> SEQUENCE: 116
aggtcttccc acaggcac                                                  18

<210> SEQ ID NO 117
<211> LENGTH: 18
<212> TYPE: DNA
<213> ORGANISM: Artificial Sequence
<220> FEATURE:
<223> OTHER INFORMATION: Description of Artificial  Sequence:Synthetic

<400> SEQUENCE: 117
atgaggaggc aggtcttc                                                  18

<210> SEQ ID NO 118
<211> LENGTH: 18
<212> TYPE: DNA
<213> ORGANISM: Artificial Sequence
<220> FEATURE:
<223> OTHER INFORMATION: Description of Artificial  Sequence:Synthetic

<400> SEQUENCE: 118
ttgctgaaga cgatgagg                                                  18

<210> SEQ ID NO 119
<211> LENGTH: 18
<212> TYPE: DNA
<213> ORGANISM: Artificial Sequence
<220> FEATURE:
<223> OTHER INFORMATION: Description of Artificial  Sequence:Synthetic

<400> SEQUENCE: 119
tcaaagacag tagggacg                                                  18

<210> SEQ ID NO 120
<211> LENGTH: 18
<212> TYPE: DNA
<213> ORGANISM: Artificial Sequence
<220> FEATURE:
<223> OTHER INFORMATION: Description of Artificial  Sequence:Synthetic

<400> SEQUENCE: 120
ttctcaaaga cagtaggg                                                  18

<210> SEQ ID NO 121
<211> LENGTH: 18
<212> TYPE: DNA
<213> ORGANISM: Artificial Sequence
<220> FEATURE:
<223> OTHER INFORMATION: Description of Artificial  Sequence:Synthetic

<400> SEQUENCE: 121
```
agttctcaaa gacagtag                                                 18

<210> SEQ ID NO 122
<211> LENGTH: 18
<212> TYPE: DNA
<213> ORGANISM: Artificial Sequence
<220> FEATURE:
<223> OTHER INFORMATION: Description of Artificial Sequence:Synthetic

<400> SEQUENCE: 122
tgttttccag gctgtcag                                                 18

<210> SEQ ID NO 123
<211> LENGTH: 18
<212> TYPE: DNA
<213> ORGANISM: Artificial Sequence
<220> FEATURE:
<223> OTHER INFORMATION: Description of Artificial Sequence:Synthetic

<400> SEQUENCE: 123
tcgtcttgcc tcaggtcc                                                 18

<210> SEQ ID NO 124
<211> LENGTH: 18
<212> TYPE: DNA
<213> ORGANISM: Artificial Sequence
<220> FEATURE:
<223> OTHER INFORMATION: Description of Artificial Sequence:Synthetic

<400> SEQUENCE: 124
gtgtgctcgt cttgcctc                                                 18

<210> SEQ ID NO 125
<211> LENGTH: 18
<212> TYPE: DNA
<213> ORGANISM: Artificial Sequence
<220> FEATURE:
<223> OTHER INFORMATION: Description of Artificial Sequence:Synthetic

<400> SEQUENCE: 125
ctcctggtgt gctcgtct                                                 18

<210> SEQ ID NO 126
<211> LENGTH: 18
<212> TYPE: DNA
<213> ORGANISM: Artificial Sequence
<220> FEATURE:
<223> OTHER INFORMATION: Description of Artificial Sequence:Synthetic

<400> SEQUENCE: 126
cagaccgaac gggctcct                                                 18

<210> SEQ ID NO 127
<211> LENGTH: 18
<212> TYPE: DNA
<213> ORGANISM: Artificial Sequence
<220> FEATURE:
<223> OTHER INFORMATION: Description of Artificial Sequence:Synthetic

<400> SEQUENCE: 127
ttcctcagac cgaacggg                                                 18

<210> SEQ ID NO 128
<211> LENGTH: 18
<212> TYPE: DNA
<213> ORGANISM: Artificial Sequence

```
<220> FEATURE:
<223> OTHER INFORMATION: Description of Artificial  Sequence:Synthetic

<400> SEQUENCE: 128
actcaaggta gccaaagg                                                18

<210> SEQ ID NO 129
<211> LENGTH: 18
<212> TYPE: DNA
<213> ORGANISM: Artificial Sequence
<220> FEATURE:
<223> OTHER INFORMATION: Description of Artificial  Sequence:Synthetic

<400> SEQUENCE: 129
ctcccgcact ccctcctt                                                18

<210> SEQ ID NO 130
<211> LENGTH: 18
<212> TYPE: DNA
<213> ORGANISM: Artificial Sequence
<220> FEATURE:
<223> OTHER INFORMATION: Description of Artificial  Sequence:Synthetic

<400> SEQUENCE: 130
ctcaaacacc tcccgcac                                                18

<210> SEQ ID NO 131
<211> LENGTH: 18
<212> TYPE: DNA
<213> ORGANISM: Artificial Sequence
<220> FEATURE:
<223> OTHER INFORMATION: Description of Artificial  Sequence:Synthetic

<400> SEQUENCE: 131
ggccatctca aacacctc                                                18

<210> SEQ ID NO 132
<211> LENGTH: 18
<212> TYPE: DNA
<213> ORGANISM: Artificial Sequence
<220> FEATURE:
<223> OTHER INFORMATION: Description of Artificial  Sequence:Synthetic

<400> SEQUENCE: 132
cttgttcttg cggacctg                                                18

<210> SEQ ID NO 133
<211> LENGTH: 18
<212> TYPE: DNA
<213> ORGANISM: Artificial Sequence
<220> FEATURE:
<223> OTHER INFORMATION: Description of Artificial  Sequence:Synthetic

<400> SEQUENCE: 133
cccctccgac gcttgttc                                                18

<210> SEQ ID NO 134
<211> LENGTH: 18
<212> TYPE: DNA
<213> ORGANISM: Artificial Sequence
<220> FEATURE:
<223> OTHER INFORMATION: Description of Artificial  Sequence:Synthetic

<400> SEQUENCE: 134
gtatggagcc ctcaggag                                                18
```

<210> SEQ ID NO 135
<211> LENGTH: 18
<212> TYPE: DNA
<213> ORGANISM: Artificial Sequence
<220> FEATURE:
<223> OTHER INFORMATION: Description of Artificial Sequence:Synthetic

<400> SEQUENCE: 135
gagccttcag tatggagc                                                 18

<210> SEQ ID NO 136
<211> LENGTH: 18
<212> TYPE: DNA
<213> ORGANISM: Artificial Sequence
<220> FEATURE:
<223> OTHER INFORMATION: Description of Artificial Sequence:Synthetic

<400> SEQUENCE: 136
gaaaatggag ccttcagt                                                 18

<210> SEQ ID NO 137
<211> LENGTH: 18
<212> TYPE: DNA
<213> ORGANISM: Artificial Sequence
<220> FEATURE:
<223> OTHER INFORMATION: Description of Artificial Sequence:Synthetic

<400> SEQUENCE: 137
ggaactgaaa atggagcc                                                 18

<210> SEQ ID NO 138
<211> LENGTH: 18
<212> TYPE: DNA
<213> ORGANISM: Artificial Sequence
<220> FEATURE:
<223> OTHER INFORMATION: Description of Artificial Sequence:Synthetic

<400> SEQUENCE: 138
ggagggaact gaaaatgg                                                 18

<210> SEQ ID NO 139
<211> LENGTH: 18
<212> TYPE: DNA
<213> ORGANISM: Artificial Sequence
<220> FEATURE:
<223> OTHER INFORMATION: Description of Artificial Sequence:Synthetic

<400> SEQUENCE: 139
gcaggaggga actgaaaa                                                 18

<210> SEQ ID NO 140
<211> LENGTH: 18
<212> TYPE: DNA
<213> ORGANISM: Artificial Sequence
<220> FEATURE:
<223> OTHER INFORMATION: Description of Artificial Sequence:Synthetic

<400> SEQUENCE: 140
agggcagggc ataggcgt                                                 18

<210> SEQ ID NO 141
<211> LENGTH: 18
<212> TYPE: DNA
<213> ORGANISM: Artificial Sequence
<220> FEATURE:
<223> OTHER INFORMATION: Description of Artificial Sequence:Synthetic

<400> SEQUENCE: 141
ggaagggcag ggcatagg                                                    18

<210> SEQ ID NO 142
<211> LENGTH: 18
<212> TYPE: DNA
<213> ORGANISM: Artificial Sequence
<220> FEATURE:
<223> OTHER INFORMATION: Description of Artificial Sequence:Synthetic

<400> SEQUENCE: 142
catgaggaag ggcagggc                                                    18

<210> SEQ ID NO 143
<211> LENGTH: 18
<212> TYPE: DNA
<213> ORGANISM: Artificial Sequence
<220> FEATURE:
<223> OTHER INFORMATION: Description of Artificial Sequence:Synthetic

<400> SEQUENCE: 143
taaagtgctg gtgtgtga                                                    18

<210> SEQ ID NO 144
<211> LENGTH: 18
<212> TYPE: DNA
<213> ORGANISM: Artificial Sequence
<220> FEATURE:
<223> OTHER INFORMATION: Description of Artificial Sequence:Synthetic

<400> SEQUENCE: 144
cctgtgagcc agaagtgt                                                    18

<210> SEQ ID NO 145
<211> LENGTH: 18
<212> TYPE: DNA
<213> ORGANISM: Artificial Sequence
<220> FEATURE:
<223> OTHER INFORMATION: Description of Artificial Sequence:Synthetic

<400> SEQUENCE: 145
ttcctgtgag ccagaagt                                                    18

<210> SEQ ID NO 146
<211> LENGTH: 18
<212> TYPE: DNA
<213> ORGANISM: Artificial Sequence
<220> FEATURE:
<223> OTHER INFORMATION: Description of Artificial Sequence:Synthetic

<400> SEQUENCE: 146
cactttcctg tgagccag                                                    18

<210> SEQ ID NO 147
<211> LENGTH: 18
<212> TYPE: DNA
<213> ORGANISM: Artificial Sequence
<220> FEATURE:
<223> OTHER INFORMATION: Description of Artificial Sequence:Synthetic

<400> SEQUENCE: 147
agacactttc ctgtgagc                                                    18

<210> SEQ ID NO 148

```
<211> LENGTH: 18
<212> TYPE: DNA
<213> ORGANISM: Artificial Sequence
<220> FEATURE:
<223> OTHER INFORMATION: Description of Artificial  Sequence:Synthetic

<400> SEQUENCE: 148
actctgggtc cctactgc                                                    18

<210> SEQ ID NO 149
<211> LENGTH: 18
<212> TYPE: DNA
<213> ORGANISM: Artificial Sequence
<220> FEATURE:
<223> OTHER INFORMATION: Description of Artificial  Sequence:Synthetic

<400> SEQUENCE: 149
tgcagaaaca actccagg                                                    18

<210> SEQ ID NO 150
<211> LENGTH: 1284
<212> TYPE: DNA
<213> ORGANISM: Homo sapiens

<400> SEQUENCE: 150
gcttctcgag cccggagccg ctgccgccgc cccagctcc cccgcctcgg g agggcacc       60 aggtcactgc agccagaggg gtccagaaga gagaggaggc actgcctcac t acagcaact   120 gcacccacga tgcagagcat caagtgcgtg gtggtgggtg atgggctgt g ggcaagacg    180 tgcctgctca tctgctacac aactaacgct ttccccaaag agtacatccc c accgtgttc   240 gacaattaca gcgcgcagag cgcagttgac gggcgcacag tgaacctgaa c ctgtgggac   300 actgcgggcc aggaggagta tgaccgcctc cgtacactct cctaccctca g accaacgtt   360 ttcgtcatct gtttctccat tgccagtccg ccgtcctatg agaacgtgcg g cacaagtgg   420 catccagagg tgtgccacca ctgccctgat gtgcccatcc tgctggtggg c accaagaag   480 gacctgagag cccagcctga caccctacgc gcctcaagg agcagagcca g gcgcccatc   540 acaccgcagc agggccaggc actcgcgaaa cagatccacg ctgtgcgcta c ctcgaatgc   600 tcagccctgc aacaggatgg tgtcaaggaa gtgttcgccg aggctgtccg g gctgtgctc   660 aaccccacgc cgatcaagcg tgggcggtcc tgcatcctct tgtgaccctg g cacttggct   720 tggaggctgc ccctgccctc cccccaccag ttgtgccttg gtgccttgtc c gcctcagct   780 gtgccttaag gactaattct ggcacccctt tccagggggtt ccctgaatgc c tttttctct   840 gagtgccttt ttctccttaa ggaggcctgc agagaaaggg gctttgggct c tgcccctct   900 ggcttgggaa cactgggtat tctcatgagc tcatccaagc caaggttgga c ccctcccca   960 agaggccaac ccagtgcccc ctcccatttt ccgctactga ccagttcatc c agctttcca  1020 cacagttgtt gctgcctatt gtggtgccgc ctcaggttag gggctctcag c catctctaa  1080 cctctgccct cgctgctctt ggaattgcgc cccaagatg ctctctccct t ctccaatga  1140 gggagccaca gaatcctgag aaggtgaatg taccctaacc tgctcctctg t gcctaggcc  1200 ttacgcattt gctgactgac tcagcccca tgcttctggg gacctttcct a ccccccatca  1260 gcatcaataa aacctcctgt ctcc                                          1284

<210> SEQ ID NO 151
<211> LENGTH: 18
<212> TYPE: DNA
<213> ORGANISM: Artificial Sequence
```

```
<220> FEATURE:
<223> OTHER INFORMATION: Description of Artificial  Sequence:Synthetic

<400> SEQUENCE: 151
gacctggtgc ccctcccg                                                  18

<210> SEQ ID NO 152
<211> LENGTH: 18
<212> TYPE: DNA
<213> ORGANISM: Artificial Sequence
<220> FEATURE:
<223> OTHER INFORMATION: Description of Artificial  Sequence:Synthetic

<400> SEQUENCE: 152
tcttctggac ccctctgg                                                  18

<210> SEQ ID NO 153
<211> LENGTH: 18
<212> TYPE: DNA
<213> ORGANISM: Artificial Sequence
<220> FEATURE:
<223> OTHER INFORMATION: Description of Artificial  Sequence:Synthetic

<400> SEQUENCE: 153
ggcagtgcct cctctctc                                                  18

<210> SEQ ID NO 154
<211> LENGTH: 18
<212> TYPE: DNA
<213> ORGANISM: Artificial Sequence
<220> FEATURE:
<223> OTHER INFORMATION: Description of Artificial  Sequence:Synthetic

<400> SEQUENCE: 154
gtgcagttgc tgtagtga                                                  18

<210> SEQ ID NO 155
<211> LENGTH: 18
<212> TYPE: DNA
<213> ORGANISM: Artificial Sequence
<220> FEATURE:
<223> OTHER INFORMATION: Description of Artificial  Sequence:Synthetic

<400> SEQUENCE: 155
gcatcgtggg tgcagttg                                                  18

<210> SEQ ID NO 156
<211> LENGTH: 18
<212> TYPE: DNA
<213> ORGANISM: Artificial Sequence
<220> FEATURE:
<223> OTHER INFORMATION: Description of Artificial  Sequence:Synthetic

<400> SEQUENCE: 156
ccaccacgca cttgatgc                                                  18

<210> SEQ ID NO 157
<211> LENGTH: 18
<212> TYPE: DNA
<213> ORGANISM: Artificial Sequence
<220> FEATURE:
<223> OTHER INFORMATION: Description of Artificial  Sequence:Synthetic

<400> SEQUENCE: 157
ttgtgtagca gatgagca                                                  18
```

<210> SEQ ID NO 158
<211> LENGTH: 18
<212> TYPE: DNA
<213> ORGANISM: Artificial Sequence
<220> FEATURE:
<223> OTHER INFORMATION: Description of Artificial Sequence:Synthetic

<400> SEQUENCE: 158
aaagcgttag ttgtgtag                                              18

<210> SEQ ID NO 159
<211> LENGTH: 18
<212> TYPE: DNA
<213> ORGANISM: Artificial Sequence
<220> FEATURE:
<223> OTHER INFORMATION: Description of Artificial Sequence:Synthetic

<400> SEQUENCE: 159
gcgcgctgta attgtcga                                              18

<210> SEQ ID NO 160
<211> LENGTH: 18
<212> TYPE: DNA
<213> ORGANISM: Artificial Sequence
<220> FEATURE:
<223> OTHER INFORMATION: Description of Artificial Sequence:Synthetic

<400> SEQUENCE: 160
ggttcactgt gcgcccgt                                              18

<210> SEQ ID NO 161
<211> LENGTH: 18
<212> TYPE: DNA
<213> ORGANISM: Artificial Sequence
<220> FEATURE:
<223> OTHER INFORMATION: Description of Artificial Sequence:Synthetic

<400> SEQUENCE: 161
gtcccacagg ttcaggtt                                              18

<210> SEQ ID NO 162
<211> LENGTH: 18
<212> TYPE: DNA
<213> ORGANISM: Artificial Sequence
<220> FEATURE:
<223> OTHER INFORMATION: Description of Artificial Sequence:Synthetic

<400> SEQUENCE: 162
tgtacggagg cggtcata                                              18

<210> SEQ ID NO 163
<211> LENGTH: 18
<212> TYPE: DNA
<213> ORGANISM: Artificial Sequence
<220> FEATURE:
<223> OTHER INFORMATION: Description of Artificial Sequence:Synthetic

<400> SEQUENCE: 163
acgttggtct gagggtag                                              18

<210> SEQ ID NO 164
<211> LENGTH: 18
<212> TYPE: DNA
<213> ORGANISM: Artificial Sequence
<220> FEATURE:
<223> OTHER INFORMATION: Description of Artificial Sequence:Synthetic

```
<400> SEQUENCE: 164
caatggagaa acagatga                                                 18

<210> SEQ ID NO 165
<211> LENGTH: 18
<212> TYPE: DNA
<213> ORGANISM: Artificial Sequence
<220> FEATURE:
<223> OTHER INFORMATION: Description of Artificial  Sequence:Synthetic

<400> SEQUENCE: 165
cataggacgg cggactgg                                                 18

<210> SEQ ID NO 166
<211> LENGTH: 18
<212> TYPE: DNA
<213> ORGANISM: Artificial Sequence
<220> FEATURE:
<223> OTHER INFORMATION: Description of Artificial  Sequence:Synthetic

<400> SEQUENCE: 166
cgcacgttct cataggac                                                 18

<210> SEQ ID NO 167
<211> LENGTH: 18
<212> TYPE: DNA
<213> ORGANISM: Artificial Sequence
<220> FEATURE:
<223> OTHER INFORMATION: Description of Artificial  Sequence:Synthetic

<400> SEQUENCE: 167
acctctggat gccacttg                                                 18

<210> SEQ ID NO 168
<211> LENGTH: 18
<212> TYPE: DNA
<213> ORGANISM: Artificial Sequence
<220> FEATURE:
<223> OTHER INFORMATION: Description of Artificial  Sequence:Synthetic

<400> SEQUENCE: 168
agggcagtgg tggcacac                                                 18

<210> SEQ ID NO 169
<211> LENGTH: 18
<212> TYPE: DNA
<213> ORGANISM: Artificial Sequence
<220> FEATURE:
<223> OTHER INFORMATION: Description of Artificial  Sequence:Synthetic

<400> SEQUENCE: 169
cagcaggatg ggcacatc                                                 18

<210> SEQ ID NO 170
<211> LENGTH: 18
<212> TYPE: DNA
<213> ORGANISM: Artificial Sequence
<220> FEATURE:
<223> OTHER INFORMATION: Description of Artificial  Sequence:Synthetic

<400> SEQUENCE: 170
gggtgtcagg ctgggctc                                                 18

<210> SEQ ID NO 171
```

```
<211> LENGTH: 18
<212> TYPE: DNA
<213> ORGANISM: Artificial Sequence
<220> FEATURE:
<223> OTHER INFORMATION: Description of Artificial  Sequence:Synthetic

<400> SEQUENCE: 171
ccctgctgcg gtgtgatg                                               18

<210> SEQ ID NO 172
<211> LENGTH: 18
<212> TYPE: DNA
<213> ORGANISM: Artificial Sequence
<220> FEATURE:
<223> OTHER INFORMATION: Description of Artificial  Sequence:Synthetic

<400> SEQUENCE: 172
cgcgagtgcc tggccctg                                               18

<210> SEQ ID NO 173
<211> LENGTH: 18
<212> TYPE: DNA
<213> ORGANISM: Artificial Sequence
<220> FEATURE:
<223> OTHER INFORMATION: Description of Artificial  Sequence:Synthetic

<400> SEQUENCE: 173
gtagcgcaca gcgtggat                                               18

<210> SEQ ID NO 174
<211> LENGTH: 18
<212> TYPE: DNA
<213> ORGANISM: Artificial Sequence
<220> FEATURE:
<223> OTHER INFORMATION: Description of Artificial  Sequence:Synthetic

<400> SEQUENCE: 174
cattcgaggt agcgcaca                                               18

<210> SEQ ID NO 175
<211> LENGTH: 18
<212> TYPE: DNA
<213> ORGANISM: Artificial Sequence
<220> FEATURE:
<223> OTHER INFORMATION: Description of Artificial  Sequence:Synthetic

<400> SEQUENCE: 175
acaccatcct gttgcagg                                               18

<210> SEQ ID NO 176
<211> LENGTH: 18
<212> TYPE: DNA
<213> ORGANISM: Artificial Sequence
<220> FEATURE:
<223> OTHER INFORMATION: Description of Artificial  Sequence:Synthetic

<400> SEQUENCE: 176
gaacacttcc ttgacacc                                               18

<210> SEQ ID NO 177
<211> LENGTH: 18
<212> TYPE: DNA
<213> ORGANISM: Artificial Sequence
<220> FEATURE:
<223> OTHER INFORMATION: Description of Artificial  Sequence:Synthetic

<400> SEQUENCE: 177
```

```
acagcctcgg cgaacact                                              18

<210> SEQ ID NO 178
<211> LENGTH: 18
<212> TYPE: DNA
<213> ORGANISM: Artificial Sequence
<220> FEATURE:
<223> OTHER INFORMATION: Description of Artificial  Sequence:Synthetic

<400> SEQUENCE: 178
aagaggatgc aggaccgc                                              18

<210> SEQ ID NO 179
<211> LENGTH: 18
<212> TYPE: DNA
<213> ORGANISM: Artificial Sequence
<220> FEATURE:
<223> OTHER INFORMATION: Description of Artificial  Sequence:Synthetic

<400> SEQUENCE: 179
gcagcctcca agccaagt                                              18

<210> SEQ ID NO 180
<211> LENGTH: 18
<212> TYPE: DNA
<213> ORGANISM: Artificial Sequence
<220> FEATURE:
<223> OTHER INFORMATION: Description of Artificial  Sequence:Synthetic

<400> SEQUENCE: 180
aaaaggcatt cagggaac                                              18

<210> SEQ ID NO 181
<211> LENGTH: 18
<212> TYPE: DNA
<213> ORGANISM: Artificial Sequence
<220> FEATURE:
<223> OTHER INFORMATION: Description of Artificial  Sequence:Synthetic

<400> SEQUENCE: 181
gggtccaacc ttggcttg                                              18

<210> SEQ ID NO 182
<211> LENGTH: 18
<212> TYPE: DNA
<213> ORGANISM: Artificial Sequence
<220> FEATURE:
<223> OTHER INFORMATION: Description of Artificial  Sequence:Synthetic

<400> SEQUENCE: 182
gtcagtagcg gaaaatgg                                              18

<210> SEQ ID NO 183
<211> LENGTH: 18
<212> TYPE: DNA
<213> ORGANISM: Artificial Sequence
<220> FEATURE:
<223> OTHER INFORMATION: Description of Artificial  Sequence:Synthetic

<400> SEQUENCE: 183
agctggatga actggtca                                              18

<210> SEQ ID NO 184
<211> LENGTH: 18
<212> TYPE: DNA
```

<213> ORGANISM: Artificial Sequence
<220> FEATURE:
<223> OTHER INFORMATION: Description of Artificial Sequence:Synthetic

<400> SEQUENCE: 184
aactgtgtgg aaagctgg                                                 18

<210> SEQ ID NO 185
<211> LENGTH: 18
<212> TYPE: DNA
<213> ORGANISM: Artificial Sequence
<220> FEATURE:
<223> OTHER INFORMATION: Description of Artificial Sequence:Synthetic

<400> SEQUENCE: 185
accacaatag gcagcaac                                                 18

<210> SEQ ID NO 186
<211> LENGTH: 18
<212> TYPE: DNA
<213> ORGANISM: Artificial Sequence
<220> FEATURE:
<223> OTHER INFORMATION: Description of Artificial Sequence:Synthetic

<400> SEQUENCE: 186
gagggcagag gttagaga                                                 18

<210> SEQ ID NO 187
<211> LENGTH: 18
<212> TYPE: DNA
<213> ORGANISM: Artificial Sequence
<220> FEATURE:
<223> OTHER INFORMATION: Description of Artificial Sequence:Synthetic

<400> SEQUENCE: 187
caattccaag agcagcga                                                 18

<210> SEQ ID NO 188
<211> LENGTH: 18
<212> TYPE: DNA
<213> ORGANISM: Artificial Sequence
<220> FEATURE:
<223> OTHER INFORMATION: Description of Artificial Sequence:Synthetic

<400> SEQUENCE: 188
tggagaaggg agagagca                                                 18

<210> SEQ ID NO 189
<211> LENGTH: 18
<212> TYPE: DNA
<213> ORGANISM: Artificial Sequence
<220> FEATURE:
<223> OTHER INFORMATION: Description of Artificial Sequence:Synthetic

<400> SEQUENCE: 189
acattcacct tctcagga                                                 18

<210> SEQ ID NO 190
<211> LENGTH: 18
<212> TYPE: DNA
<213> ORGANISM: Artificial Sequence
<220> FEATURE:
<223> OTHER INFORMATION: Description of Artificial Sequence:Synthetic

<400> SEQUENCE: 190
gtcagcaaat gcgtaagg                                                 18

<210> SEQ ID NO 191
<211> LENGTH: 579
<212> TYPE: DNA
<213> ORGANISM: Artificial Sequence
<220> FEATURE:
<223> OTHER INFORMATION: Description of Artificial Sequence:Synthetic

<400> SEQUENCE: 191

```
atgcaggcca tcaagtgtgt ggtggtggga gacggagctg taggtaaaac t tgcctactg    60
atcagttaca caaccaatgc atttcctgga gaatatatcc ctactgtctt t gacaattat   120
tctgccaatg ttatggtaga tggaaaaccg gtgaatctgg gcttatggga t acagctgga   180
caagaagatt atgacagatt acgcccccta tcctatccgc aaacagatgt g ttcttaatt   240
tgcttttccc ttgtgagtcc tgcatcattt gaaaatgtcc gtgcaaagtg g tatcctgag   300
gtgcggcacc actgtcccaa cactcccatc atcctagtgg aactaaaact t gatcttagg   360
gatgataaag acacgatcga gaaactgaag gagaagaagc tgactcccat c acctatccg   420
cagggtctag ccatggctaa ggagattggt gctgtaaaat acctggagtg c tcggcgctc   480
acacagcgag gcctcaagac agtgtttgac gaagcgatcc gagcagtcct c tgcccgcct   540
cccgtgaaga gaggaagag aaaatgcctg ctgttgtaa                            579
```

<210> SEQ ID NO 192
<211> LENGTH: 45
<212> TYPE: DNA
<213> ORGANISM: Artificial Sequence
<220> FEATURE:
<223> OTHER INFORMATION: Description of Artificial Sequence:Synthetic

<400> SEQUENCE: 192

```
atagaatgtg agtctgaact cttacattta gaacaaacaa aacct           45
```

<210> SEQ ID NO 193
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 193

```
caaatgatgc aggactcaca                                       20
```

<210> SEQ ID NO 194
<211> LENGTH: 19
<212> TYPE: DNA
<213> ORGANISM: Artificial Sequence
<220> FEATURE:
<223> OTHER INFORMATION: Description of Artificial Sequence:Synthetic

<400> SEQUENCE: 194

```
caccaccaca cacttgatg                                        19
```

<210> SEQ ID NO 195
<211> LENGTH: 18
<212> TYPE: DNA
<213> ORGANISM: Artificial Sequence
<220> FEATURE:
<223> OTHER INFORMATION: Description of Artificial Sequence:Synthetic

<400> SEQUENCE: 195

```
ataagcccag attcaccg                                         18
```

<210> SEQ ID NO 196
<211> LENGTH: 19
<212> TYPE: DNA
<213> ORGANISM: Artificial Sequence
<220> FEATURE:
<223> OTHER INFORMATION: Description of Artificial Sequence:Synthetic

<400> SEQUENCE: 196
tgtttgcgga taggatagg                                             19

<210> SEQ ID NO 197
<211> LENGTH: 22
<212> TYPE: DNA
<213> ORGANISM: Artificial Sequence
<220> FEATURE:
<223> OTHER INFORMATION: Description of Artificial Sequence:Synthetic

<400> SEQUENCE: 197
gcttcttctc cttcagtttc tc                                         22

<210> SEQ ID NO 198
<211> LENGTH: 19
<212> TYPE: DNA
<213> ORGANISM: Artificial Sequence
<220> FEATURE:
<223> OTHER INFORMATION: Description of Artificial Sequence:Synthetic

<400> SEQUENCE: 198
cagcaccaat ctccttagc                                             19

<210> SEQ ID NO 199
<211> LENGTH: 19
<212> TYPE: DNA
<213> ORGANISM: Artificial Sequence
<220> FEATURE:
<223> OTHER INFORMATION: Description of Artificial Sequence:Synthetic

<400> SEQUENCE: 199
ctcttcctct tcttcacgg                                             19

<210> SEQ ID NO 200
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 200
cctaagatca agtttagttc                                            20

<210> SEQ ID NO 201
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 201
cgcacctcag gataccactt                                            20

<210> SEQ ID NO 202
<211> LENGTH: 20
<212> TYPE: DNA
<213> ORGANISM: Artificial Sequence
<220> FEATURE:
<223> OTHER INFORMATION: Description of Artificial Sequence:Synthetic

```
<400> SEQUENCE: 202
atctaccata acattggcag                                              20

<210> SEQ ID NO 203
<211> LENGTH: 20
<212> TYPE: DNA
<213> ORGANISM: Artificial Sequence
<220> FEATURE:
<223> OTHER INFORMATION: Description of Artificial  Sequence:Synthetic

<400> SEQUENCE: 203
taattgtcaa agacagtagg                                              20

<210> SEQ ID NO 204
<211> LENGTH: 20
<212> TYPE: DNA
<213> ORGANISM: Artificial Sequence
<220> FEATURE:
<223> OTHER INFORMATION: Description of Artificial  Sequence:Synthetic

<400> SEQUENCE: 204
gagcgccgag cactccaggt                                              20

<210> SEQ ID NO 205
<211> LENGTH: 20
<212> TYPE: DNA
<213> ORGANISM: Artificial Sequence
<220> FEATURE:
<223> OTHER INFORMATION: Description of Artificial  Sequence:Synthetic

<400> SEQUENCE: 205
gtcaaacact gtcttgaggc                                              20

<210> SEQ ID NO 206
<211> LENGTH: 20
<212> TYPE: DNA
<213> ORGANISM: Artificial Sequence
<220> FEATURE:
<223> OTHER INFORMATION: Description of Artificial  Sequence:Synthetic

<400> SEQUENCE: 206
atagaatgtg agtctgaact                                              20

<210> SEQ ID NO 207
<211> LENGTH: 25
<212> TYPE: DNA
<213> ORGANISM: Artificial Sequence
<220> FEATURE:
<223> OTHER INFORMATION: Description of Artificial  Sequence:Synthetic

<400> SEQUENCE: 207
cttacattta gaacaaacaa aacct                                        25

<210> SEQ ID NO 208
<211> LENGTH: 20
<212> TYPE: DNA
<213> ORGANISM: Artificial Sequence
<220> FEATURE:
<223> OTHER INFORMATION: Description of Artificial  Sequence:Synthetic

<400> SEQUENCE: 208
cccagctaag aattccgctc                                              20

<210> SEQ ID NO 209
```

<211> LENGTH: 18
<212> TYPE: DNA
<213> ORGANISM: Artificial Sequence
<220> FEATURE:
<223> OTHER INFORMATION: Description of Artificial Sequence:Synthetic

<400> SEQUENCE: 209
taaacgccga atctacgc                                                    18

<210> SEQ ID NO 210
<211> LENGTH: 18
<212> TYPE: DNA
<213> ORGANISM: Artificial Sequence
<220> FEATURE:
<223> OTHER INFORMATION: Description of Artificial Sequence:Synthetic

<400> SEQUENCE: 210
ataagccctg attcaccg                                                    18

<210> SEQ ID NO 211
<211> LENGTH: 18
<212> TYPE: DNA
<213> ORGANISM: Artificial Sequence
<220> FEATURE:
<223> OTHER INFORMATION: Description of Artificial Sequence:Synthetic

<400> SEQUENCE: 211
atacgccctg attcaccg                                                    18

<210> SEQ ID NO 212
<211> LENGTH: 18
<212> TYPE: DNA
<213> ORGANISM: Artificial Sequence
<220> FEATURE:
<223> OTHER INFORMATION: Description of Artificial Sequence:Synthetic

<400> SEQUENCE: 212
atacgccctg attaaccg                                                    18

<210> SEQ ID NO 213
<211> LENGTH: 18
<212> TYPE: DNA
<213> ORGANISM: Artificial Sequence
<220> FEATURE:
<223> OTHER INFORMATION: Description of Artificial Sequence:Synthetic

<400> SEQUENCE: 213
taaacgccga atctacgc                                                    18

<210> SEQ ID NO 214
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 214
aaactgctga agtacgcaca                                                  20

<210> SEQ ID NO 215
<211> LENGTH: 1175
<212> TYPE: DNA
<213> ORGANISM: Artificial Sequence
<220> FEATURE:
<223> OTHER INFORMATION: Description of Artificial Sequence:Synthetic

<400> SEQUENCE: 215

-continued

```
cccctgtgga gaagctgagg tcatcatcag atttgaaata tttaaagtgg a tacaaaatt        60 atttcagcaa tgcagacaat taagtgtgtt gttgtgggcg atggtgctgt t ggtaaaaca       120 tgtctcctga tatcctacac aacaaacaaa tttccatcgg aatatgtacc g actgttttt       180 gacaactatg cagtcacagt tatgattggt ggagaaccat atactcttgg a cttttttgat     240 actgcagggc aagaggatta tgacagatta cgaccgctga gttatccaca a acagatgta     300 tttctagtct gtttttcagt ggtctctcca tcttcatttg aaaacgtgaa a gaaaagtgg    360 gtgcctgaga taactcacca ctgtccaaag actcctttct tgcttgttgg g actcaaatt   420 gatctcagag atgacccctc tactattgag aaacttgcca agaacaaaca g aagcctatc   480 actccagaga ctgctgaaaa gctggcccgt gacctgaagg ctgtcaagta t gtggagtgt   540 tctgcactta cacagaaagg cctaaagaat gtatttgacg aagcaatatt g gctgccctg   600 gagcctccag aaccgaagaa gagccgcagg tgtgtgctgc tatgaacatc t ctccagagc   660 cctttctgca cagctggtgt cggcatcata ctaaaagcaa tgtttaaatc a aactaaaga   720 ttaaaaatta aaattcgttt ttgcaataat gacaaatgcc ctgcacctac c cacatgcac   780 tcgtgtgaga caaggcccat aggtatggcc ccccccttcc cctcccagt a ctagttaat     840 tttgagtaat tgtattgtca gaaaagtgat tagtactatt tttttttgtt g tttcaaaaa   900 aaaaatttt gtgtgtctgt ttttttttt ttttttttt gttgtttaaa a ggaaggcat       960 gcttgtggat gactctgtaa cagactaatt ggaattgttg aagctgctcc c tggttccac  1020 tctggagagt aatctgggac atcttagtgt tttgttttgt ttttttccct c ctctttttt  1080 ttgggggggga gtgtgtgggg ggtttgtttt ttagtcttgt tttttaatt c attaaccag   1140 tggttaagcc cttaagggag gaggacggat tgatt                               1175
```

<210> SEQ ID NO 216
<211> LENGTH: 25
<212> TYPE: DNA
<213> ORGANISM: Artificial Sequence
<220> FEATURE:
<223> OTHER INFORMATION: Description of Artificial  Sequence:Synthetic

<400> SEQUENCE: 216
ttcagcaatg cagacaatta agtgt                                           25

<210> SEQ ID NO 217
<211> LENGTH: 27
<212> TYPE: DNA
<213> ORGANISM: Artificial Sequence
<220> FEATURE:
<223> OTHER INFORMATION: Description of Artificial  Sequence:Synthetic

<400> SEQUENCE: 217
tgttgtgtag gatatcagga gacatgt                                         27

<210> SEQ ID NO 218
<211> LENGTH: 24
<212> TYPE: DNA
<213> ORGANISM: Artificial Sequence
<220> FEATURE:
<223> OTHER INFORMATION: Description of Artificial  Sequence:Synthetic

<400> SEQUENCE: 218
ttgtgggcga tggtgctgtt ggta                                            24

<210> SEQ ID NO 219

<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 219
taattgtctg cattgctgaa                                            20

<210> SEQ ID NO 220
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 220
ttaccaacag caccatcgcc                                            20

<210> SEQ ID NO 221
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 221
ccaccaatca taactgtgac                                            20

<210> SEQ ID NO 222
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 222
gtggataact cagcggtcgt                                            20

<210> SEQ ID NO 223
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 223
gaagatggag agaccactga                                            20

<210> SEQ ID NO 224
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 224
gtgagttatc tcaggcaccc                                            20

<210> SEQ ID NO 225
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 225

```
gcttctgttt gttcttggca                                         20

<210> SEQ ID NO 226
<211> LENGTH: 20
<212> TYPE: DNA
<213> ORGANISM: Artificial Sequence
<220> FEATURE:
<223> OTHER INFORMATION: Description of Artificial  Sequence:Synthetic

<400> SEQUENCE: 226
tgacagcctt caggtcacgg                                         20

<210> SEQ ID NO 227
<211> LENGTH: 20
<212> TYPE: DNA
<213> ORGANISM: Artificial Sequence
<220> FEATURE:
<223> OTHER INFORMATION: Description of Artificial  Sequence:Synthetic

<400> SEQUENCE: 227
cacctgcggc tcttcttcgg                                         20

<210> SEQ ID NO 228
<211> LENGTH: 20
<212> TYPE: DNA
<213> ORGANISM: Artificial Sequence
<220> FEATURE:
<223> OTHER INFORMATION: Description of Artificial  Sequence:Synthetic

<400> SEQUENCE: 228
ttgtctcaca cgagtgcatg                                         20

<210> SEQ ID NO 229
<211> LENGTH: 20
<212> TYPE: DNA
<213> ORGANISM: Artificial Sequence
<220> FEATURE:
<223> OTHER INFORMATION: Description of Artificial  Sequence:Synthetic

<400> SEQUENCE: 229
ttctgacaat acaattactc                                         20

<210> SEQ ID NO 230
<211> LENGTH: 20
<212> TYPE: DNA
<213> ORGANISM: Artificial Sequence
<220> FEATURE:
<223> OTHER INFORMATION: Description of Artificial  Sequence:Synthetic

<400> SEQUENCE: 230
ttacagagtc atccacaagc                                         20

<210> SEQ ID NO 231
<211> LENGTH: 20
<212> TYPE: DNA
<213> ORGANISM: Artificial Sequence
<220> FEATURE:
<223> OTHER INFORMATION: Description of Artificial  Sequence:Synthetic

<400> SEQUENCE: 231
cgatagtctc cacgtgaggc                                         20

<210> SEQ ID NO 232
<211> LENGTH: 20
<212> TYPE: DNA
```

```
<213> ORGANISM: Artificial Sequence
<220> FEATURE:
<223> OTHER INFORMATION: Description of Artificial  Sequence:Synthetic

<400> SEQUENCE: 232
gtaacgctcc tatggccagg                                              20

<210> SEQ ID NO 233
<211> LENGTH: 20
<212> TYPE: DNA
<213> ORGANISM: Artificial Sequence
<220> FEATURE:
<223> OTHER INFORMATION: Description of Artificial  Sequence:Synthetic

<400> SEQUENCE: 233
agactgactg ctcgtcgcga                                              20
```